US010786691B2

(12) United States Patent
Kao et al.

(10) Patent No.: US 10,786,691 B2
(45) Date of Patent: Sep. 29, 2020

(54) BREATHING APPARATUS

(71) Applicant: CleanSpace IP PTY LTD, Artarmon, New South Wales (AU)

(72) Inventors: Dan Kao, Northbridge (AU); Xiaoyi (Eric) Fu, Epping (AU); Alexander Virr, Mangrove Mountain (AU); John Michael Snow, Killarney Heights (AU); Damian Charles Johnson, Fairlight (AU)

(73) Assignee: CLEANSPACE IP PTY LTD, Artarmon (AU)

( * ) Notice: Subject to any disclaimer, the term of this patent is extended or adjusted under 35 U.S.C. 154(b) by 827 days.

(21) Appl. No.: 14/363,100

(22) PCT Filed: Dec. 5, 2012

(86) PCT No.: PCT/AU2012/001477
§ 371 (c)(1),
(2) Date: Jun. 5, 2014

(87) PCT Pub. No.: WO2013/082649
PCT Pub. Date: Jun. 13, 2013

(65) Prior Publication Data
US 2014/0373846 A1 Dec. 25, 2014

(30) Foreign Application Priority Data

Dec. 5, 2011 (AU) .................. 2011905052
Aug. 24, 2012 (AU) .................. 2012903663
Oct. 17, 2012 (AU) .................. 2012904536

(51) Int. Cl.
A62B 7/10 (2006.01)
A62B 18/02 (2006.01)
A61F 9/02 (2006.01)

(52) U.S. Cl.
CPC ............... *A62B 7/10* (2013.01); *A61F 9/02* (2013.01); *A62B 18/02* (2013.01)

(58) Field of Classification Search
CPC ......... A62B 18/02; A62B 7/10; A62B 18/006; A62B 7/02; A62B 7/12; A62B 18/10;
(Continued)

(56) References Cited

U.S. PATENT DOCUMENTS 3,863,630 A * 2/1975 Cavallo ................. A61M 16/00
128/203.27
4,011,865 A * 3/1977 Morishita ............. A62B 18/00
128/201.15

(Continued)

FOREIGN PATENT DOCUMENTS

| EP | 1 204 453 B1 | 7/2003 |
|----|-------------|--------|
| GB | 308790 | 5/1930 |

(Continued)

OTHER PUBLICATIONS

PCT/AU2012/001477 International Search Report dated Feb. 26, 2013 (6 pages including English translation).

(Continued)

*Primary Examiner* — Victoria Murphy
(74) *Attorney, Agent, or Firm* — Cooper & Dunham LLP

(57) ABSTRACT

The present invention relates to improvements to powered air purifying respirators (PAPR). PAPR are known generally for use in polluted environments. A typical PAPR comprises a powered impellor arranged to draw air from the atmosphere, a filter element and a mask to provide the filtered and pressurized air to the user. Embodiments of the present invention place a generator unit, comprising a filter and impellor for pressurizing the air, behind the head of the user, and include components for improving delivery of the air to the user and improving its quality.

12 Claims, 43 Drawing Sheets

(58) Field of Classification Search
CPC .... A62B 9/04; A62B 9/02; A61F 9/02; A61M 16/0069; A61M 16/06; Y10S 55/35; A41D 13/11

See application file for complete search history.

(56) References Cited

U.S. PATENT DOCUMENTS

| | | | |
|---|---|---|---|
| 4,671,268 A | | 6/1987 | Hunt |
| 4,951,662 A | * | 8/1990 | Townsend, Jr. .... A41D 13/1146 128/201.15 |
| 5,009,225 A | | 4/1991 | Vrabel |
| 5,046,492 A | * | 9/1991 | Stackhouse ........ A41D 13/1153 128/200.27 |
| 5,584,286 A | * | 12/1996 | Kippax .................. A62B 7/00 128/200.24 |
| 6,550,479 B1 | | 4/2003 | Duxbury |
| 7,481,221 B2 | * | 1/2009 | Kullik .................. A61M 16/06 128/200.27 |
| 2004/0003810 A1 | | 1/2004 | Templeton et al. |
| 2004/0182395 A1 | | 9/2004 | Brookman |
| 2004/0226566 A1 | * | 11/2004 | Gunaratnam ..... A61M 16/0666 128/207.18 |
| 2005/0284481 A1 | | 12/2005 | Meyer et al. |
| 2007/0215161 A1 | | 9/2007 | Frater et al. |
| 2007/0240716 A1 | | 10/2007 | Marx |
| 2010/0089397 A1 | * | 4/2010 | Klockseth ............ A62B 18/006 128/204.23 |
| 2010/0170513 A1 | * | 7/2010 | Bowditch ............. A61M 16/00 128/204.23 |
| 2010/0224190 A1 | | 9/2010 | Tilley et al. |

FOREIGN PATENT DOCUMENTS

| | | |
|---|---|---|
| GB | 468084 | 6/1937 |
| JP | S56-54858 A | 5/1981 |
| JP | 60-153145 U | 10/1985 |
| JP | 2006-520666 A | 9/2006 |
| JP | 2011-104404 A | 6/2011 |
| WO | WO 2008/011682 A1 | 1/2008 |
| WO | WO 2011/006206 A1 | 1/2011 |

OTHER PUBLICATIONS

Supplementary European Search Report for related application No. EP 12855694.1, dated Feb. 10, 2016, 10 pgs.

Extended European Search Report in corresponding European Application No. 16197865.5 dated Mar. 29, 2017, 9 pages.

Office Action, and English language translation thereof, in corresponding Japanese Application No. 2014-545034, dated Nov. 22, 2016, 11 pages.

Office Action, and English language translation thereof, in corresponding Japanese Application No. 2014-545034, dated Jun. 27, 2017, 9 pages.

Examination Report No. 1 in corresponding Australian Application No. 2012350140, dated Jan. 13, 2017, 4 pages.

First Office Action dated Dec. 21, 2015 from corresponding Chinese Application No. 201280069082.4 (8 pages including English translation).

Supplementary Partial European Search Report dated Oct. 12, 2015 (five pages) from corresponding EP Application No. 12855694.

Third Office Action dated Oct. 24, 2017 (11 pages including English translation) from corresponding Japanese Patent Application No. 2014-545034.

* cited by examiner

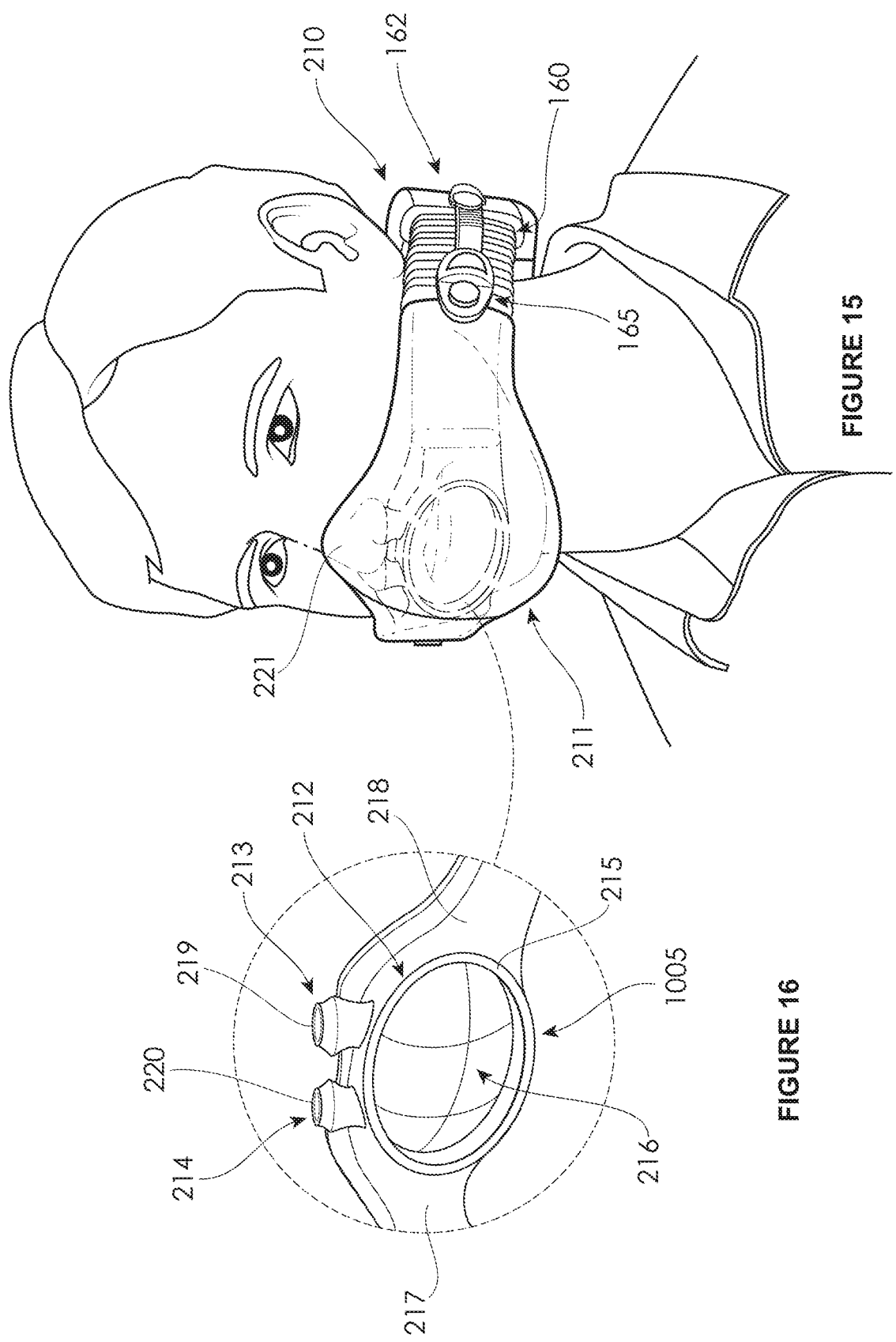

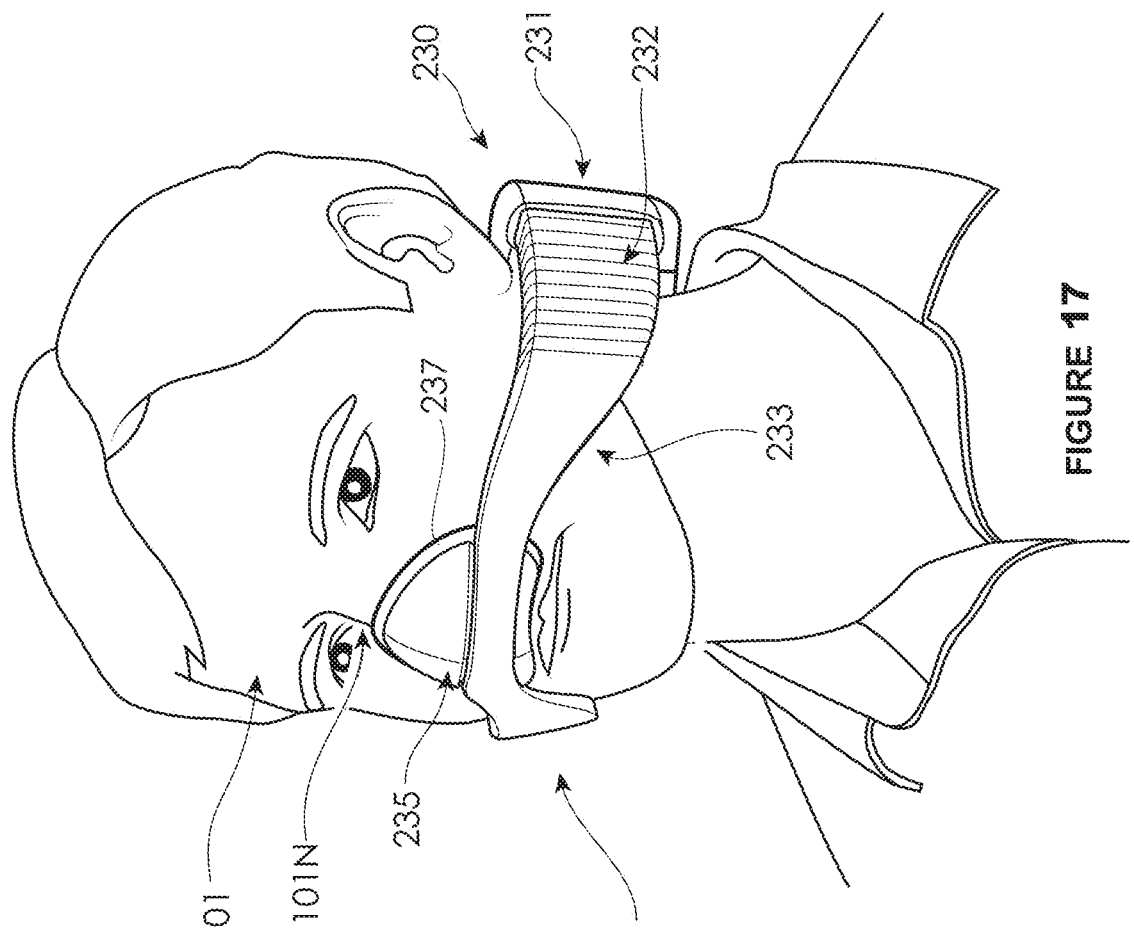
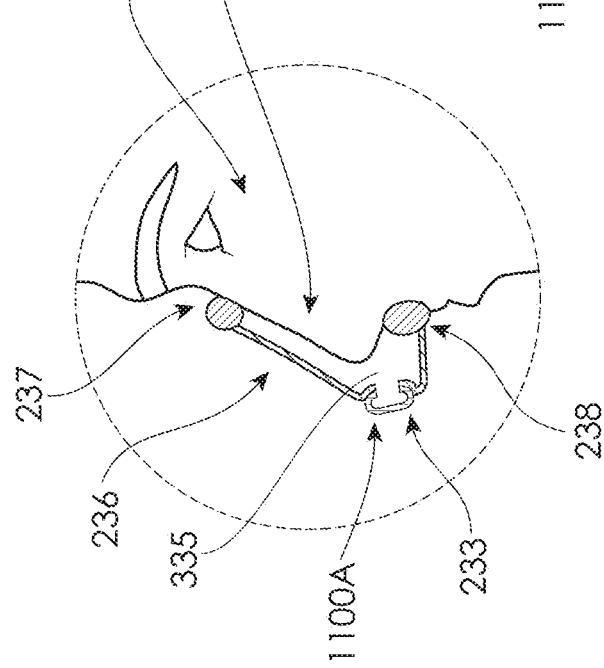
FIGURE 17
FIGURE 18

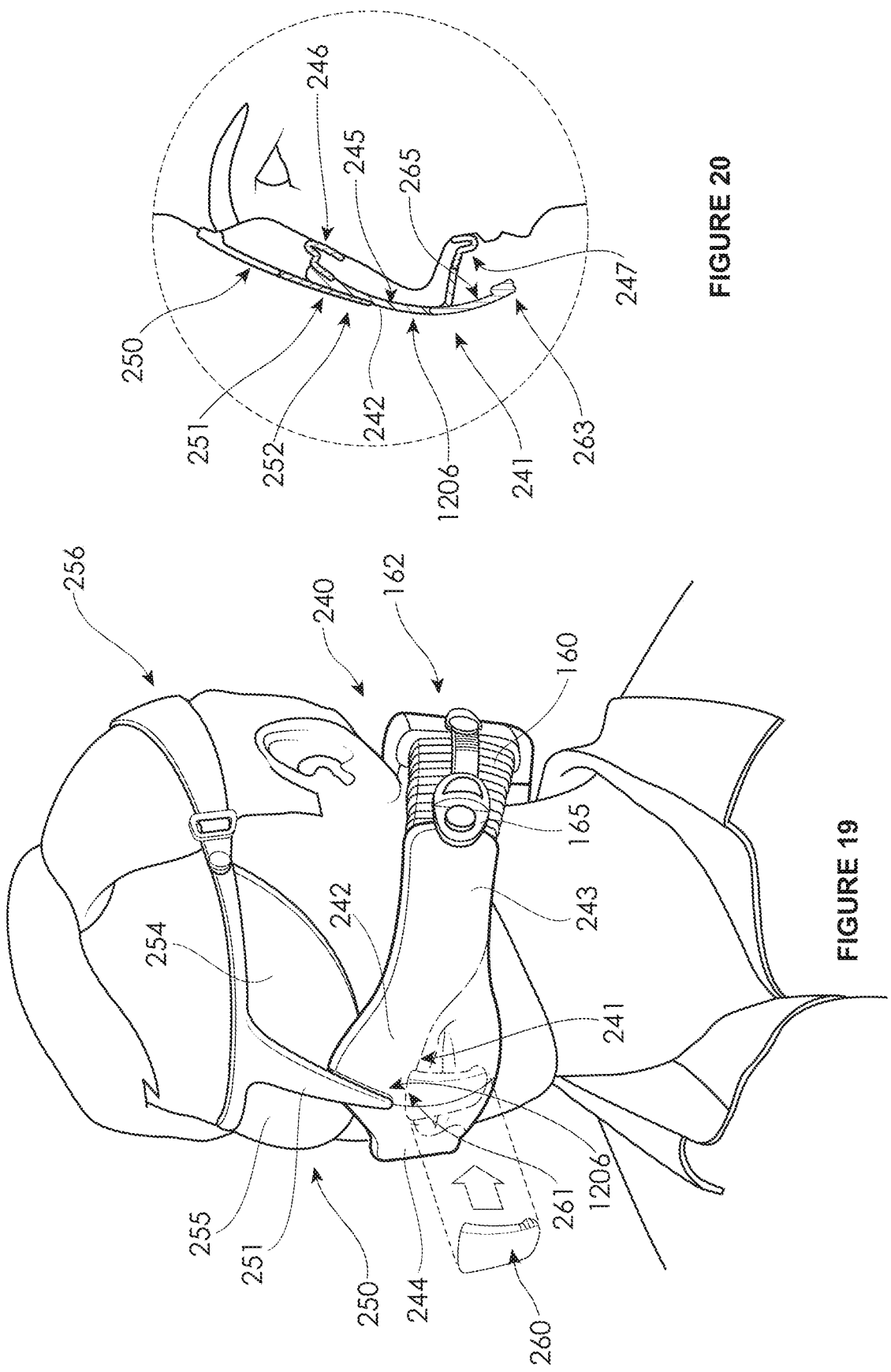

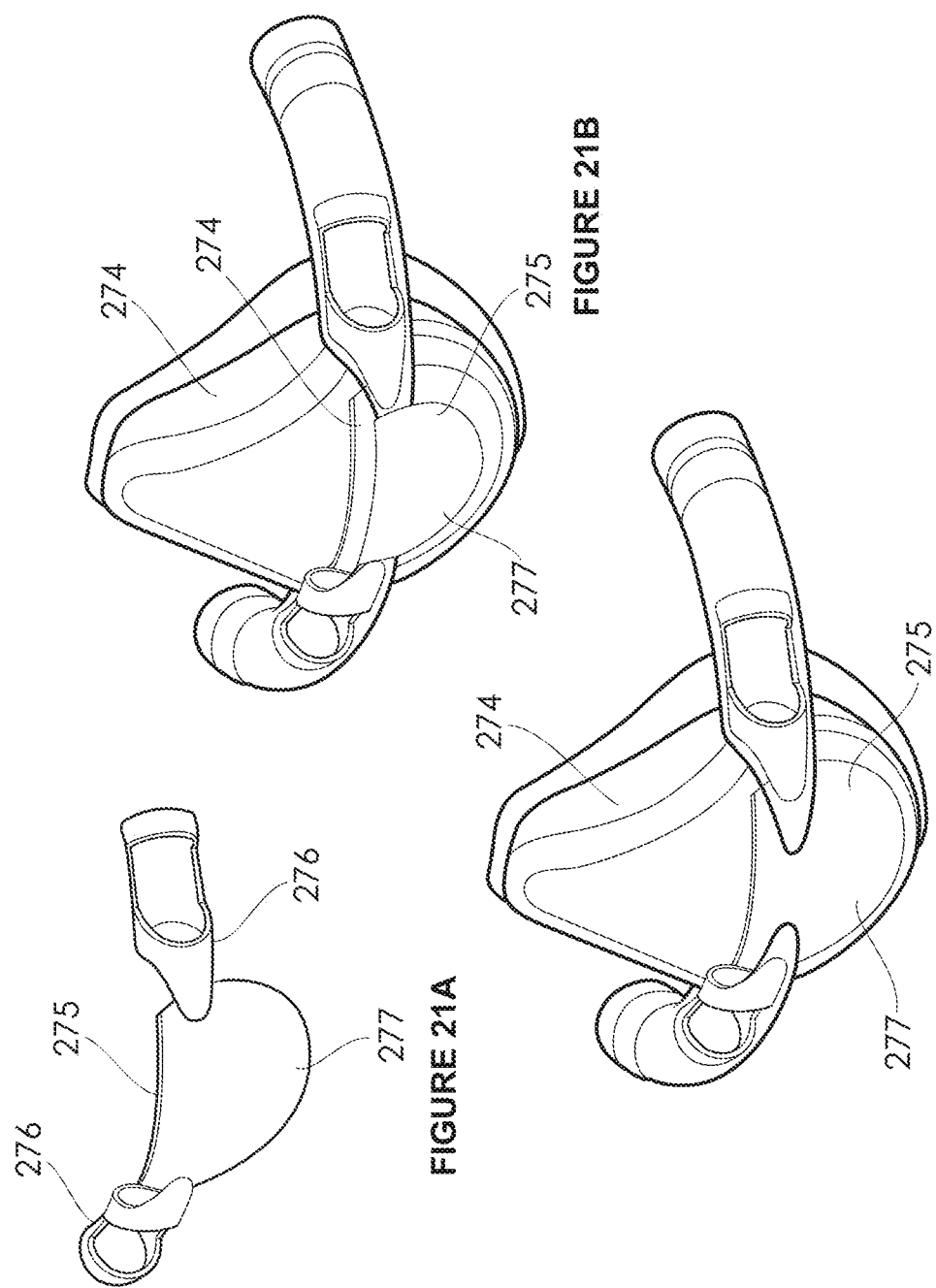

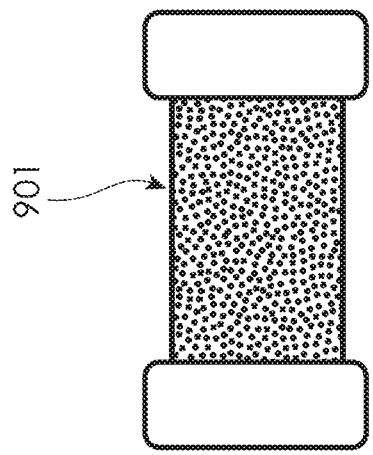
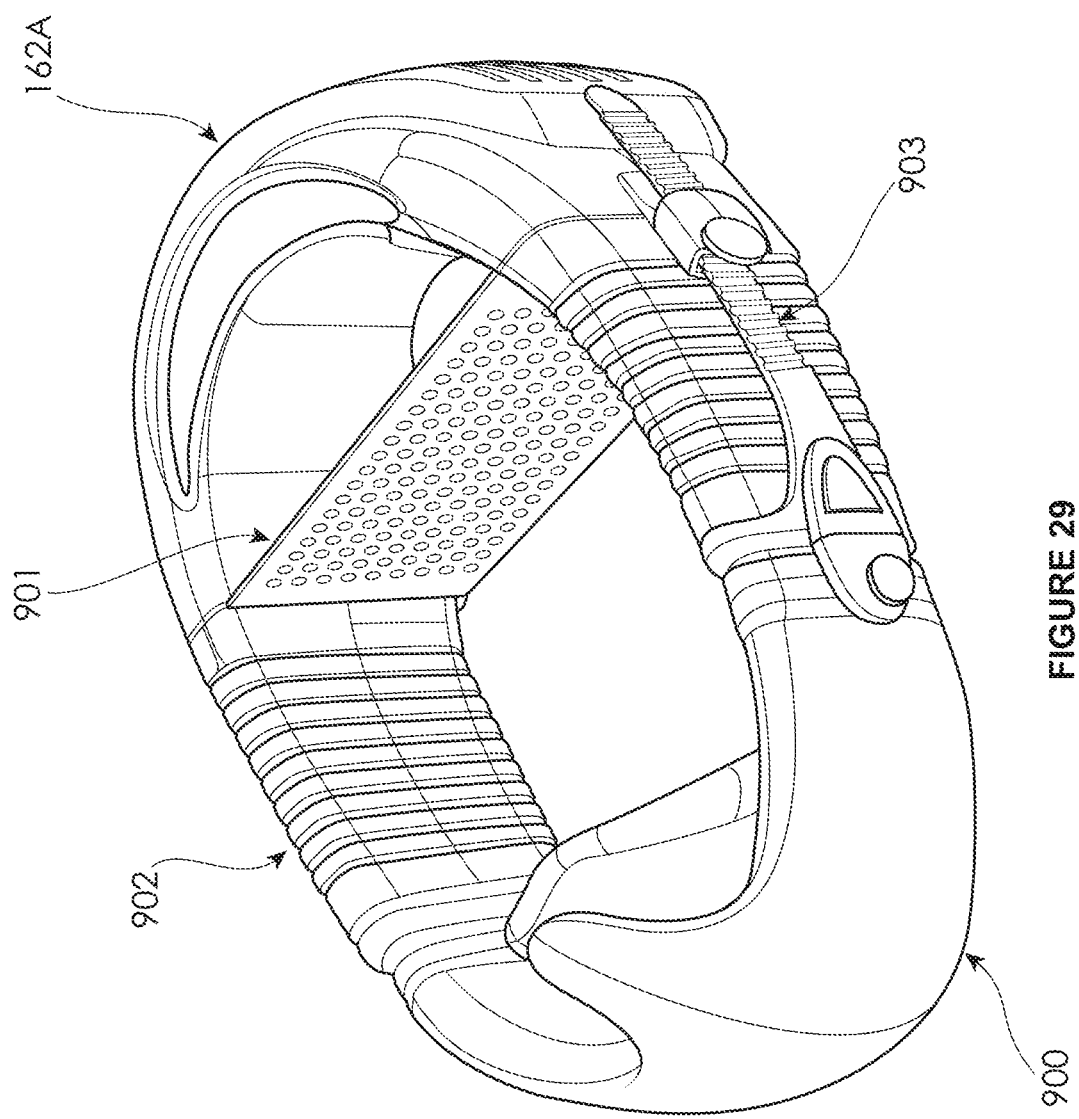
FIGURE 30
FIGURE 29

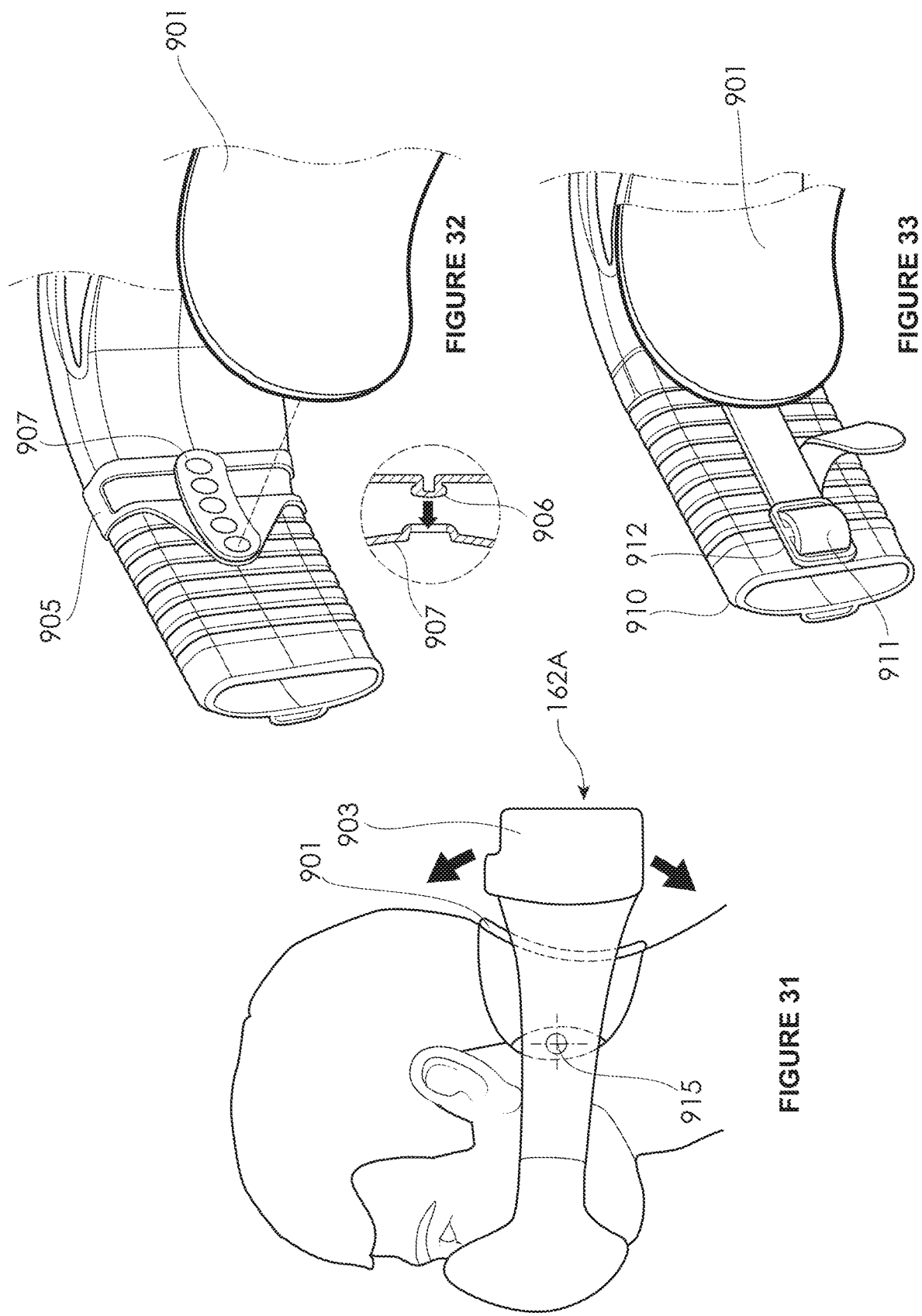

BREATHING APPARATUS

This application claims priority to International Application No. PCT/AU2012/001477 filed Dec. 5, 2012:Australian Patent Appin. No. 2011905052 filed Dec. 5, 2011: Australian Patent Appin. No. 2012903663 filed Aug. 24, 2012: and Australian Patent Appin. No. 2012904536 filed Oct. 17, 2012: the entire contents of each are incorporated herein by reference.

FIELD OF THE INVENTION

The present invention relates to improved breathing apparatus and, particularly, but not exclusively to improvements to powered air purifying respirators.

BACKGROUND OF THE INVENTION

Breathing apparatus such as powered air purifying respirators (PAPR) are known generally, for use in polluted environments. A typical PAPR comprises a powered impeller arranged to draw air from the atmosphere and a filter element through which the air is passed. The impeller positively pressurises the air and transfers it to a users airways via a mask. PAPR devices are used where the environment is heavily polluted or hazardous. Such environments include polluted industrial areas, hospitals and other potentially hazardous environments.

Conventional PAPRs tend to be bulky, awkward, and uncomfortable to wear. This is a disincentive to their use. Typical PAPRs are difficult to wear and use for long periods.

The present Applicants have designed a low profile "PAPR" which is less bulky and is more convenient to use. The present Applicant's PAPR is described in International (PCT) Patent Application No. PCT/AU2010/000902, the disclosure of which is incorporated in this document by reference.

A need exists for further improvements in PAPRs, to facilitate functionality and comfort.

SUMMARY OF THE INVENTION

In accordance with a first aspect, the present invention provides a breathing apparatus, comprising an air flow generator, a filter and an airway, the air flow generator being arranged to generate positive pressure air flow, the filter being arranged to filter air entering the breathing apparatus, and the airway being arranged to transport the positively pressurised air and being arranged to connect to a mask for providing the pressurised and filtered air to the airway of a user.

In an embodiment, the generator unit comprises a filter housing arranged to mount one or more filters. In a further embodiment, a further filter adaptor is arranged to be mounted to the generator unit, the further filter adaptor being arranged to receive a further filter unit.

In an embodiment, the generator unit comprises a removable filter cover, arranged to be removed and replaced with the further filter adaptor.

In an embodiment, the airway includes an airway connector for connecting the airway to the mask, to allow air flow into the mask to the user's airway.

In an embodiment, the air flow generator and filter are housed in a generator unit arranged to be positioned remote from the mask. The generator unit may be arranged to be mounted about the users person. In an embodiment, the unit is arranged to be mounted on the shoulder of the user. In another embodiment, the unit may be mounted behind the neck of the user. The unit may be mounted on the head of the user. In another embodiment, the unit may be mounted on a belt. In another embodiment, the unit may be mounted underneath an arm of a user, using a shoulder strap. The unit may be mounted elsewhere about the person of the user.

In an embodiment, an exhalation valve mounted in the mask for allowing air to be exhaled.

In an embodiment, the exhalation valve comprises a filter arranged to filter air being exited to the environment.

In an embodiment, a separate airway for exhaust air is arranged to communicate with the mask and carries exhaust air away from the mask.

In an embodiment, the mask may be removable from the generator unit and airway. In an embodiment the mask may be a disposable mask. In another embodiment, the mask may be cleanable.

An advantage of the breathing apparatus in accordance with an embodiment, is that the generator unit may be retained, and masks may be disposed of or washed separately. The airway can be plugged into a new mask or a washed mask. At least an embodiment has the advantage that it can be used domestically to cut intake of air pollution in urban areas. For example, it may be used by pedestrians, cyclists and others.

In one embodiment, air exhaust is via the mask and/or sides of the mask. In a further embodiment, a separate exhaust valve may be provided in the mask.

In another embodiment, a separate airway is connected to the mask for exhaust. In an embodiment, the separate airway may be provided with a further filter for filtering the exhaust gas before it is exited to the environment.

In an embodiment, the mask is of a material and flexibility so as to conform with the profile of the user's face.

The apparatus may be arranged to be used with a disposable mask, as discussed above, or may be arranged to be used with a non-disposable mask. In an embodiment, the breathing apparatus comprises a mask which is intended to be used repeatedly. The mask may be of resilient plastics material such as silicone. In an embodiment, the mask may be arranged to conform with the user's face.

In an embodiment, a mask for use with the breathing apparatus incorporates one or more features which facilitate wearing comfort. In an embodiment, the mask has a top portion which is arranged to sit proximate the nose of a user, and the top portion incorporates a resilient structural feature enabling the top part to flex to accommodate the user's nose.

In an embodiment, the resilient structural feature comprises a bellows arrangement, arranged to compress and expand.

In an embodiment, the mask comprises a face contacting border comprising a thinner wall section to facilitate comfort against the face.

In an embodiment, an area arranged to contact the persons face comprises a thinner wall section. The area may also comprise a gel cushion to facilitate comfort against the nose and/or face.

In an embodiment, the breathing apparatus may comprise a mask which is arranged to surround the mouth of the user but not the nose. In an embodiment, nose plugs extend from a top part of the mouth surrounding mask and are arranged to be inserted within the nostrils of the user. This results in a low profile mask which can advantageously be used with goggles or glasses without the mask getting in the way of the goggles or glasses. In an embodiment, passageways may be provided within the nose plugs to allow air communication between the interior of the mask and the user's nose.

In an embodiment, the breathing apparatus comprises a mask which is arranged to surround only the nasal orifices of a user and leave the mouth exposed. The user can therefore still talk and filtered air is still supplied to the nasal passageways for breathing.

In an embodiment, the breathing apparatus comprises a mask arrangement, comprising a mask scaffold arranged to support a cover. The cover may be relatively soft and flexible. The flexible cover is arranged to cover a person's nose and/or mouth openings and provide a volume for containing the filtered air.

In an embodiment, the cover, or a portion of the cover, is not flexible and is arranged to convey sound, so that a user can talk through the mask.

In an embodiment, the mask being connected to eyewear for the user.

In an embodiment, a decorative cover is included for the mask.

In an embodiment, the airway comprises airway walls defining an enclosed airway channel.

In an embodiment, the airway comprises an airway chassis which is arranged to extend to the mask to provide filtered air into the mask. In an embodiment, the airway chassis extends over the front of the mask, openings are provided in the chassis coinciding with openings in the mask, to convey air into the mask. In this embodiment, the chassis may provide additional support for the mask.

In an embodiment, the generator unit comprises a filter housing arranged to mount one or more filters.

In an embodiment, a further filter adapter is arranged to be mounted to the generator unit, the filter adapter being arranged to receive a further filter unit.

In an embodiment, the generator unit comprises a removable filter cover, arranged to be removed and replaced with the further filter adapter.

In an embodiment, the filter comprises a filter housing arranged to receive and mount filters. The filters may be replaced from time to time when they have been used.

In an embodiment, the filter housing comprises a further filter mounting portion, arranged to receive additional filter components to provide extra filtering.

In an embodiment, the breathing apparatus comprises a pair of arms arranged to extend from the mask or a mask support, to support the breathing apparatus relative to the user. In an embodiment, the arms are arranged to extend to the neck of the user. In an embodiment, the arms may join behind the neck in order to support the breathing apparatus.

In an embodiment, a separate neck pad may be connected to the arms at points away from the mask, and be used to provide further support to the breathing apparatus when mounted on the user. In an embodiment, supports extend from the arms and comprise hooks arranged to fit over the ears of a user to provide further support.

In an embodiment, supports extend from the arms and are connected to form a head band arranged to go over the head of the user and provide support.

In an embodiment, the arms incorporate the airway.

In an embodiment, the breathing apparatus comprises a pair of arms extending from the mask and connecting to a generator unit arranged, in use, to be mounted via the arms at the rear of the users head.

In an embodiment, the generator unit is spaced away from the back of the users head to allow the user to tilt their head without interference with the generator unit. In this embodiment, a separate neck support may be provided arranged to abut the neck of the user during use.

In an embodiment, the breathing apparatus comprises a power supply arranged to provide power to the breathing apparatus.

In an embodiment, the power supply comprises a battery mounted by the breathing apparatus.

In an embodiment, the breathing apparatus may comprise a supplementary power supply which can, in use, be added to the breathing apparatus. The supplementary power supply may comprise a power supply mounting arranged to mount a battery. The power supply mounting may be arranged to be mounted to the breathing apparatus.

In an embodiment, the airflow generator is arranged to generate a pressure within the mask from 0.01 to 4 cm water.

In an embodiment, the airflow generator is arranged to generate pressure within the mask from 0.1 cm water to 2.5 cm water.

In an embodiment, a control unit to control the airflow generator is arranged to vary output in accordance with the user's breathing.

An embodiment is arranged to vary the airflow output during a breathing cycle of the user.

In an embodiment, the breathing apparatus comprises a bypass arrangement, which is arranged to enable airflow to bypass the airflow generator in a non-powered mode of the breathing apparatus. This has the advantage of reducing resistance to airflow which may be caused by the airflow generator when it is not operating. This enables a user to still breathe relatively freely, when the airflow generator is not operating. In an embodiment, the bypass arrangement comprises a manifold and bypass valve.

Some embodiments of the present invention may be utilised primarily for domestic application. Lightweight versions which utilise disposable masks are particularly suited for domestic application. Versions with washable masks that are intended to be used more than once may also be used domestically, however. Embodiments intended for industrial use will likely have more filtering capability and perhaps more powerful motors and heavier masks. Their use domestically is not excluded.

In an embodiment the breathing apparatus provides a positive air pressure which is slightly above that of the ambient air pressure to ensure that positive air flow occurs in the mask towards the user's airway to facilitate inhalation. The air pressure will generally not be very great, as the user is able to inhale under their own power and inhalation should not be forced by a large air pressure. In an embodiment, the breathing apparatus provides a pressure internal to the mask of no more than 3 cm of water.

In an embodiment, the breathing apparatus provides a pressure internal to the mask of between 0.1 and 3.5 cm of water. In an embodiment the pressure provided is between 1 and 2.5 cm of water. In an embodiment, the pressure provided is between 1.5 and 2.2 cm of water.

In accordance with a second aspect, the present invention provides a mask arranged to surround at least the nose orifices of a user, the mask having a top portion which is arranged to sit proximate the nose of a user, the top portion incorporating a resilient structural feature enabling the top portion to flex to accommodate the user's nose.

In an embodiment, the mask is arranged for use with a powered air purifying respirator.

In accordance with a third aspect, the present invention provides a mask arranged to surround the mouth and/or nose orifices of a user, the mask having an area arranged to contact the person's face comprising a wall section relatively thinner than the rest of the mask.

In an embodiment, at least a portion of the area also comprises a gel cushion arranged to facilitate comfort against the user's face.

In an embodiment, the mask is arranged for use with a powered air purifying respirator.

In accordance with a fourth aspect, the present invention provides a mask arranged to surround the mouth of a user but not to surround the nose orifices.

In an embodiment, the mask comprises a pair of nose plugs extending from the mask and being arranged to be inserted within the nostrils of the user.

In an embodiment, passageways are provided within the nose plugs to allow air communication between the interior of the mask and the user's nose.

In an embodiment, the mask may be arranged for use with a powered air purifying respirator.

In accordance with a fifth aspect, the present invention provides a mask which is arranged to surround only the nasal orifices of a user and leave the mouth exposed.

In an embodiment, the mask is arranged for use with a powered air purifying respirator.

In accordance with a sixth aspect, the present invention provides a mask arrangement, comprising a mask scaffold arranged to support a cover arranged to surround the mouth and/or nose orifices of a user.

In an embodiment, the mask arrangement is arranged for use with a powered air purifying respirator.

In accordance with a seventh aspect, the present invention provides a mask arranged to cover the mouth and/or nose orifices of a user and comprising a relatively rigid portion of the mask which enables transmission of sound.

In embodiments of the present invention, a powered air respirator may comprise a generator unit for generating positively pressurised and filtered air. In one embodiment, the generator unit is mounted in a housing arranged to be positioned, in use, on the back of the neck of the user.

In accordance with an eighth aspect, the present invention provides a cooling device which is arranged to be used with a powered air respirator having a housing arranged to be mounted at the neck, the cooling device being arranged to be positioned between the neck mounted housing and the neck of the user.

In an embodiment, the cooling device comprises a pad which can be cooled by refrigeration and placed on a surface of the neck mounted housing, proximate the neck, to keep the neck cool.

In accordance with a ninth aspect, the present invention provides a breathing apparatus, comprising an airflow generator, the airflow generator being arranged to generate positive pressure airflow, and an air way being arranged to transport the positively pressurized air to a mask for providing the pressurized air to the airway of a user, and a control unit for controlling the airflow generator responsive to the breathing of a user.

In an embodiment, the control unit is arranged to vary the airflow generator output during a breathing cycle of the user.

In an embodiment, the control unit is arranged to vary the output of the airflow generator in response to the breathing rate of the user.

BRIEF DESCRIPTION OF THE DRAWINGS

Features and advantages of the present invention will become apparent from the following description of embodiments thereof, by way of example only, with reference to the accompanying drawings, in which;

FIG. 15 is an illustration of a further embodiment of the present invention;

FIG. 16 is a view of the inside of the mask arrangement of the embodiment of FIG. 15;

FIG. 17 is an illustration of a further embodiment of the present invention;

FIG. 18 is a sectional view of the mask arrangement of the embodiment of FIG. 17;

FIG. 19 is an illustration of a further embodiment of the present invention;

FIG. 20 is a sectional view of the mask arrangement of the embodiment of FIG. 19;

FIG. 21A is an illustration of a "skeleton" which may be used with embodiments similar to the embodiment of FIG. 21;

FIG. 21B is an illustration showing a mask utilising the skeleton of FIG. 21A;

FIG. 21C is a further view of a mask utilising the skeleton of FIG. 21A;

FIG. 29 is a perspective view of a breathing apparatus in accordance with a further embodiment of the present invention;

FIG. 30 is a plan view of a neck support for use with the breathing apparatus of the embodiment of FIG. 29;

FIG. 31 is a side view of the apparatus of FIG. 29 shown being worn by a user;

FIG. 32 is a detail of the embodiment of FIG. 29, illustrating connection of a neck support to the breathing apparatus;

FIG. 33 is a detail of the embodiment of FIG. 29 showing an alternative connection for a neck support;

DETAILED DESCRIPTION OF EMBODIMENTS

Figure 1:
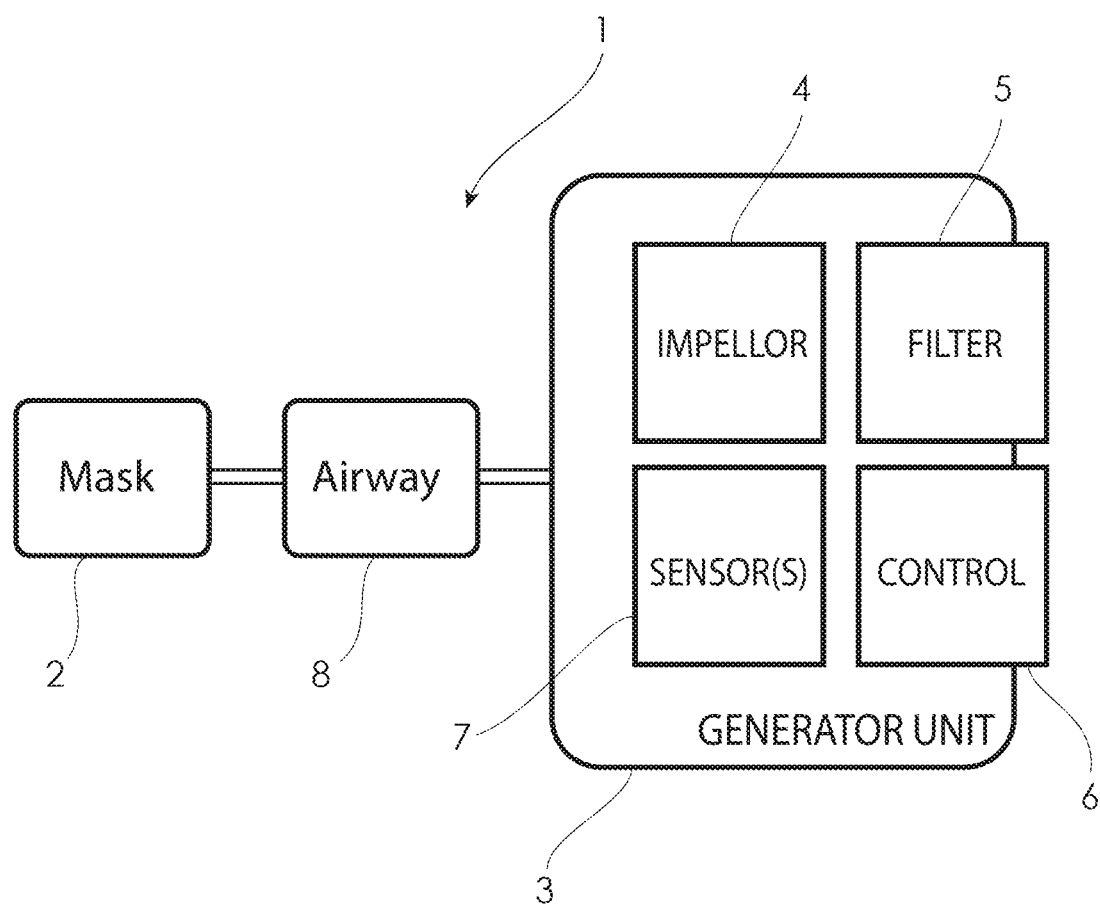
FIG. 1 is a block diagram representing components of a breathing apparatus in accordance with an embodiment of the present invention.

FIG. 1 is a block diagram showing components of a powered air purifying respirator (PAPR) system, in accordance with embodiments of the present invention. The PAPR system 1 comprises the following components:

(a) a mask 2, which, in use, is arranged to form a closed chamber about the mouth and/or nose orifices of a user. The chamber formed by the mask is arranged to receive purified air which, in this example, is under positive pressure;

(b) an air flow generator and filter unit 3 (generator unit). In this example, the air flow generator comprises an impeller 4 with power supply (not shown) which is arranged to positively pressurise air drawn in from the outside environment. The generator unit 3 also comprises a filter 5 arranged to filter the air, a control unit 6 for controlling the generator unit 3, and, in some embodiments, one or more sensors for sensing air pressure/air quality.

(c) An airway 8 which is arranged to convey positively pressurised air from the generator unit 3 to the mask 2.

The mask 3 may comprise any form of mask which can form a closed chamber about the mouth and/or nose orifices of the user. It may comprise a mask which can be separated from the rest of the apparatus and be disposed of. It may comprise a mask which is not intended to be disposable, but instead can be washable.

Positively pressurised and filtered air from the generator unit 3 is introduced into the air chamber formed by the mask 3 via the airway 20. Positive pressure within the chamber is advantageous, as it reduces the amount of unfiltered air which may enter the chamber from around the mask edges.

The mask may be arranged such that when the user exhales, the exhaled air is exhausted from the mask. The mask may be of filter material itself, in which case exhaust may be via the filter material. Alternatively or additionally, exhaust may be via the edges of the mask, surrounding the face.

In an embodiment, an exhaust valve (see later) may be provided for use with the mask 3. The exhaust valve may allow exhaust air to escape, when a user is breathing heavily, to relieve the pressure in the air chamber.

In another embodiment, the airway may include a return air pathway, which receives exhaust air, for exhausting via the further, return airway. In embodiments (see later) a further filter may be provided to filter the exhaled air.

In embodiments, the generator unit 3 may be mounted in a convenient location, on the user's shoulder or behind the user's neck. The generator unit 3 may be placed in different positions and may be of different housing shapes.

It may be placed under the arm for example, or in a jacket pocket (may be a convenient rectangular shape similar to a smart phone or like device). It may be secured around the back of the neck, for example. It may be positioned on a user's belt. It may be placed in any other position and the shape may be adapted accordingly.

The generator unit 3 may be provided in one or more versions. Each version may have different functionality as required by factors such as cost and the desired functionality.

In one embodiment, only filter and positive air pressure functionality may be required. In this embodiment, the generator unit 3 therefore includes a filter 5 for filtering air, and an impeller 4 for positively pressurising the air. A control unit 6 in this case may be a simple on-off switch. In another embodiment, the control 6, may include a user setting switch enabling the user to set a level for the impeller 4 and therefore, to decrease or increase the air pressure to the mask. A power supply (not shown in Figures), such as a battery, for the impeller and control is also provided.

Embodiments of generator units may include variations of the embodiments described in International Patent Application PCT/AU2010/0000902, by the current applicant.

Figure 2:
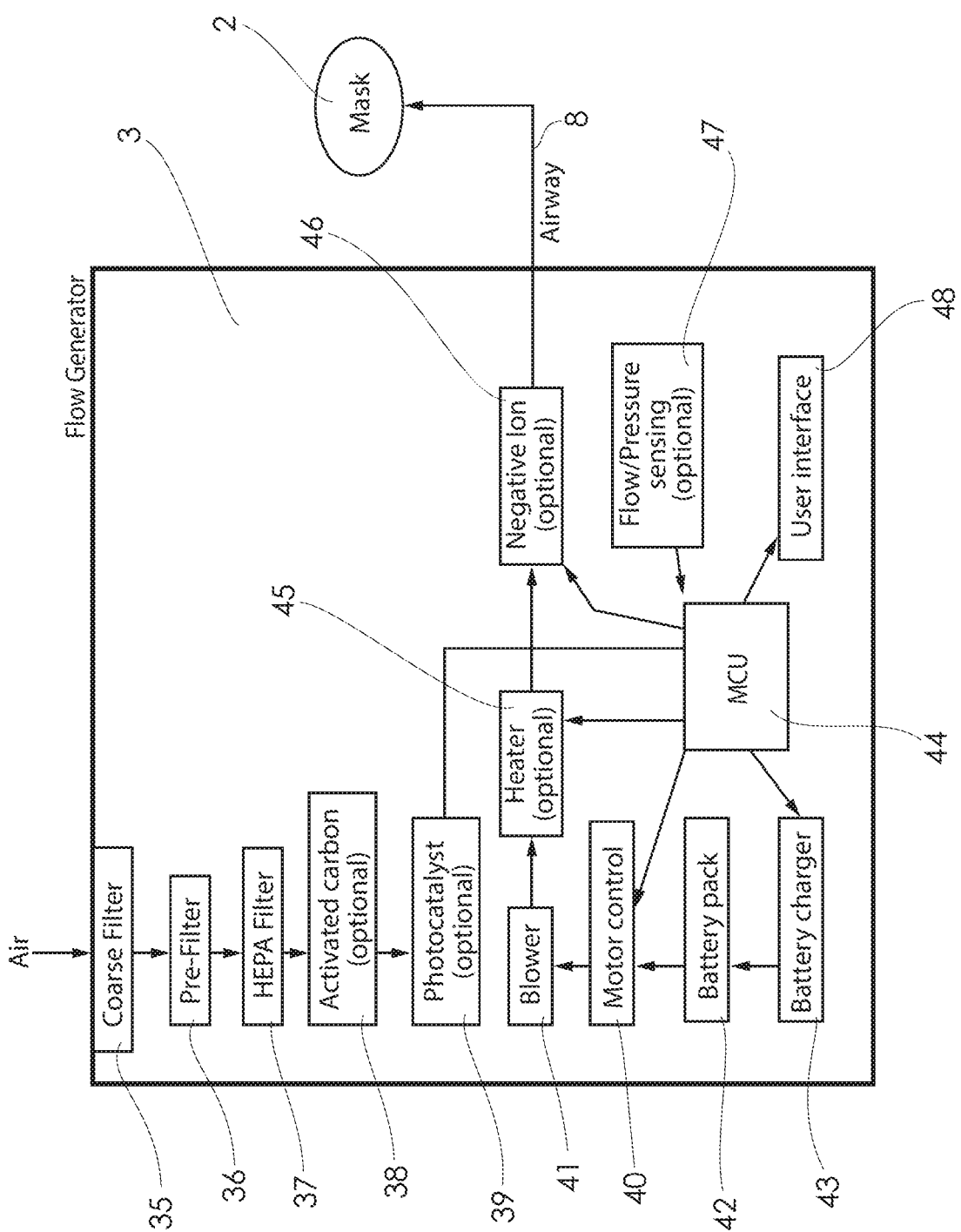
FIG. 2 is a block diagram of an air flow generator and filter unit of a breathing apparatus in accordance with an embodiment of the present invention.

FIG. 2 is a block diagram showing various components that may be utilized in the generator unit of this embodiment of this invention. As discussed above, some of these components are optional, and what components are included will depend upon factors such as required cost and functionality for the unit. A simple unit may merely comprise a filter, control switch and impeller, as discussed above. Other embodiments may have additional components, providing additional functionality, such as shown in FIG. 2.

The filter 5 may comprise a single type of filter or may comprise a plurality of different types of cascaded filter. FIG. 2 illustrates a coarse filter 35, which can remove large particles present in very dusty environments, such as wood cutting workshops. The coarse filter 35 may be low cost synthetic fibre and washable or easily disposable.

Coarse filter 35 is followed by a prefilter 36. The prefilter 36 may be made from a suitable synthetic fibre such as polypropylene, and preferably have an efficiency equal to or better than 90% of the particle size of 5 µm and above.

Prefilter 36 is followed by a HEPA filter 37. The HEPA filter is a particulate filter. An activated carbon filter 38 may also be included and also photocatalytic filter 39. The filter array including all filters 35, 36, 37, 38 and 39 would provide very good filter functionality. In a simple embodiment, such as a simple breathing apparatus arranged for use in an urban environment, a single HEPA filter 37 may suffice.

Different filters 35, 36, 37, 38, 39 can be used separately or together depending upon the required application. The filters may be provided in one or more filter units which may be easily removed for disposal and exchange, or for washing.

The impeller arrangement in the embodiment of FIG. 2 comprises a motor control and a blower 40 and 41 respectively. A battery pack 42 for power supply is provided, and a battery charger 43 for plugging in to an external power supply for charging the battery 43. Controller 6 in this embodiment comprises a micro control unit (MCU) 44.

The generator unit of FIG. 2 comprises a heater 45 which may heat cold air to be provided to the mask 2. In an alternative embodiment a cooler and air conditioner may be provided. Also, in another embodiment, a humidifier may be provided. The breathing apparatus can therefore be adapted for various environments. A cool environment may use a heater, a hot environment may implement a cooler and an air conditioner.

The embodiment of FIG. 2 also comprises a negative ion generator 46, to provide negative ions.

In the embodiment of FIG. 2, sensors 7 are provided, in this embodiment in the form of a flow sensor and/or pressure sensor 47. The flow or pressure sensor may be placed in or close to the airway 8 to sense the pressure. The pressure may be compared with a user pressure setting, in the MCU 44, and the blower 41 may be adjusted to vary the pressure. In an embodiment, the MCU 44 may include a control mechanism to sense the rate of change of air flow or pressure and vary the blower 41 accordingly. When a user starts breathing more rapidly, therefore, the blower 41 may be increase to compensate for the increased air requirement. A description of such a feedback control mechanism is given in applicant's co-pending International (PCT) Patent Application No. PCT/AU2010/0000902, incorporated herein by reference.

A user interface 48 may be provided for inputting user control, such as pressure settings, heater settings, on/off switch and any other control required.

The MCU 44 may be programmable, and various software modules may be utilised to vary the functionality. The MCU may operate on upgradable software or program logic to control the flow rate dependent on user setting, and/or environmental conditions and/or sensor data.

Figure 3:
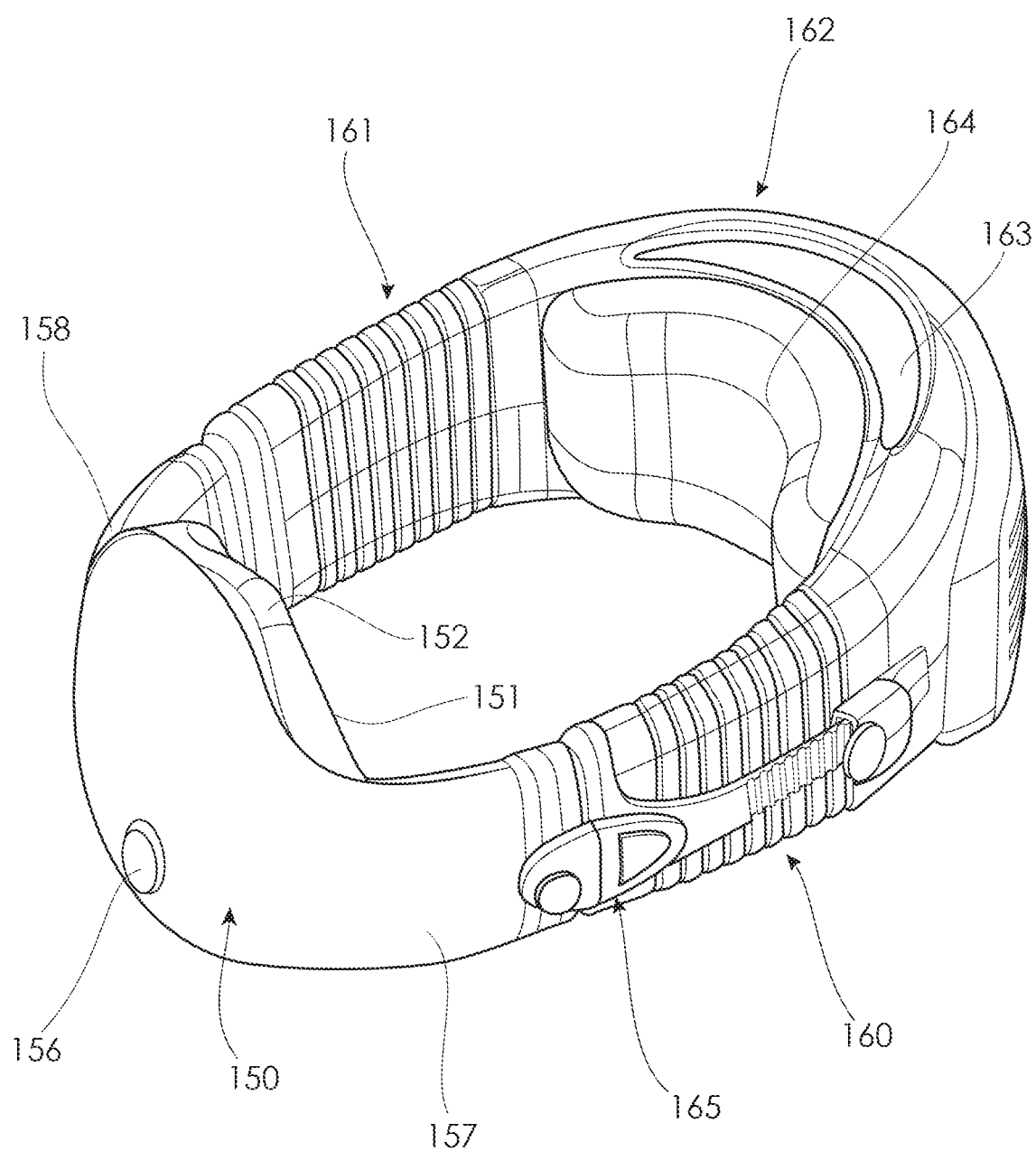
FIG. 3 is a perspective view of a breathing apparatus in accordance with an embodiment of the present invention.

FIG. 3 shows an embodiment of the breathing apparatus in accordance with the present invention. The mask arrangement 150 is connected via airways 160 and 161 (also airways 157 and 158) to a generator unit 162.

The arrangement of FIG. 3 is similar to the PAPR apparatus describe in applicant's earlier patent application PCT/AU2010/000902. It is modified by the mask arrangement 150 (see description of FIG. 6 later on) and may include any of the other modifications (particularly of the generator unit 162) discussed in this specification.

The generator unit 162 is mounted by a neck component 163 which, in use, is worn at the back of a user's neck. A neck pad 164 provides a level of comfort for the user. This may be of soft, flexible material.

Cooperating connector arrangements 165 (an equivalent connector arrangement is on the other side of the apparatus not shown in FIG. 3) operate to connect mask arrangement 150 airway 157 and 158 with airways 160 and 161 leading to the generator unit 162. The airways 160 and 161 essentially form "arms" that join and support the mask arrangement 150 together with the generator unit 162.

Figure 5:
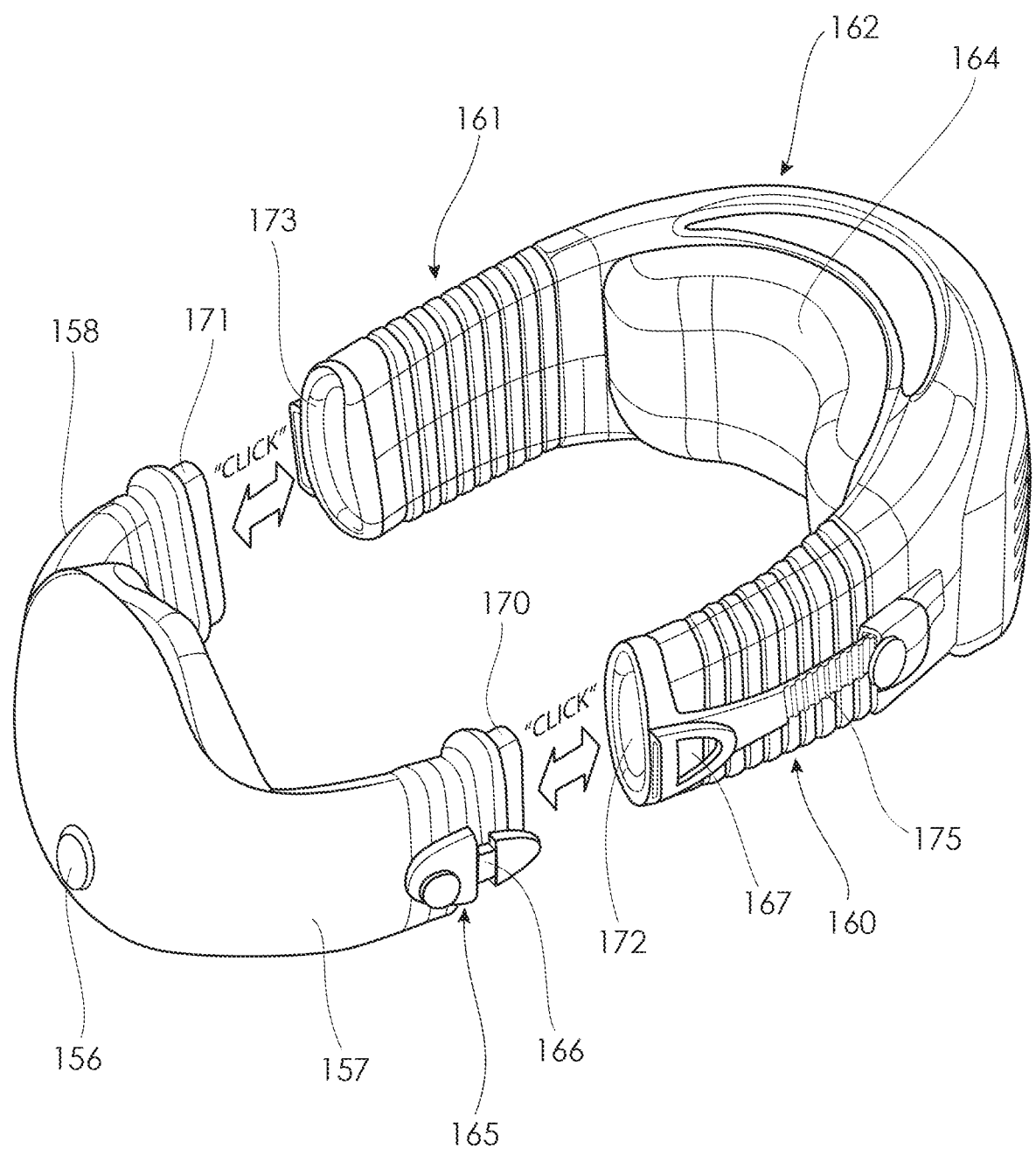
FIG. 5 is a further perspective view of the embodiment of FIG. 3, illustrating the mask arrangement disconnected from the rest of the apparatus.

FIG. 5 shows an exploded view of the breathing apparatus, showing the mask arrangement 150 separated from the generator unit 162. The connector arrangement 165 (see FIG. 5) comprises a mask clip 166 and a mask clip receiver 167 arranged to receive the mask clip 166 and retain it. Airways 157 and 158 have plugs 170 and 171 which engage with corresponding sockets 172 and 173 in the airways 160 and 161 respectively. Airways 160 and 161 are resiliently compressible (i.e. they can extend and compress in order to provide some flexibility of the breathing apparatus about the users neck and face, and also to facilitate a good fit) and a ratchet arrangement 175 (equivalent ratchet arrangement is on the other side of FIG. 5, not shown) allows for adjustment of the length of the airways 160, 161 for comfort and fit.

Figure 4:
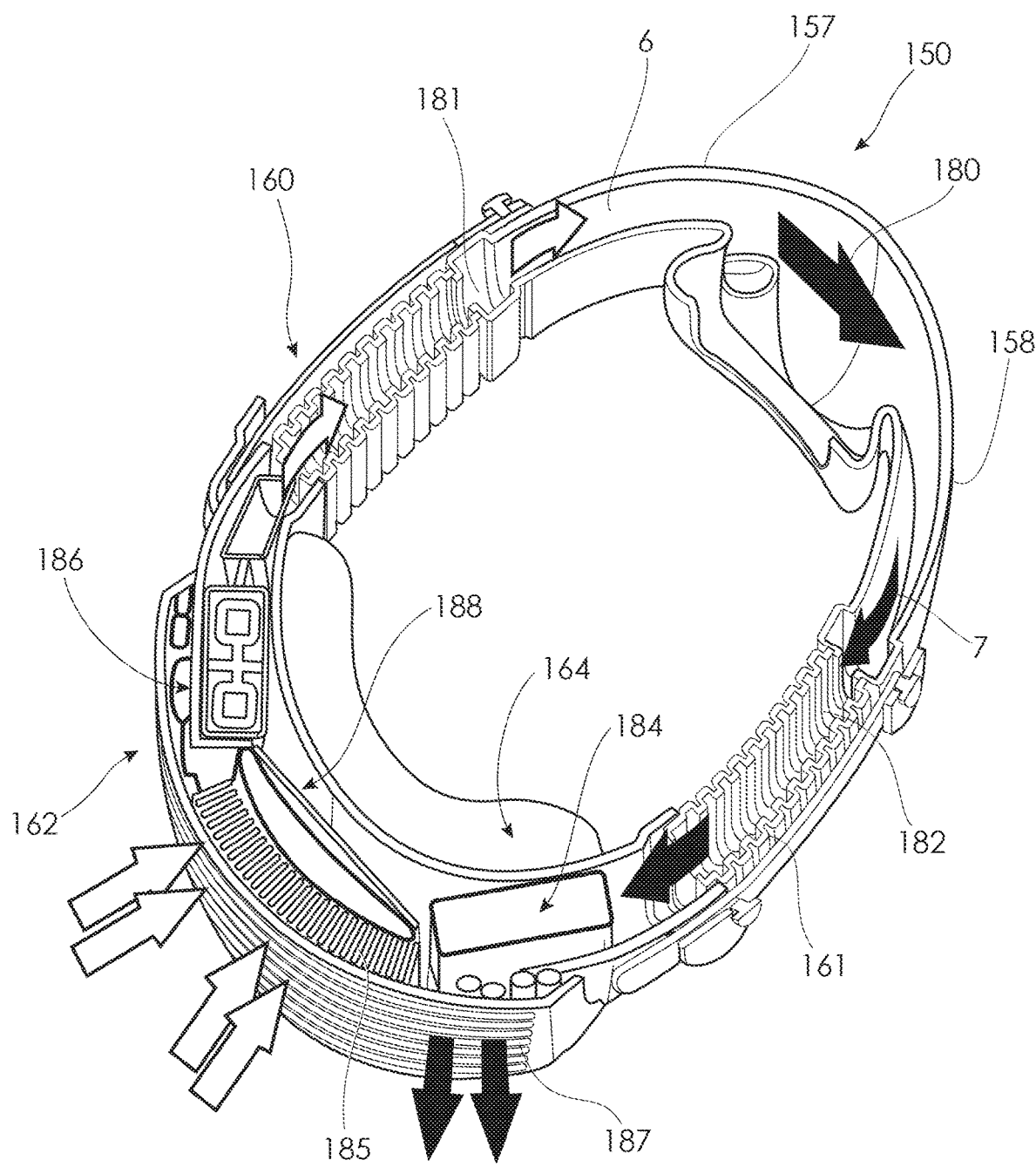
FIG. 4 is a sectional view of the apparatus of FIG. 15, showing internal components.

FIG. 4 shows a sectional view through the apparatus of the embodiment of FIG. 3. A breathing chamber 180 is provided in the space between the face of the user and the shell of the mask 150. The breathing chamber 180 is isolated from the surrounding environment by virtue of the seal about the face of the user. The airways 157, 158, 160, 161, when connected provide passageways 181, 182 for flow of the air from the generator unit 162 to the mask chamber 180 and back to the generator unit 162 for porting into the environment. Direction of airflow is shown in FIG. 4 by the white and black arrows. The black arrows indicate air being exhaled and the white arrows indicate pressurised and filtered air being provided to the mask chamber 180.

The generator unit comprises a filter unit 185 to receive and filter inhaled air. The filter unit 185 may comprise a number of different types of filter as discussed previously, such as pre-filter, HEPA filter and others, depending upon the type of filtering required for the environment in which the breathing apparatus is to be used. An impellor unit 186 pressurises the air and forces it in the direction indicated by the arrows. The exhaled air may be ported via a further filter unit 187, to avoid pathogens from the user, for example, being ported into the environment. A software controlled control unit 188 may control the impellor 186 and other aspects of the breathing apparatus. A power supply 189 in the form of a battery is also provided in the generator unit.

The breathing apparatus may also comprise one or more pressure flow and/or temperature sensors. By monitoring breathing patterns of the user the control unit 188 is able to control the flow rate of the air delivered to the mask chamber 180. The control unit may operate on upgradable software or program logic to control the flow rate dependent on user settings, environmental attributes and/or sensor data.

Figure 46:
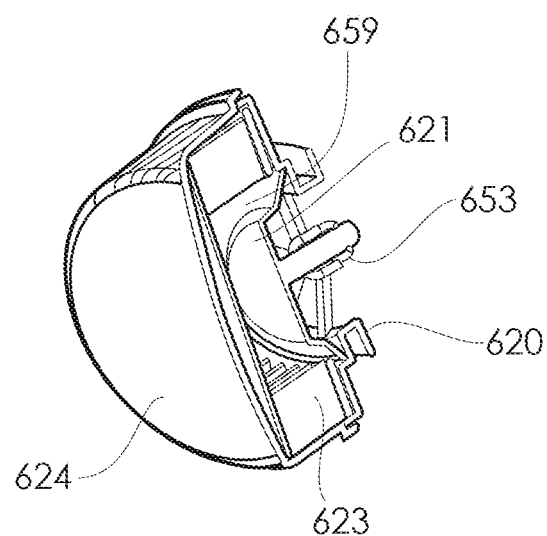
FIG. 46 is a sectional view of the filter of FIG. 49.

The breathing apparatus of this embodiment may include one, more or all of the other components which are shown and described above with reference to FIG. 2. A valve arrangement, such as described with reference to FIGS. 46, 47, 48, may be used as valve 156. An optional communication module consisting of a microphone, voice signal processing/noise cancelling and a Bluetooth module can be implemented in this embodiment (and other embodiments). The purpose is to be able to speak quietly and clearly while wearing the mask. The microphone is ideally located within the neck component 162. Alternatively, it can be fitted inside the mask. A noise cancelling and Bluetooth module is fitted in the neck component 162. Noise from the motor and environmental noise is cancelled and a voice is enhanced. The voice is converted to an audio stream and is transmitted to a suitable Bluetooth enabled device, such as speaker or smartphone nearby, wirelessly. Thus voice communication is made easy without taking off the mask. When wearing a Bluetooth earplug or headphone, the user can make a phone call in a whisper even in a noisy environment. With the Bluetooth module, a smartphone can be used as a remote control device to the respirator (using an "App" for example) and it is also possible to download software, retrieve respirator usage information, alerts, warnings for filter replacement, etc.

Figure 6:
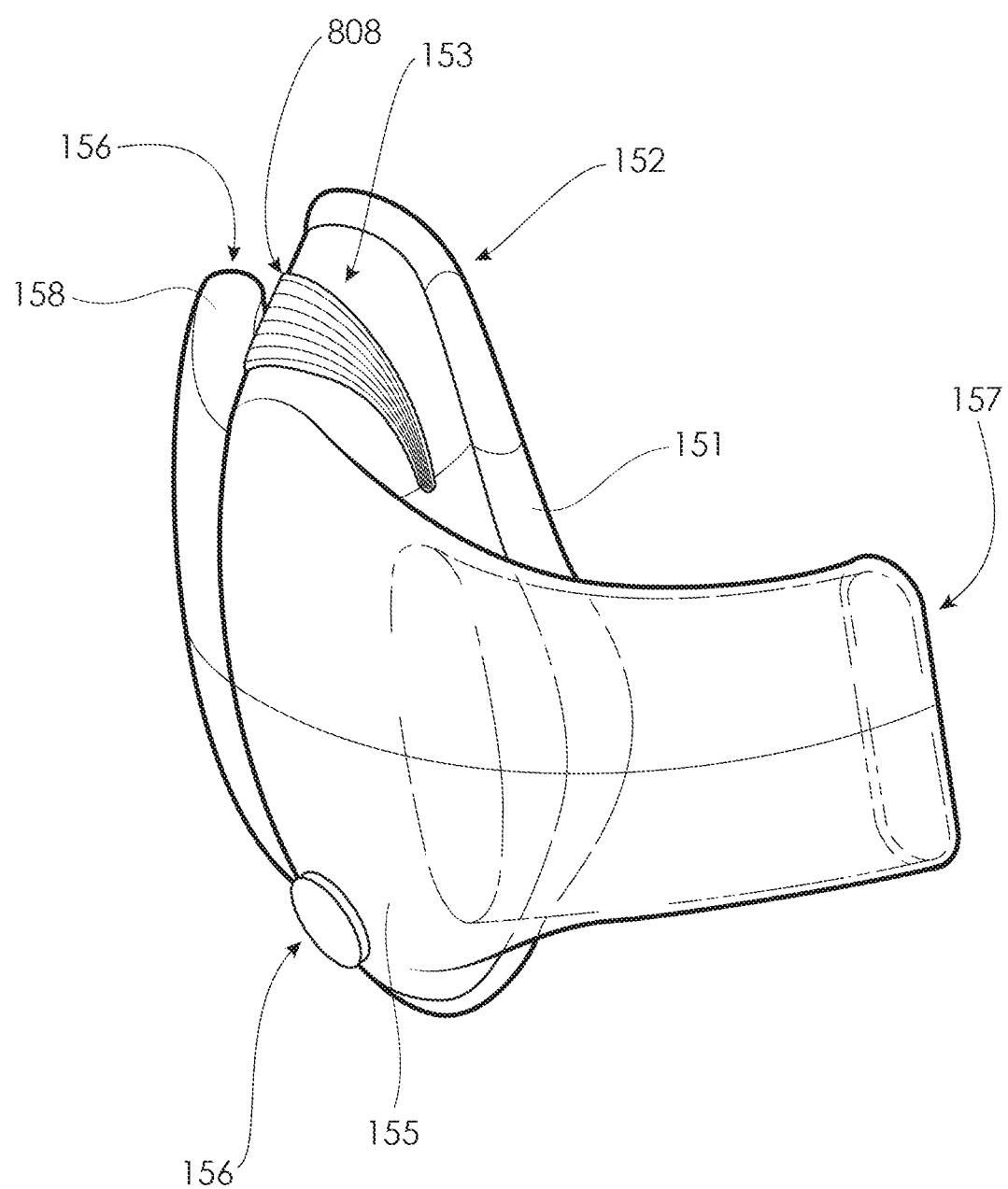
FIG. 6 is a detail view of the mask arrangement of the embodiment of FIGS. 3 to 5.

FIG. 6 is perspective view of a mask arrangement in accordance with an embodiment of the present invention. The mask arrangement of this embodiment comprises mask structural features which facilitate comfort for the user and also effectiveness of the mask. The mask 150 of this embodiment comprises a face contacting cushion 151 which is arranged to surround the periphery of the mask, and, in use, contact the user's face. This cushion 151 may be arranged to be relatively flexible and softer than the rest of the mask and may even be made of different material. A portion 152 of the cushion arranged to contact the upper part of the face and the nose bridge is arranged to be thinner than the rest of the cushion 151 to facilitate comfort.

The top portion 153 of the mask is provided with a flexible bellows arrangement 154 which allows the cushion 153 to flex. Bellows arrangement 154 forms a resilient structural feature of the mask 150, which again improves comfort and conformity to the user's face in use.

A lower portion of the mask 155 mounts a valve 156, which ports air from the mask 150 when the pressure inside the mask 150 exceeds a predetermined level.

Airways 157 and 158 are, in this embodiment, integral with the mask 150. Airway 157 conveys pressurised and filtered air from the generator unit 162 to the mask and airway 158 conveys exhaled air from the mask back to the generator unit where it may be filtered before being ported.

The features associated with the mask, such as the resilient structural feature and the thinner wall section are not limited to a mask with an integral airway such as shown in FIG. 6. The airway may be separate and may be of any of the type shown above and in the following described embodiments, for example, or any other type.

FIGS. 7 through 13 illustrate various forms of breathing apparatus in accordance with embodiments of the present invention.

Figure 7:
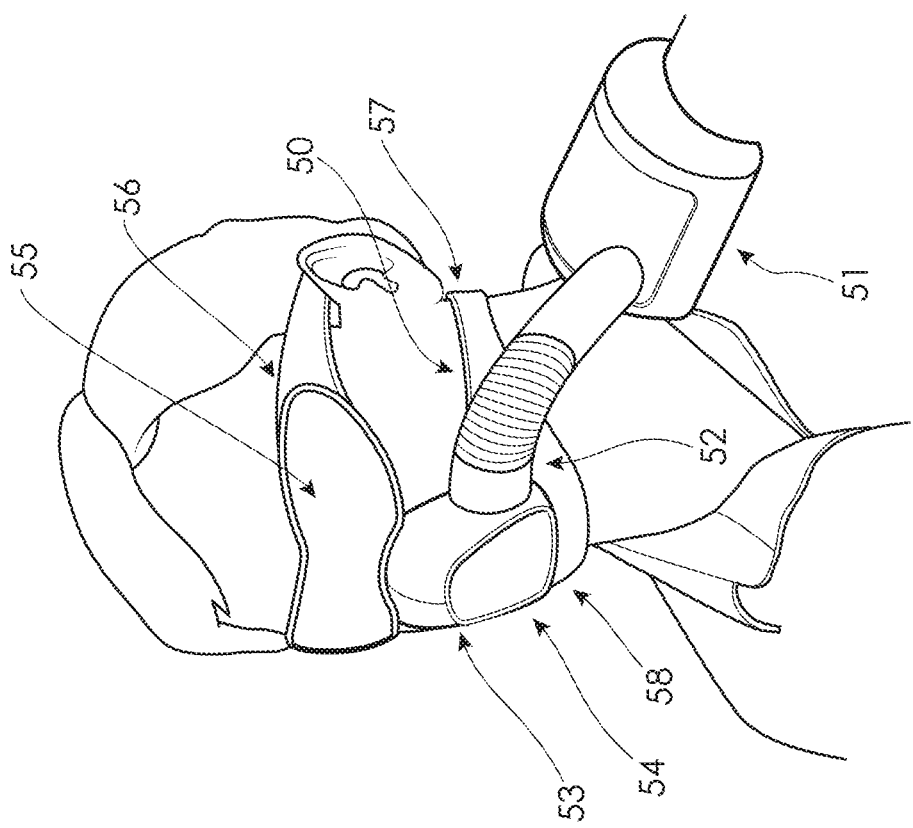
FIG. 7 illustrates a further embodiment of the present invention.

Referring to FIG. 7, a PAPR in accordance with a further embodiment of the present invention is illustrated. The PAPR 50 comprises a generator unit 51, an airway 52 and a combined mask and eye protector arrangement 53. The generator unit 51 and airway 52 may comprise components similar to those discussed above in relation to the previous embodiments, and no further description will be given here. The airway is a single airway 52 from the generator unit 51 to the mask 53. There is no return airway as in the embodiment of FIG. 3. The generator unit 51 is mounted on the shoulder.

The mask and eye protector arrangement 53 comprises a mouth and nose mask 54 and an eye protector 55 in the form of a pair of goggles secured by a strap 56 passing over the ears and behind the neck in use. Alternatively, the strap 56 may comprise a pair of supports which merely pass over the ears.

In this embodiment, the goggles 55 are secured to the mask 54. And may be able to be separated from the mask 54 for cleaning. The mask 54 is secured by a strap 57 arranged to pass behind the neck. The mask 54 is, in this embodiment, not a disposable mask, but a mask of washable material, such as silicone. A portion 58 of the mask is relatively flat and rigid and may carry sound waves, so that the user can speak through it.

In this embodiment, the generator unit 51 is worn on the shoulder, and there is a single airway 52 for providing filtered and pressurised air to the mask 54. Exhaled air, may escape the mask 54 via filter material and/or an exhaust valve (not shown).

Figure 8:
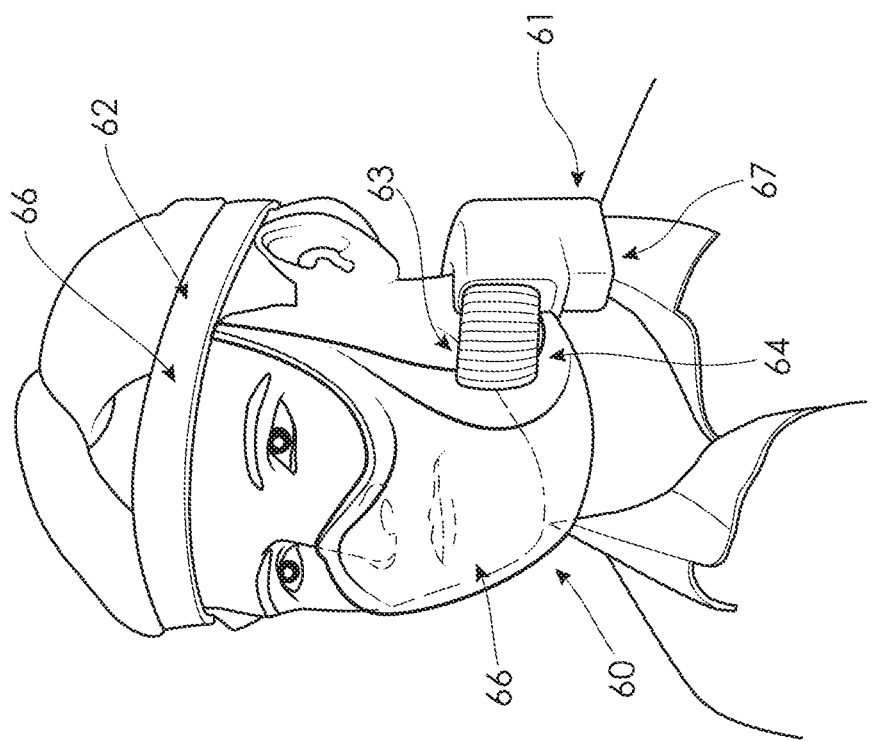
FIG. 8 is an illustration of a further embodiment of the present invention.

A further embodiment is shown in FIG. 8. The PAPR 60 of this embodiment comprises a generator unit 61 which, in this embodiment, comprises a neck mounted housing which extends around the back of the user's neck and has a rest portion 62 which rests on the user's shoulders. The airway 63 in this embodiment comprises a pair of airway limbs 64, only one of which is shown in the Figure, the other airway 64 passes around the other side of the neck and joins the generator unit 61 on the opposite side of the user (not shown). The structure of the airway 63 is generally similar to a structure of the airway of the embodiment of FIGS. 3 to 5.

The PAPR 60 also comprises a mask, which in this embodiment is covered by a decorative mask cover 65. Decorative mask cover 65 may comprise material which is attached to the unit 61 and also to a headband 66 at attachment points 67. The cover 65 in this embodiment is intended to provide aesthetic appeal. The decorative mask cover 65 also provides protection from the environment for the face. This is very important, particularly in a number of countries where it is felt to be important to shield the face from the environment. For example, the decorative cover may be effective in shielding the face from the effect of UV radiation.

In use, pressurised and filtered air is provided by the airway 64 into a mask (not shown) underneath the cover 65. On the other side of the user (not shown) the second limb 64 of the airway transports exhaled air away from the mask and back to the unit 64. The exhaled air is ported from the unit 61. The unit 61 in this embodiment includes an exhaled air filter, which filters the exhaled air, as well as including filters for filtering air taken in to the apparatus. Having an exhaled air filter in this fashion means that any viruses or bacteria that the user may be carrying will not be ported into the environment, or at least porting of such pathogens into the environment will be reduced.

Figure 9:
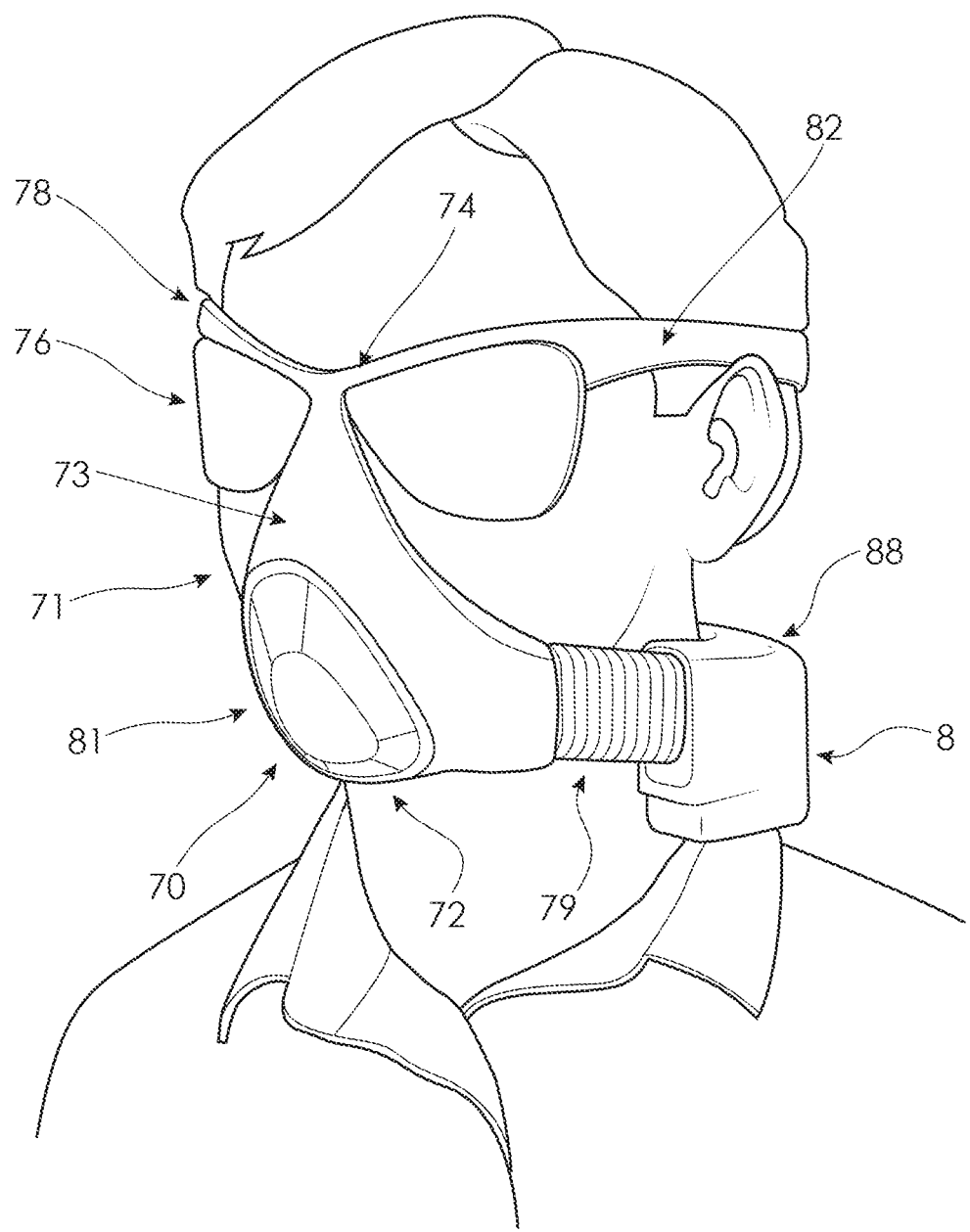
FIG. 9 is an illustration of a further embodiment of the present invention.

FIG. 9 illustrates yet another embodiment of the invention. The breathing apparatus 70 of this embodiment comprises a mask and glasses unit 71. The mask 72 comprises a nose bridge 73 which extends upwardly to integral glasses support 74, which support protective lenses 75, 76. The support 74 comprises a pair of arms 77, 78 which extend behind the ears of the user to support the arrangement. The arms 77, 78 may be rigid plastics or, in an alternative embodiment, may comprise a flexible strap which passes around the back of the head of the user. The breathing apparatus 70 also comprises an airway 79 and a generator unit 80, which is similar to the generator unit and airway of the embodiment of FIG. 8. The mask 72 includes a flat, relatively rigid portion 81 which allows sound to carry.

Figure 10:
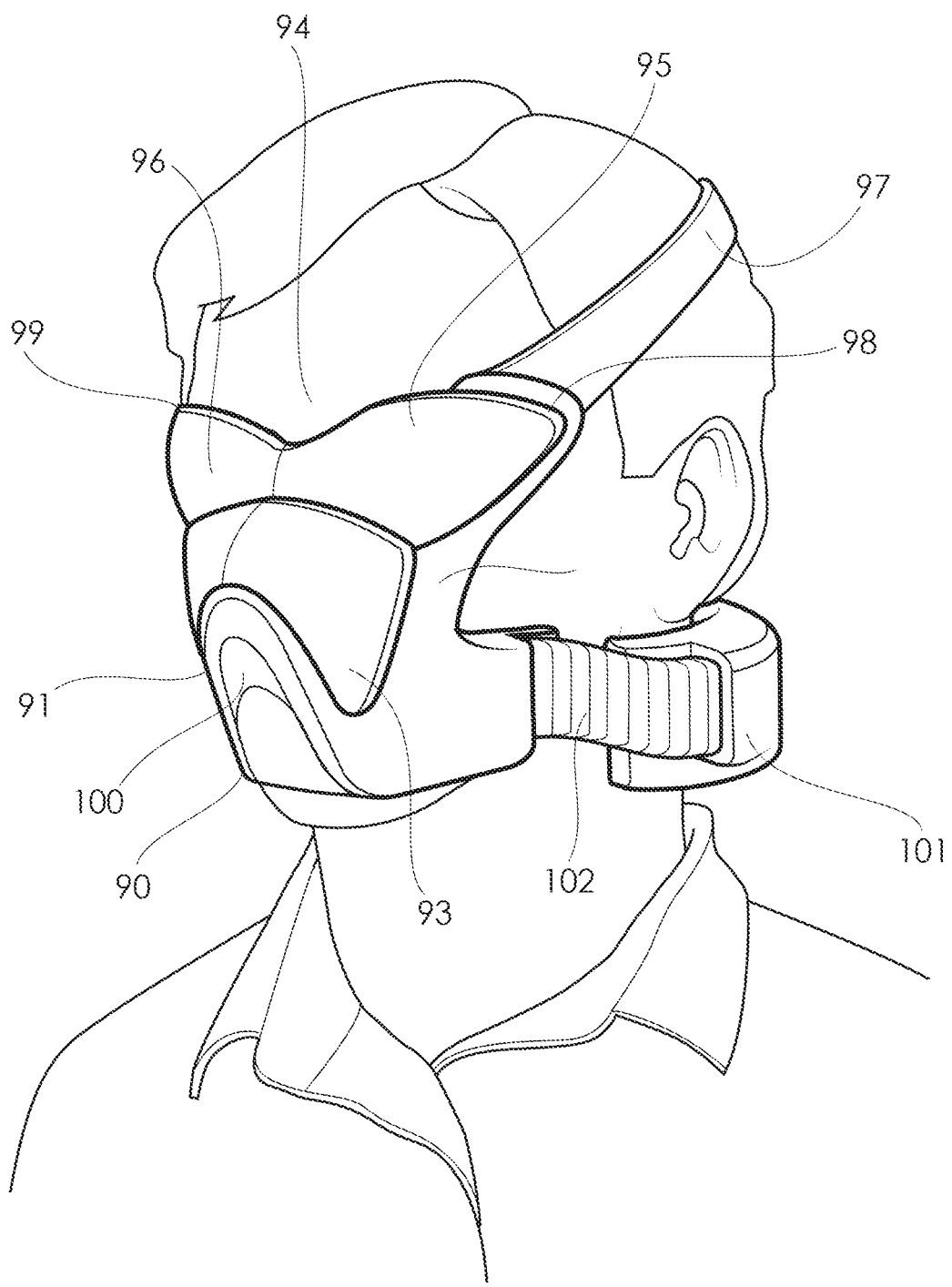
FIG. 10 is an illustration of a further embodiment of the present invention.

FIG. 10 illustrates a further embodiment of a breathing apparatus in accordance with the present invention.

The breathing apparatus 90 of this embodiment comprises a mask arrangement 91 which includes a frame 92 which supports the mask 93 and also supports eyewear 94, comprising a pair of integral lenses 95 and 96. A headband 97 is attached to the frame 92 at top portions 98 and 99. The headband 97 extends over the back of the head of the user in use to secure the mask arrangement about the face of the user. The frame 92 forms a full face mask covering the nose and mouth of the user and supporting the eyewear 94. The mask 92 has a flat relatively rigid portion 100 for carrying sound. The frame 92 may be relatively flexible so as to conform with the contours of the user's face.

The generator unit 101 and airway 102 are similar in form to the embodiment of FIG. 8.

Figure 11:
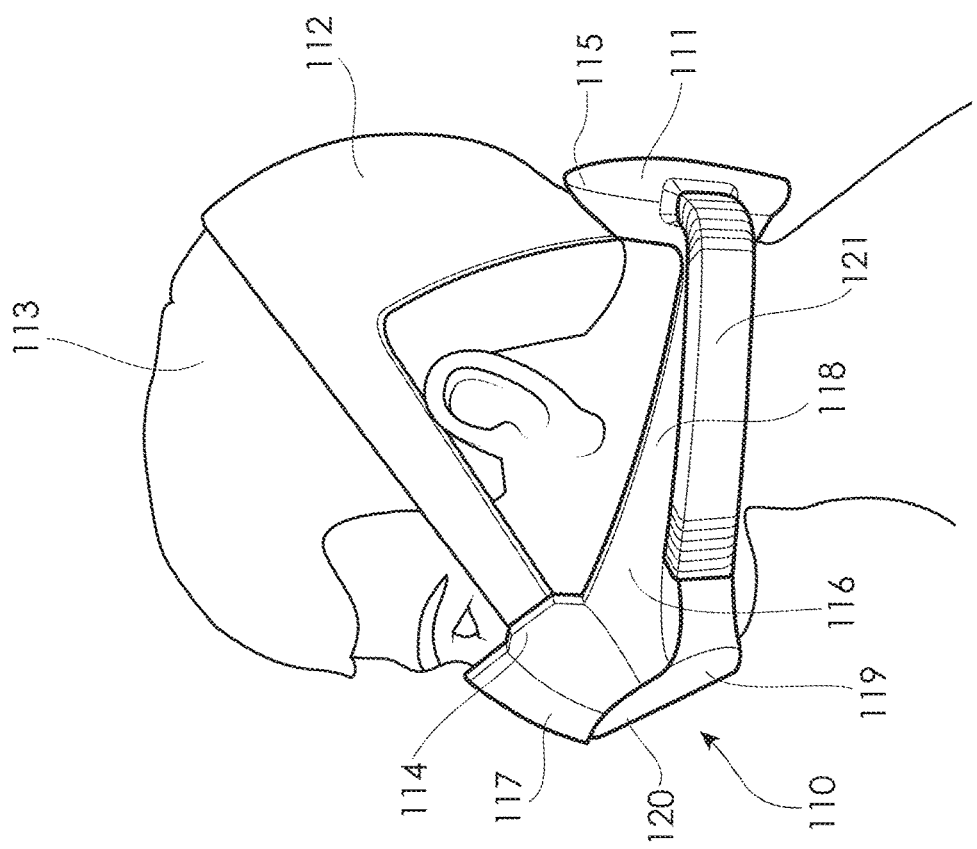
FIG. 11 is an illustration of a further embodiment of the present invention.

FIG. 11 is a side view of further embodiment of a breathing apparatus 110 in accordance with the present invention. In this embodiment the generator unit 111 is arranged to sit at the back of the neck of the user in use. A head strap 112 is connected to a top portion 113 of the generator unit 111. The head strap 112 reaches up from the back of the neck to the back of the head and is integral with a mask strap 113 which passes round either side of the head and is attached to side portions 114 (there is another side portion 114 on the other side of the user's face not shown in this drawing) of the mask arrangement 110. The mask strap 113 and head strap 112 work together to support the entire breathing apparatus 110.

The mask arrangement 120 comprises a framework 116 which forms a top portion 117 of the mask and has side portions 118 (other side portion 118 on the other side of the head, not shown in this drawing) which connects the top portion 117 of the mask arrangement 110 and the generator unit 111. The framework, at least the portions 118, are of relatively flexible material so that the entire apparatus 110 may be passed over the head of the user and secured in position.

The mask arrangement 120 also comprises a relatively rigid front portion 119 which allows sound to carry. An airway 121 connects the generator unit 111 to a chamber about the mouth and nose of the user formed by the mask arrangement 120. An equivalent airway (not shown) is positioned on the other side of the head to receive exhaled air, in a similar fashion to the apparatus of FIG. 8.

Figure 12:
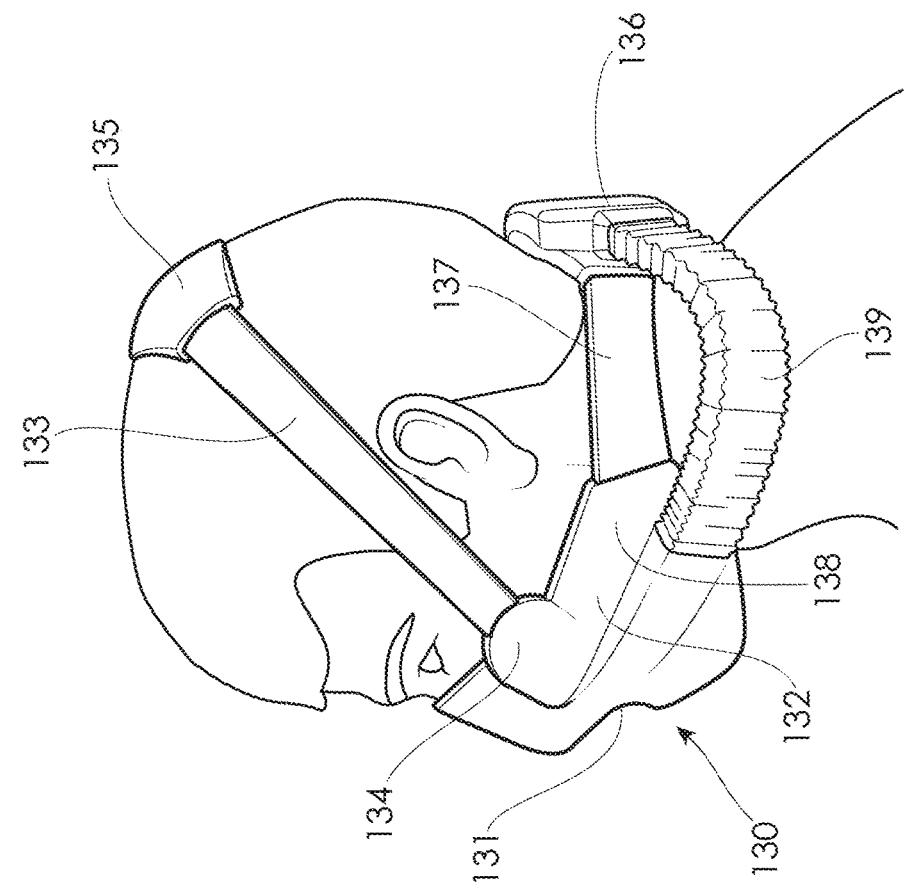
FIG. 12 is an illustration of a further embodiment of the present invention.

FIG. 12 illustrates yet a further embodiment of the present invention. The breathing apparatus 130 of this arrangement has a mask arrangement 131 which comprises a full face mask 132 which extends over the nose and over the chin. A head strap 133 is attached to top portions 134 of the mask arrangement (the other top portion 134 is on the other side of the head, not shown in this drawing), and extends over the back of the head to secure the arrangement. A pad 135 is attached to the head strap 133 at the back of the head.

The breathing apparatus includes a generator unit 136 which sits at the back of the head and is secured by elasticated straps 137 (a strap 137 is also on the other side of the head, not shown in this drawing) which are attached to the mask arrangement 130 at side portions 138 (other side portion 138 on the other side of the head, not shown in this drawing). Airways 139 (other airway on the other side of the head) connect the mask 132 with the generator unit 136.

Figure 13:
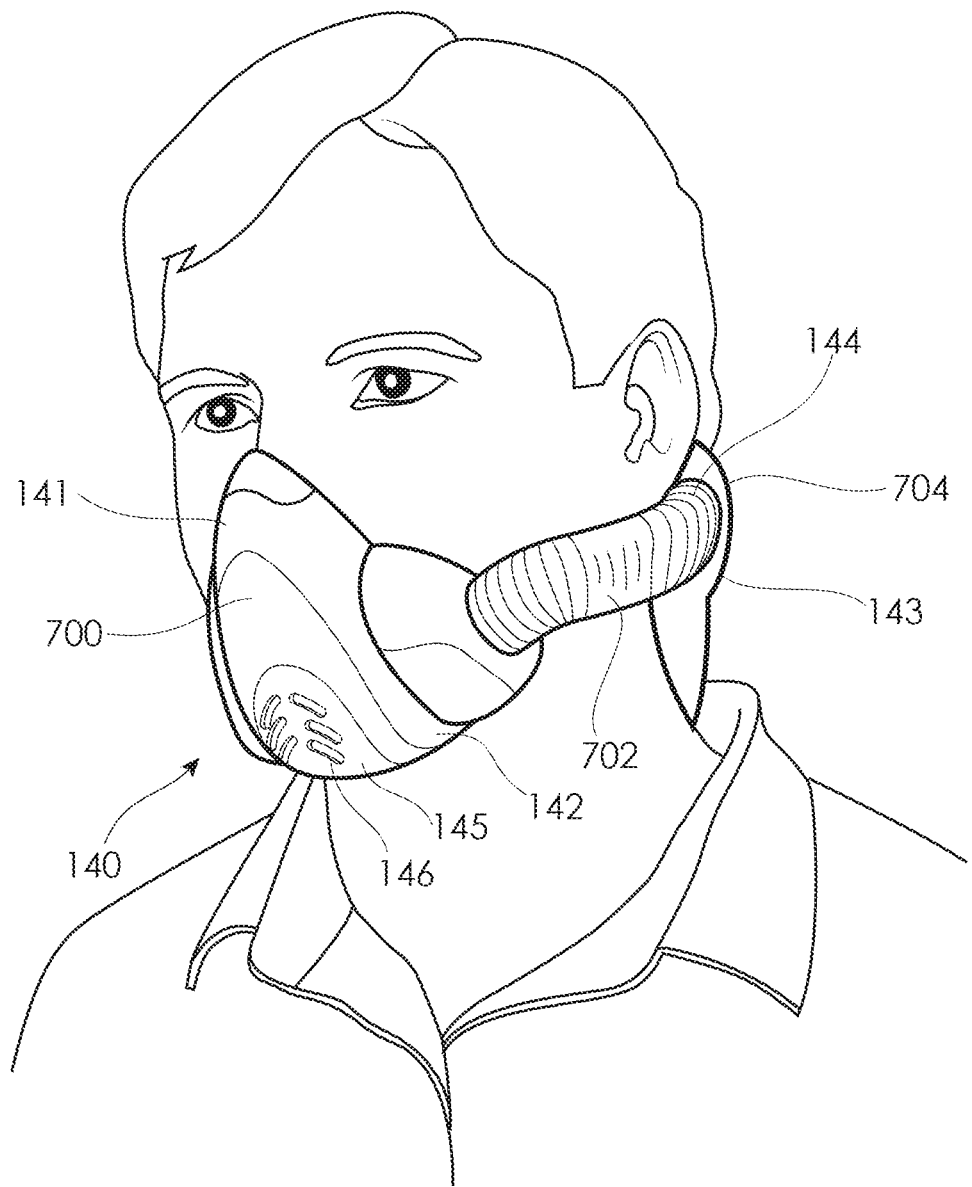
FIG. 13 is an illustration of a further embodiment of the present invention.

A further embodiment of a breathing apparatus is shown in FIG. 13. The breathing apparatus 140 in this embodiment comprises a mask arrangement 141 comprising a mask 142 which extends from the bridge of the nose to underneath the chin of a user. The apparatus 140 includes a behind neck mounted generator unit 143 and airways 144 from both sides of the head (airway on the other side is not shown in this drawing).

Vent arrangement 145 is provided at the front of the mask. The vent arrangement comprises holes 146 in the mask material and filter material under those holes, filtering exhaled air.

In this embodiment, filtered and pressurised air is provided to the mask arrangement 140 via the airway 144 and exhaled air returns to the generator unit 143 via other airway (not shown) on the other side of the head and is ported via a filter for the exhaled air. If the pressure in the mask rises, some exhaled air may be ported via the vents 146.

Figure 14:
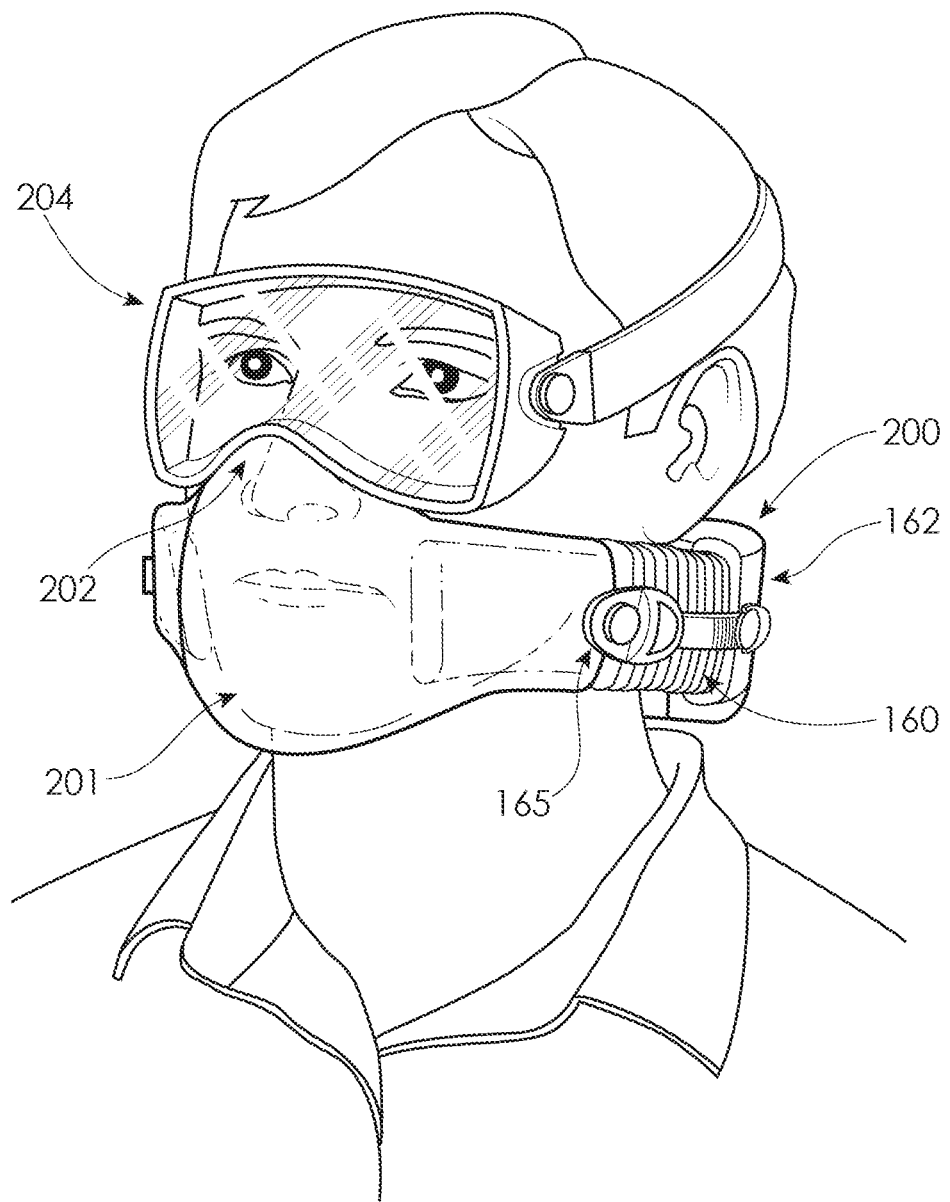
FIG. 14 is an illustration of a further embodiment of the present invention.

FIG. 14 illustrates a further embodiment of a breathing apparatus in accordance with the present invention, generally designated by reference numeral 200. The breathing apparatus 200 is a variation on the embodiment of FIGS. 3 to 5. The breathing apparatus 200 comprises a generator unit 162 and airways 160 and 161 (not shown) which are the same as the embodiment of FIGS. 3 to 5. No further description will be given of these components.

The breathing apparatus 200 comprises a mask arrangement 201 which comprises a low profile nose portion 202. The low profile nose portion 202 is arranged to encompass the nasal orifices of a user, without covering the upper portion of the nose of the user. This allows the user to wear relatively large eye gear such as goggles 204, without the goggles 204 being interfered with by the low profile mask.

The mask arrangement 201, with low profile nose portion 202, may be used with variations which do not include the generator unit mounted at the back of the neck. For example, the generator unit may be mounted elsewhere and attached to the mask arrangement 201 via different types of airways, such as those described above.

FIGS. 15 and 16 illustrate a further embodiment of the present invention. The breathing apparatus 210 of this embodiment comprises a neck mounted generator unit 162 with airways 160 and 161. These airways and the generator unit 162 have the same components as the embodiments of FIGS. 3 and 5, and no further description will be given.

The mask arrangement 211 of this breathing apparatus 210, however, is a hybrid mask arrangement. It comprises a mouth covering portion 212 and nasal plugs 213, 214 which are arranged to engage with the nasal passageways of the user.

In more detail, the mouth portion 212 comprises a cushion 215 which is arranged to surround the mouth of the user, and the mask arrangement 211 forms a breathing chamber 216 about the mouth of the user. Airways 217, 218 communicate with the chamber 216 and also with the airways 160, 161 in the neck portion of the breathing apparatus 210.

The nasal plugs 123, 124 have passageways 219, 220 which communicate with the chamber 216. Nasal plugs 219, 220 sit in the nostrils, and the user can therefore breath the filtered and pressurised air through the nasal plugs 213, 214, as well as via the mouth and mask chamber 216.

The nasal shield portion 221 of the mask arrangement 211 extends over the nasal plugs 213, 214, to shield them and also extends over the bottom part of the user's nose in use.

This hybrid mask arrangement 211 results in a low profile mask with a low profile shield part 221 which also allows goggles and other heavy eyewear to be worn with the breathing apparatus 210.

The mouth cushion 215 may be formed from relatively soft, flexible material, such as silicone, for comfort.

As with other embodiments, the mask arrangement 211 is not limited to use with a neck component mounted generator 162, and the generator unit may be mounted elsewhere and different airways may be used with a mask arrangements similar to or the same as 211.

A variation of the embodiment of FIG. 15 and FIG. 16 comprises a mask arrangement which does not include the nose plug shield 221. In this embodiment, the nose plugs merely extend from the top of the mask portion 212 to the nose of the user, and are unshielded.

FIGS. 17 and 18 illustrate a further embodiment of a breathing apparatus in accordance with the present invention, generally designated by reference numeral 230. This embodiment includes a neck mounted generator unit 232. An airway 232 from the generator unit 231 attaches to an airways chassis 233. Note that an equivalent airway 232 is provided on the other side of the user that cannot be seen in this drawing. The airway chassis 233 is a relatively rigid component that passes around the face of the user and connects to airways 232, so that there is air passage through to the mask arrangement 235 from the generator unit 231.

In this embodiment, the mask 235 covers the nose orifices only of the user and allows the users mouth to be free, so that they can communicate for example.

FIG. 18 shows a sectional view of the mask 235 showing a chamber 236 formed by the mask via which the pressurised and filtered air reaches the nasal passageways of the user.

The chassis 233 is engaged to the mask body 235 as shown. A resilient cushion 237 is formed at the top part of the mask 235 to cushion against the nose bridge of the user and against the face. A second cushion portion 238 is formed to cushion against the upper lip of the user.

This embodiment is advantageous in that a user of the mask 235 may continue to speak, eat or drink, while still receiving filtered and pressured air via the nasal passageways.

This nose mask arrangement 235 and air chassis 233 embodiment may be used (on adaption) with any of the generator units described above, or any other generator unit, whether placed behind the neck or elsewhere about the user.

The relatively rigid chassis 233 operates in this embodiment to support the mask 235 against the face of the user.

FIGS. 19 and 20 illustrate a further embodiment of a breathing apparatus in accordance with the present invention, designated generally by reference numeral 240.

The breathing apparatus 240 comprises a generator unit 162 and flexible air ducts 160 which are the same as the arrangement of FIGS. 15 to 16. No further description will be given of these components.

The mask arrangement 241 of this embodiment comprises a mask 242 which is arranged to cover only the nose openings of the user. In operation, the mouth of the user is uncovered. The mask arrangement also comprises airways 243, 244 which engage with airways 160 and define conduits which can convey air to and from a mask chamber 245 defined by the mask 242. The mask 242 comprises face engaging cushions 246 (nose cushion) and 247 (upper lip cushion) to engage the face of the user. These cushions may be made of relatively soft material, such as soft silicone.

The mask arrangement 241 also comprises a visor 250 which is connected to the mask 242. In this embodiment a nose piece 251 of the visor is connected to a slot extending in the mask 242. The nose piece 252 may be able to be disengaged from the slot to remove the visor 250. In another embodiment the nose piece 251 may be permanently secured to the mask 241 or may be integral with it. The visor 250 in this embodiment comprises protective lenses 254, 255. A strap 256 is attached to the visor 250 and extends around the back of the head to secure the visor 250.

An optional communications component 260 is provided with this embodiment. The communication component 260 engages with a slot 261 on the lower part of the mask 241 and extends downwardly from the mask so that a microphone or the like 263 is positioned proximate the mouth of the user. An appropriate wireless link may be provided e.g. Bluetooth™ for linking to communications.

The user can advantageously communicate as their mouth is free, including communicating via a coms link provided in the mask via item 260.

The mask 241 also includes an extending portion 265 which extends downwardly from the mask to partially cover the mouth.

Figure 21:
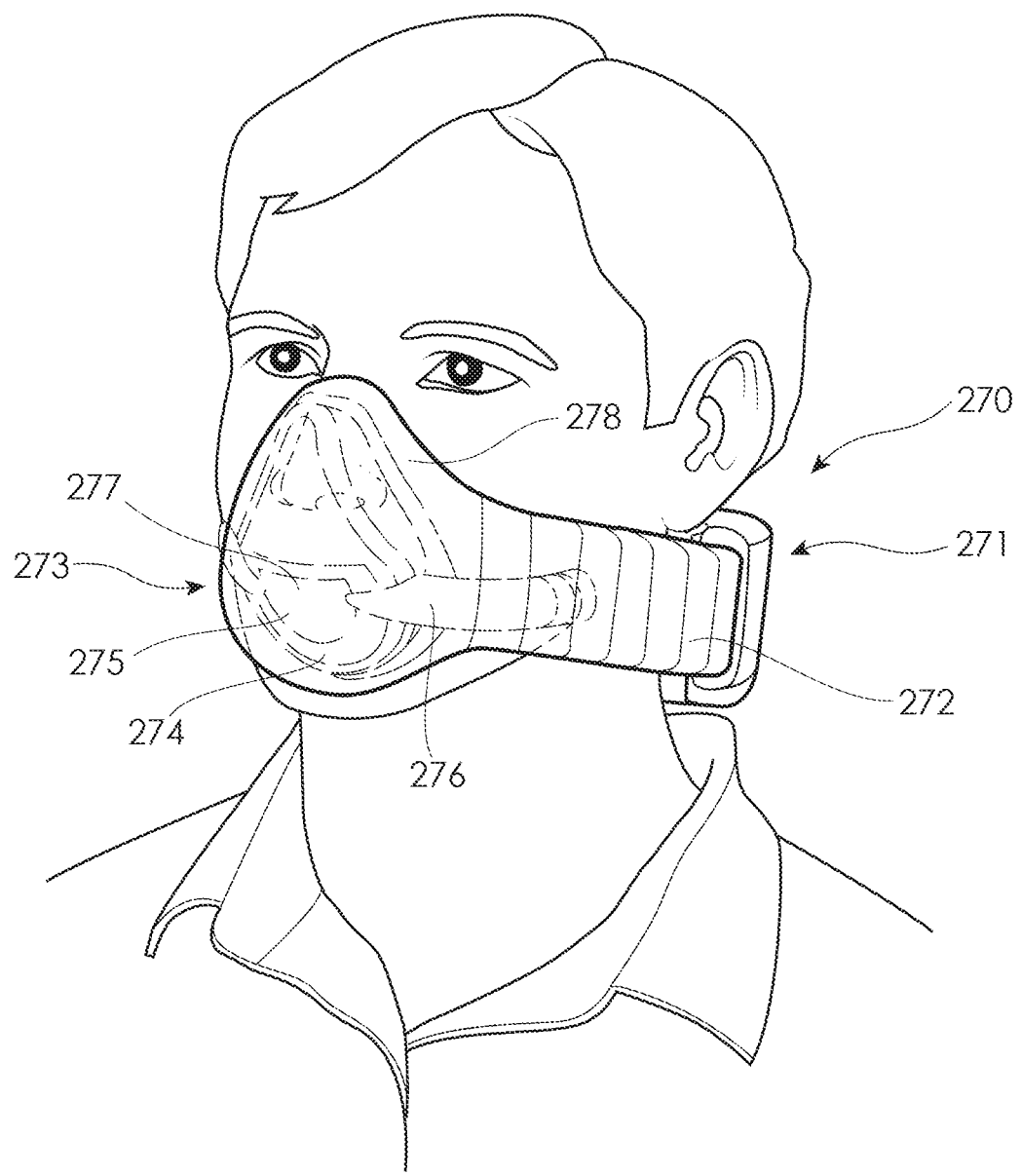
FIG. 21 is an illustration of a further embodiment of the present invention.

FIG. 21 illustrates yet a further embodiment of a breathing apparatus, generally designated by reference numeral 270. A breathing apparatus 270 comprises a neck component mounted generator unit 271 which is connected by airways 272 which are integral with a mask arrangement 273. Another airway 272 extends on the other side of the user, but is not shown in this drawing.

The mask arrangement 273 in this embodiment comprises a relatively thin layer of silicone 274 laid over and supported by a polycarbonate chassis 275. The chassis comprises a support frame 276 which extend into the airway 272 of the breathing apparatus (see FIG. 21A which shows the support frame 276 separate from the mask arrangement. It also comprises a central supporting member 277 which forms a curved plate supporting the thin silicone layer 274. This is clearly shown in FIGS. 21b and 21C. In FIG. 21b, the silicone layer 274 has been cut away in the area of the supporting member 277 apart from at the edges 277a which are sealed to the supporting member 277. Because the supporting member 277 is quite rigid, it supports the user speaking through the mask at this point. In FIG. 21C, the silicone layer has not been cut above the supporting member 277, but this will still be rigid enough to support speech. The supporting member supports a silicone skin 274 which may be relatively thin and flexible. The polycarbonate chassis may be manufactured by three dimensional printing. The airways 272 may also be manufactured in this way and the airways 272 may be integral with the chassis 275, forming "arms" which extend backwards from the mask and connect the generator unit. The silicone 274 may also comprise a silicone cushion 278 about the mouth and nose of the user, for comfort.

The silicone layer 274 may be relatively thin compared with the mask of the preceding embodiment and may include one or more relatively rigid layers to enable transmission of sound when a user speaks. The thin silicone also has the advantage of lighter weight.

Figure 22:
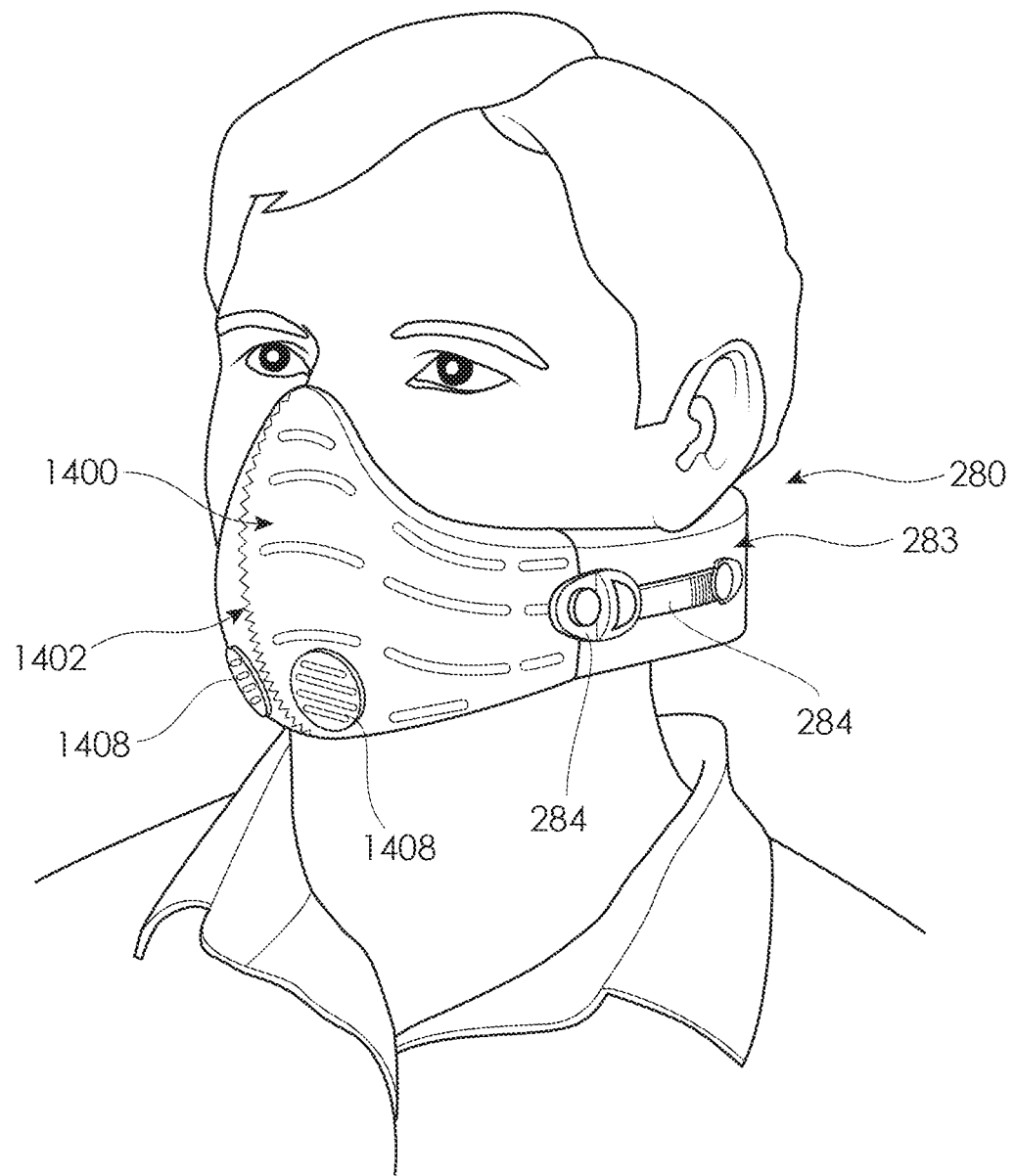
FIG. 22 is an illustration of a further embodiment of the present invention.
Figure 23:
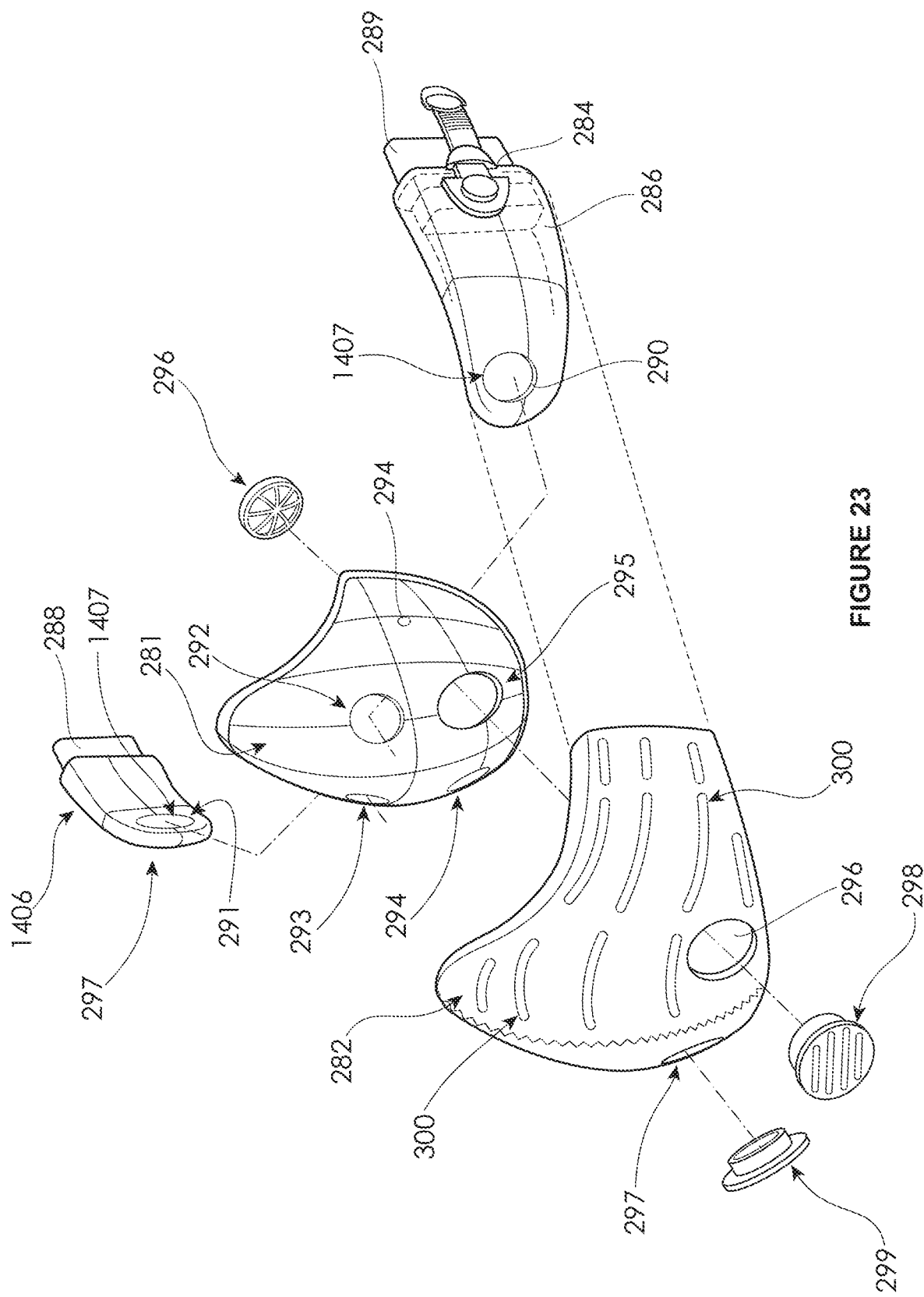
FIG. 23 is an exploded view of parts of the embodiment of FIG. 22.
Figure 24:
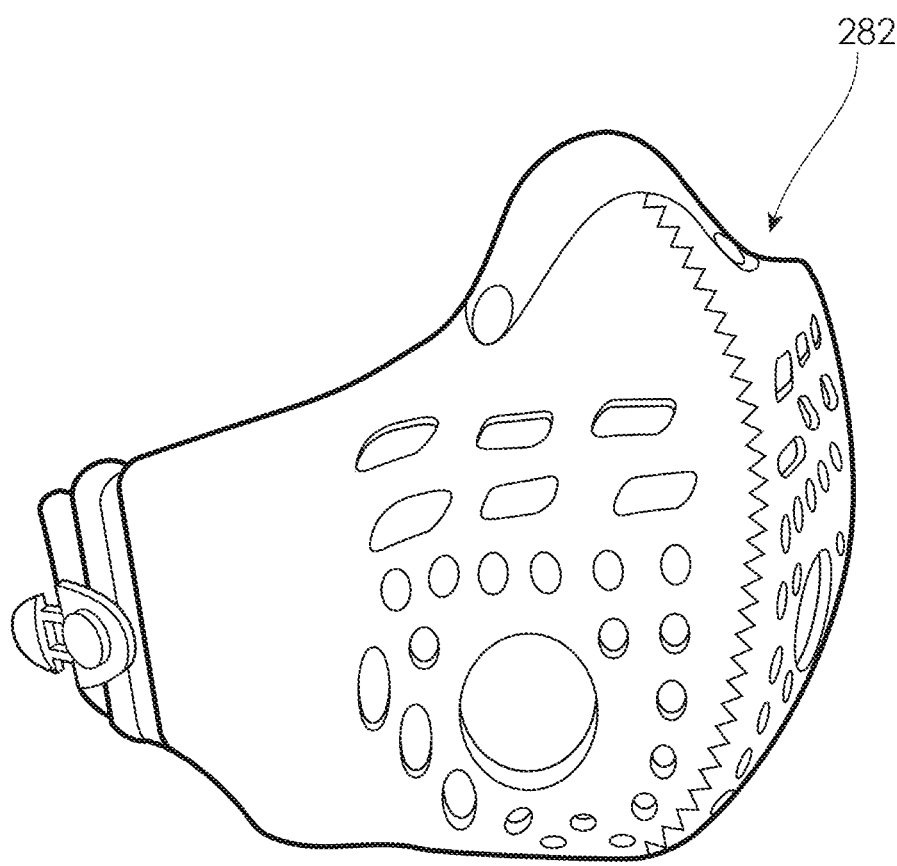
FIG. 24 is a representation of a mask cover part of the embodiment of FIG. 23.

Referring to FIG. 22 through 24, a composite mask apparatus 280 is illustrated, which includes a mask 281 and a decorative cover 282 for the mask. The breathing apparatus 280 includes a neck component 283 which is similar in form and function to the generator unit of FIGS. 3 to 5. Fastening means, in the form of clips 284 and 285 attach airway component 286, 287 to airways for the generator unit 283. The airway components 286, 287 include plugs 288, 289 which cooperate with corresponding sockets (not shown) in the generator unit 283 airways. Ports 290 are formed at the end of airways 286, 287 distal from the generator unit 283. These ports cooperate with orifices 292, 293 in a inner silicone mask 281.

Note that, in an alternative embodiment, the mask may be of other material than silicone or rubber, and may be of porous filter material.

The inner mask 281 also comprises vent holes 294, 295 which are arranged to receive exhaust valves 298, 299.

The outer cover 282 comprises ports 296, 297 which correspond to exhaust ports 294, 295 when the outer cover 282 is placed in position over the mask. Exhaust valves 298, 299 fit into ports 296, 297. They also assist in securing the outer cover 282 to the mask 281. In an alternative embodiment, components 298 and 299 may not be exhaust valves, but may merely be plugs, sealing exhaust ports 295, 294.

The cover 282 also comprises slots 300 in the cover which may be for decorative purposes, which may also allow venting of air where the mask 281 is of porous material.

The inner mask 281 is shaped to cover the mouth and nasal passages of the user. Airways 286, 287 convey filtered and pressurised air to the mask (airway 286) and from the mask (airway 287) back to the generator unit 283 where the expired air may be exhausted via an exhaust filter. If pressure in the mask increases, further exhaust air may be vented via the exhaust valve's 298, 299 and/or mask material.

The outer cover 282 may facilitate aesthetic appeal of the breathing apparatus. The cover may include patterns, colours, and the like for aesthetic appeal. A plurality of such covers may be available, so that the user can change them, to vary the aesthetics of the breathing apparatus 280. The cover may also provide a function of protecting the user's face from the environment. In Particular, these covers may be very popular where it is usual and important to protect the complexion from the effects of UV radiation, for example.

In the above embodiment, the inner mask covers the nose and mouth. Various embodiments may only cover one of the nose or mouth. Further, covers such as the cover 282 may be used with other embodiments of the mask apparatus that have been described here. Covers may be varied in shape so as to operate with each embodiment.

The generator unit for the embodiment of FIGS. 22 to 24 is not limited to a neck component such as illustrated in the drawings but may be provided by other types of generator units positioned anywhere on the body.

Figure 25:
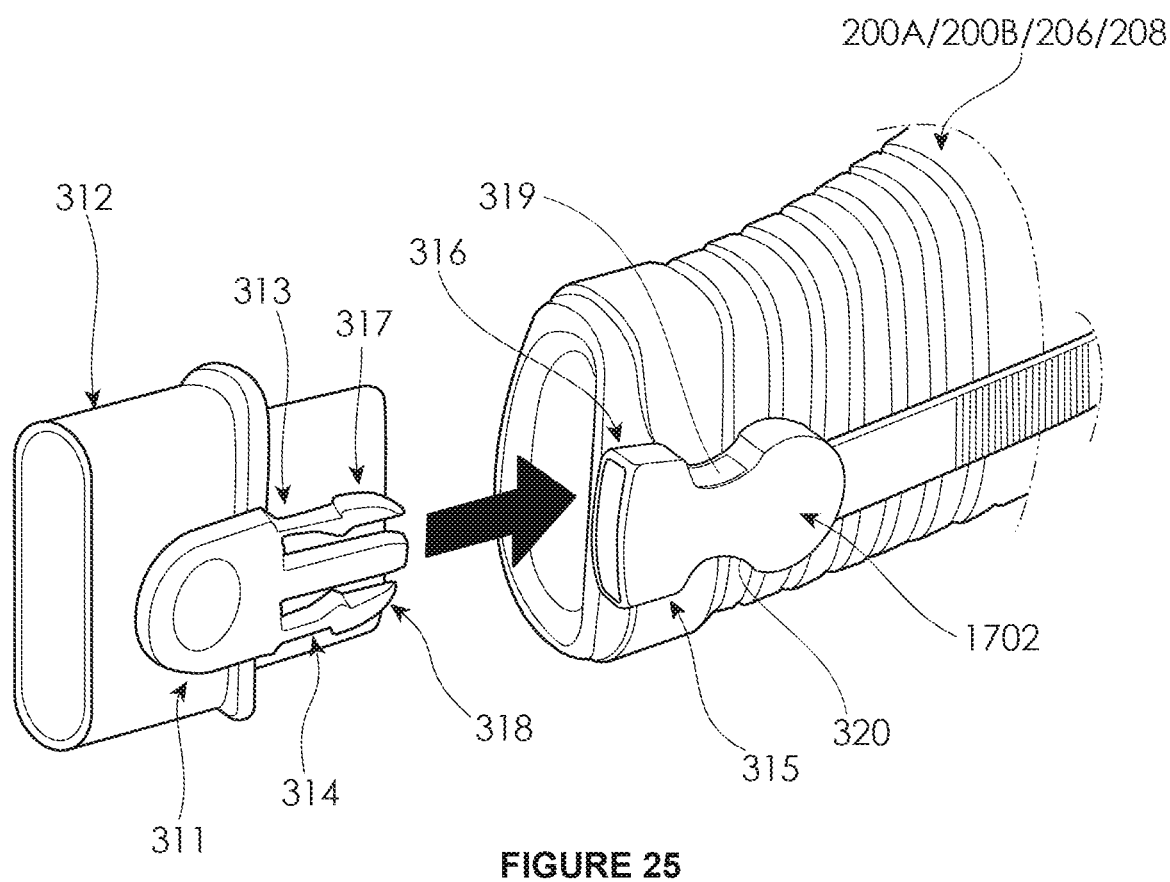
FIGS. 25 and 26 are details of an airway of a breathing apparatus in accordance with an embodiment of the present invention.
Figure 26:
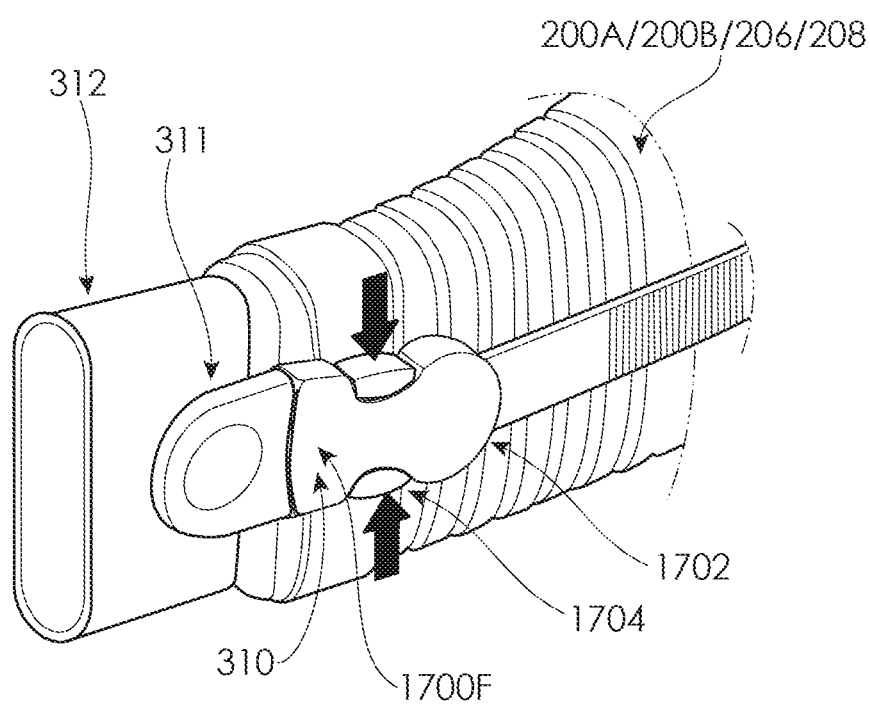

FIGS. 25 and 26 illustrate an alternative embodiment of a connector mechanism 310, for connecting an airway of a generator unit to an airway of a mask arrangement, for any of the embodiments described herein.

The connector arrangement 310 comprises a male connector component 311 which is mounted on the mask arrangement airway 312. The male component 311 has a pair of fingers 313, 314 which extend towards the generator unit airway 315 in use. Fingers 314, 313 are arranged to be inserted into a corresponding female member 316 mounted on the generator unit airway 315. The fingers 313, 314 include heads 317, 318 projecting distally and being arranged to engage with slots 319, 320 in the female member 316. The fingers 313, 314 are resilient so that they lock into the female member slots 319,320 the connector arrangement may be released by pressing the projecting portion 317, 318 in the slots 319, 320 and pulling the male member 311 away from the female member 315.

Figure 36:
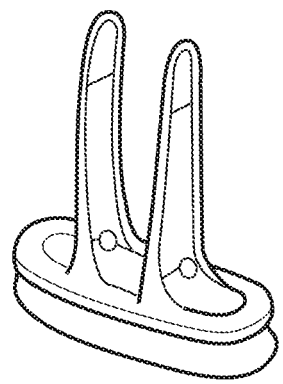
FIG. 36 is a perspective view of a supporting insert for use with a breathing apparatus in accordance with an embodiment of the present invention.
Figure 37:
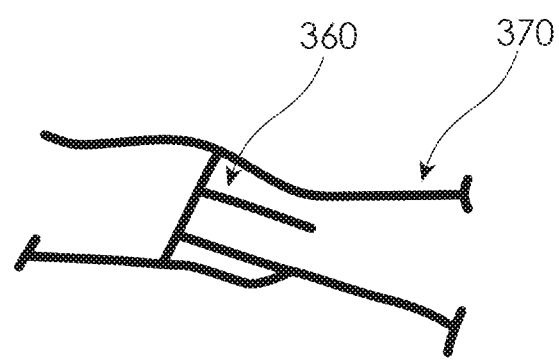
FIG. 37 is a diagram showing positioning, in use, of the supporting insert of FIG. 36.

In the above embodiments, there are a number of breathing apparatus which include a generator unit comprising a housing arranged to be mounted at the neck of the user. The housing may contain an airflow generator, filter, and other components. In some environments, particularly hot ones, wearing such a neck mounted unit may result in some discomfort. In an embodiment, a cooling device is provided to facilitate comfort of such a neck mounted unit. FIGS. 36 and 37 illustrate an embodiment of the cooling device.

The cooling device, generally designated by reference numeral 350 comprises a cooling insert 351. The cooling insert 351 comprises a material which is arranged to maintain coolness. The insert 351 is, in use, placed in a refrigerator for a time until it cools sufficiently. The cooling device 350 also comprises a cover 352 which is arranged to receive the cooling insert 351 within the cover 352 via opening 353. The cover 352 has a velcro attachment at the back (not shown) which is arranged to fit to a corresponding velcro pad on the neck unit of a breathing apparatus in accordance with an embodiment of the present invention, see FIG. 37.

In operation, the cooling device 350 maintains coolness of the neck of the user, promoting comfort.

The breathing apparatus of embodiments of the present invention include flexible airways for conveying filtered and pressurised air to the mask and conveying air from the mask (in some embodiments). Because the airways are flexible (see FIGS. 3 and 5, for example, where the airways are a flexible bellows) there is some potential for them to kink and close in operation. In order to prevent this, the present applicants have developed an insert, see FIGS. 36 and 37. The plastics insert 360 comprises a base 361 and a pair of fingers 362, 363 extending perpendicularly from the base. In operation, the base of the insert sits within an airway 370 and maintains the airway open even if it kinks. This is because the insert 360 by virtue of the fingers 362, 363 cannot lie flat and will maintain the airways in an open condition.

Figure 27:
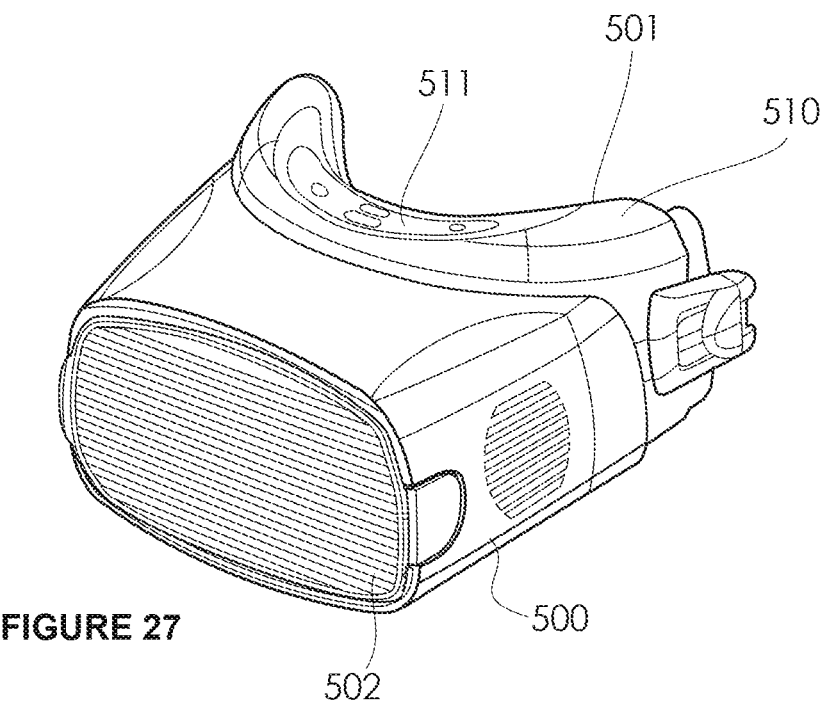
FIG. 27 is a perspective view of a generator unit for use with a breathing apparatus in accordance with embodiments of the present invention, shown with a further filter adapter attached and further filter.
Figure 28:
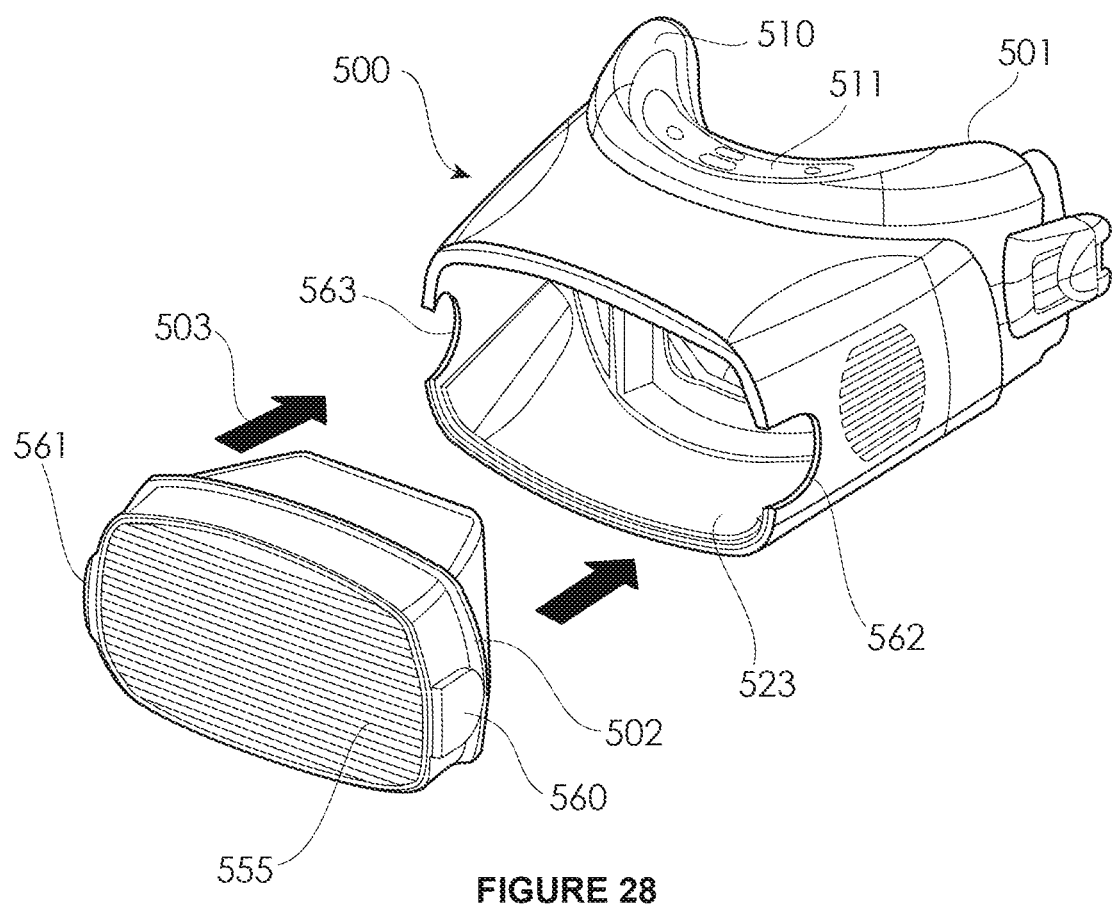
FIG. 28 is a view of the generator unit of FIG. 27 showing the filter removed from the further filter adapter.

Referring to FIGS. 27 and 28, there is illustrated a further filter adapter 500 which is arranged to be mounted to a generator unit 501 to receive further filter units, such as filter unit 502. Generator unit 501 may be the same or similar to generator units used in other embodiments of this invention, such as generator unit 162 of FIGS. 15 to 22. It may contain the same componentry. It will be used with an airway and mask arrangement in accordance with any of the embodiments discussed above or following.

In some circumstances, it may be required to use additional filter capability, which may require larger and bulkier filters to be added to the apparatus. For example, for extremely harsh environments with irritating or poisonous gases possibly present, gas filters may be required. Filter unit 502 may contain the appropriate filter and can be added to the generator unit 501 by using the filter adapter 500. The filter unit slots into the adapter 500, in the direction of the arrows 503.

The further filter unit 502 may be used in addition to filters already mounted in the generator unit 501, or in place of.

Enhanced filter functionality allows apparatus in accordance with embodiments of the present invention to be used in very harsh environments, such as hazardous gaseous environments, and even in military applications.

FIGS. 47 through 52 show more detailed views of generator unit 501 with a slightly modified filter adapter 500a and further filter unit 502a.

Figure 47:
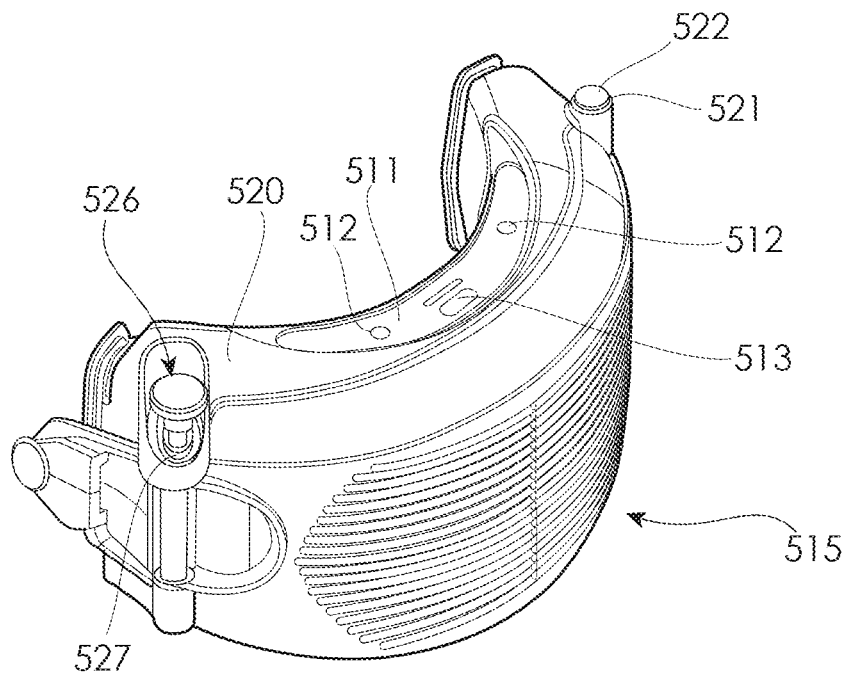
FIG. 47 is a perspective view of a generator unit for use with a breathing apparatus in accordance with embodiments of the present invention.
Figure 48:
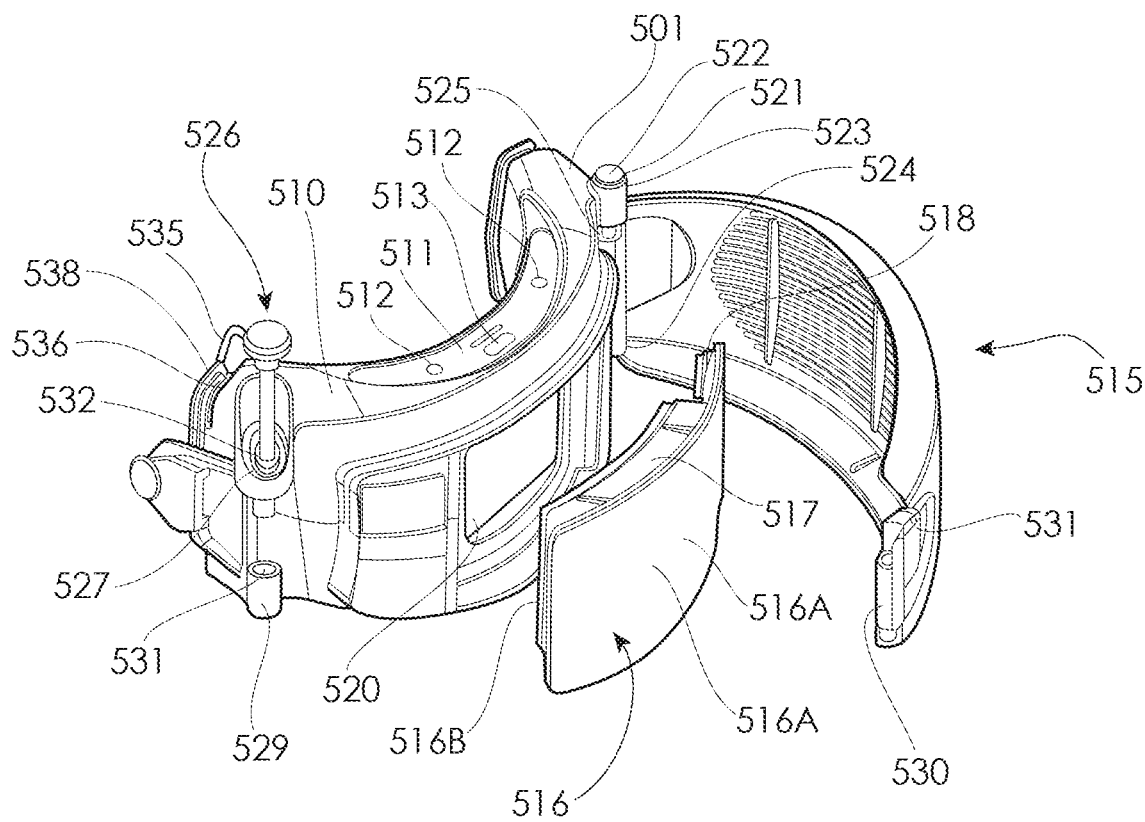
FIG. 48 is a further perspective view of the generator unit of FIG. 47, shown with a filter cover open.

FIGS. 47 and 48 show the generator unit 501 configured for use with standard filters, and showing how to replace filter units.

The generator unit 501 comprises a housing 510 within which the components of the generator unit (filters, impellers for powered air, control electronics and other components) are mounted. The housing mounts a touch control pad 511 which includes touch buttons 512 and displays 513 allowing the user to enter control parameters (e.g. air flow and/or pressure control, temperature, etc.). The control pad 511 may take any convenient configuration.

Figure 59:
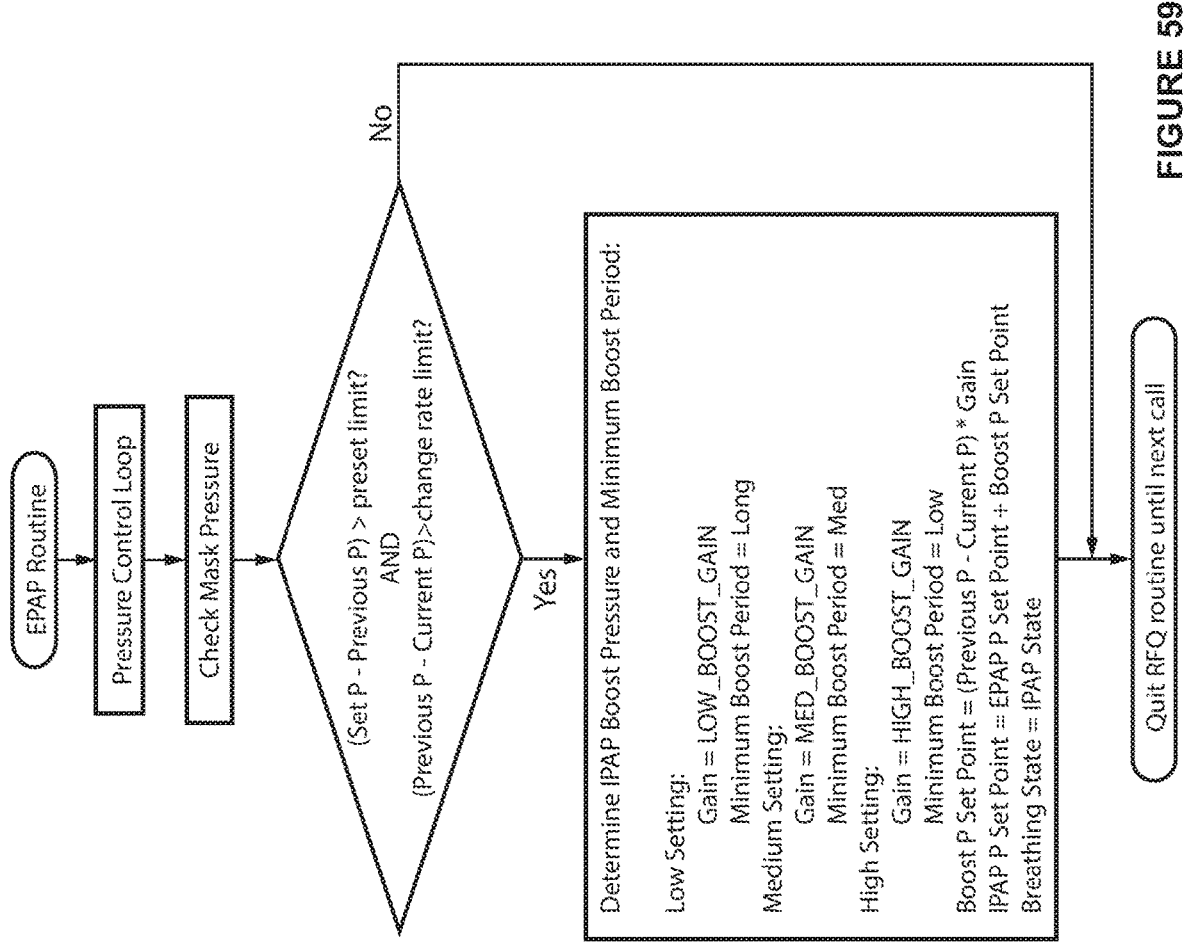
FIGS. 58 and 59 are flow diagrams illustrating controlling algorithms for control of a breath responsive arrangement for a breathing apparatus in accordance with an embodiment of the present invention.

A door 515 is mounted at the rear of the housing 510 and can be opened (shown opened in FIG. 48) to allow access to the housing 510, in particular to remove and replace filter cartridges 516. Filter cartridge 516 may contain a plurality of cascaded filters such as a HEPA filter, particle filter and any other filter, as discussed above. In the configuration as shown in FIG. 59, the filter cartridge 516 comprises an inhalation filter 517 (which may contain a plurality of cascaded filters, or may be only one type of filter) and also an exhalation filter 518.

The surface area of filter cartridge 516 is similar on the outside 516a and the inside 516b, at least as the filter area being presented at 516a and 516b. Having similar or equal areas of filter intake and outlet results in the filter material being used more efficiently.

The inhalation filter 517 is at the intake of the generator unit 501 (operation is the same as inhalation filter 185 shown in FIG. 14a and described above). Exhalation filter 518 is placed to receive output airflow and filter exhaled air (same as filter 187 of FIG. 14a, described above). The exhalation filter 518 may, in embodiments, also include a plurality of cascaded filters.

Filters 517 and 518 are mounted on a backing 519 and the cartridge 516 is arranged to slot into a receptacle 520 in the generator unit housing 510. Door 515 is then closed as shown in FIG. 47.

In some embodiments there may be no exhalation filter 518 on the filter cartridge 516. In some embodiments, the airflow does not return to the generator unit 501 for exhalation (see later on), and may be exhaled via a valve elsewhere or via a porous mass (e.g. a filter mask).

The door 515 is hinged to the housing 510 via a hinge 521. The hinge 521 comprises a hinge pin 522 mounted within a pair of cylindrical passages 523, 524 in the housing 510 and also running through a cylindrical passageway 525 at one end of the door 515. At the other side of the door 615 from the hinge 521 is a release pin 526 which can be actuated to a release position (shown in FIG. 48) so that the door 515 can be opened. The pin 526 and door 515 are shown in the closed position in FIG. 47.

The release pin 526 is slideable within a pathway 517 formed by a pair of lugs 528, 529 on the housing 510, the lugs 528, 529 defining cylindrical holes 531, 532 to receive the pin 526. The door 515, at its end corresponding to the position of the pin 526 has a lug 530 which defines a cylindrical passageway 531 which sits between lugs 529 and 528 when the door is closed and is arranged to receive the pin 526 therein in order to fasten the door 515 closed.

In order to retain the pin 526, the pin is secured to a spring 535 which is arranged to move within a slot 536 in the housing 510 in parallel with the movement of the securing pin 526. The spring 535 is bent at 538 and which interferes with the slot within which it moves to retain the pin closed when the pin is in the position shown in FIG. 47, by interference fit.

Figure 49:
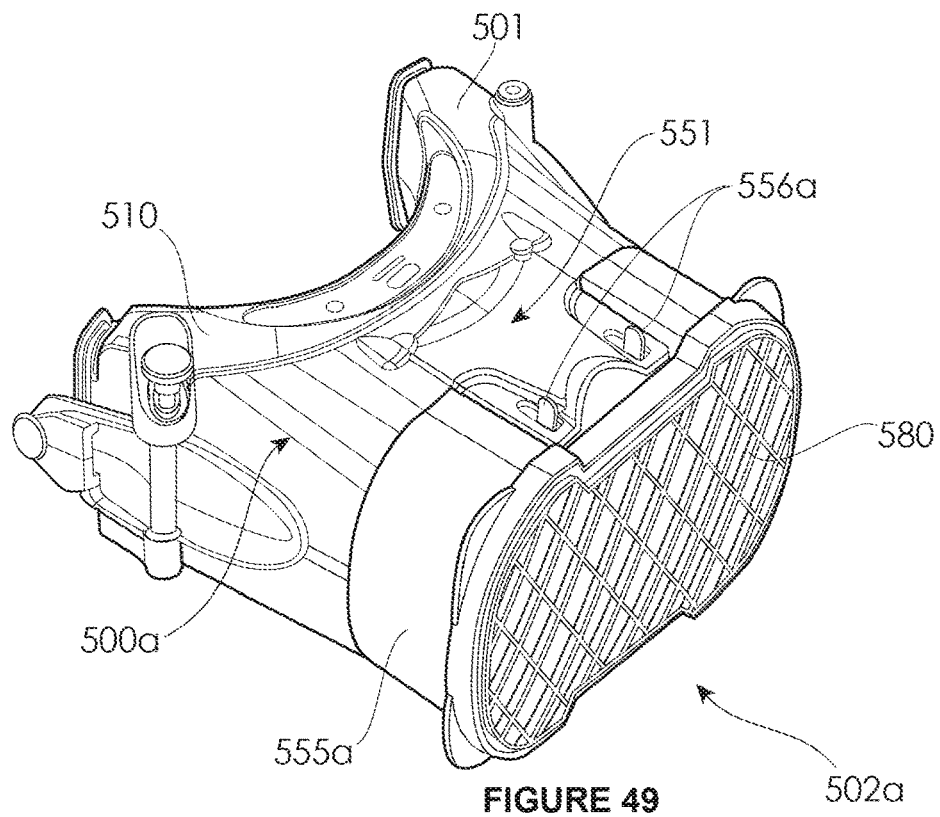
FIG. 49 illustrates the generator unit of FIG. 47, with a further filter adapter attached and further filter.
Figure 50:
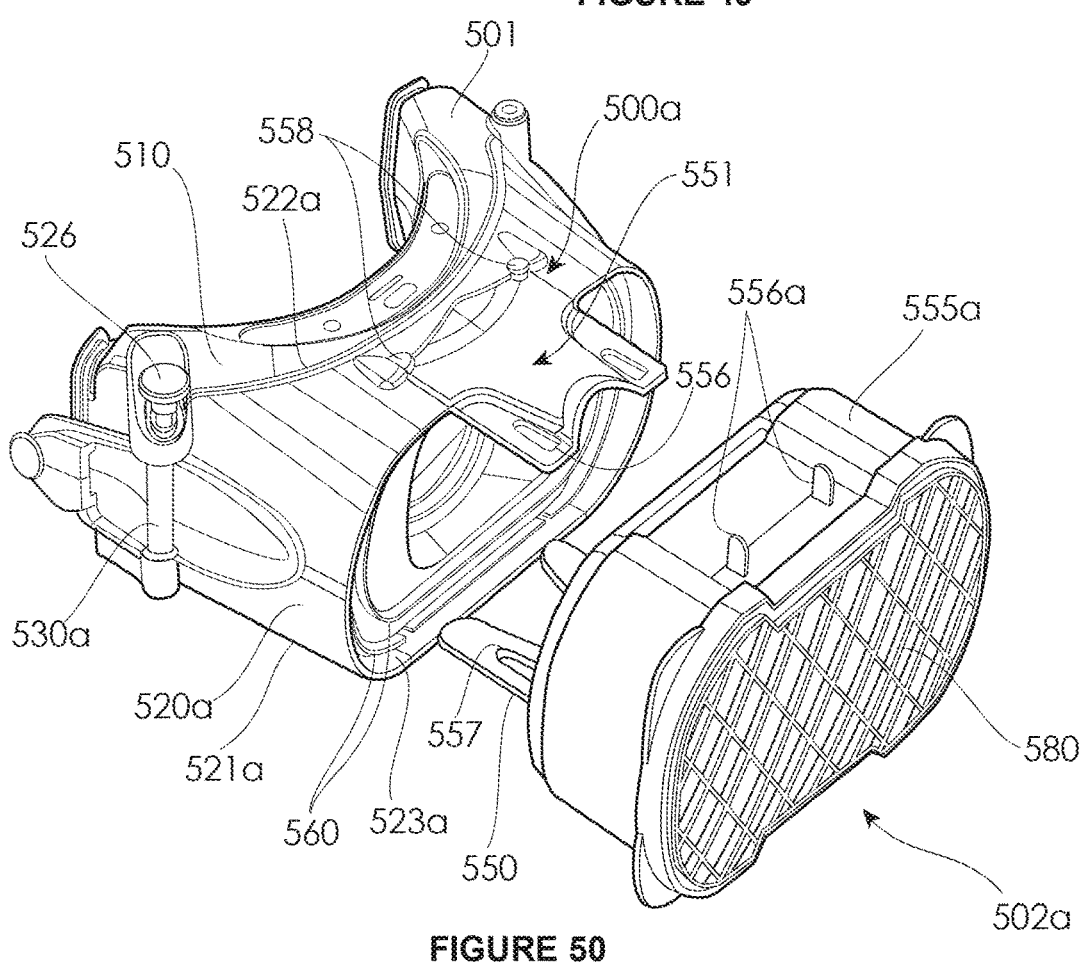
FIG. 50 shows the generator unit of FIG. 49, with the further filter detached from the further filter adapter.

The door 515 can be entirely removed from the housing 510, in order to mount the filter adapter (500 in FIGS. 28 and 500a in FIGS. 49 and 50). The pin 522 of the hinge 521 is removed by unscrewing using an alien key (not shown). The locking pin 526 is opened at the other side of the door 515 and the door can then be completely removed.

Referring to FIGS. 49 and 50, these show the filter adapter 500a secured to the generator unit housing 510. The filter adapter 500a comprises a frame 520a having sides 521a defining a front opening 522a in use arranged to fit over the opening 520 of the generator unit housing 510 and a rear opening 523a which is arranged to receive the further filter unit 502a.

The filter adapter 500a extends the dimensions of the generator unit so it can receive a large further filter unit such as 502a. The further filter unit can communicate with opening 520 in the generator unit housing 510 and therefore with airways 181 and 182 (FIG. 14a).

The filter adapter 500a in FIGS. 49 and 50 is secured to the generator unit 501 via the hinge 521 and locking pin arrangement 526. Further adapter 500a comprises a receiving element 530a arranged to receive the locking pin 526 and a hinge arrangement 523a arranged to receive the hinge pin 522. The filter adapter 500a also comprises a latch arrangement, comprising a latch 550 on the bottom of the housing 520a and a hinged latch 551 on the top of the housing 520a.

The filter unit 502a comprises a housing 555a mounting the filter 556a. The filter housing 555a is provided with projections 580 on the top and the bottom of the housing 555a (the bottom projections cannot be seen in the drawings but are the same as the top projections). These projections fit into slots 557 on the top 551 and bottom 550 latches of the filter adapter 500a. This is shown in FIG. 49. The top latch 551 is hinged on the filter adapter housing 528 by hinges 558. The bottom latch 550 is not hinged.

In operation, filter unit 502a is pushed into the opening 523a until the bottom projections 556a fit into slots 557 of the bottom latch 550. The top latch 551 is hinged open and then closed about the hinge so that the slots 557 receive the top projections 556a, as shown in FIG. 49, in order to secure the further filter unit 502a to the generator unit 501. Gaskets 560 are provided in the filter adapter 500a to seal the filter adapter to the further filter unit 502a. Alternatively, gaskets are provided on the filter housing 555a.

The filter unit 502a may include a powerful filter, such as a gas filter. It may include any other type of filter.

The filter unit 502a may include an inhalation filter and an exhalation filter, so that exhaled air can also be filtered (see FIG. 4).

In another embodiment, the exhaled airway path 182 may be sealed and exhaled air may be exhaled out of the sides of the mask or via a separate exhalation valve (e.g. a valve at the front of the mask or elsewhere). In this embodiment, 502a may be an inhalation filter only.

Figure 51:
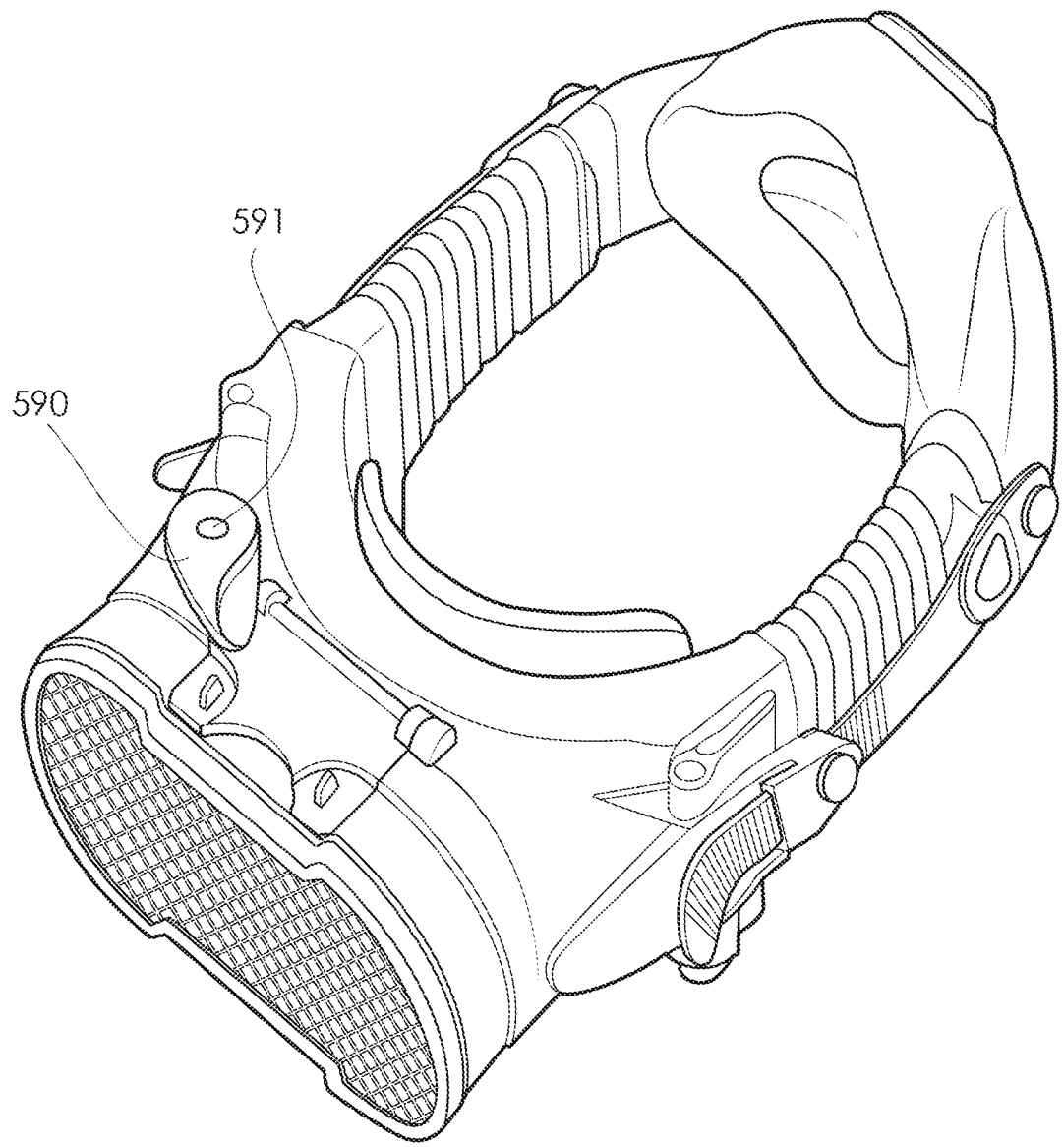
FIG. 51 is a perspective view from above and one side of the embodiment of FIG. 39 with the further filter adapter and further filter of FIGS. 49 and 50 attached.

FIG. 51 shows a perspective view of a mask arrangement in accordance with an embodiment of the present invention with the further filter adaptor 500a fitted. A latch arm 590 is shown mounted to the arrangement by a hinge 591. The latch arm acts in operation (as shown in FIG. 51) to secure the top latch 551 in position.

Figure 52:
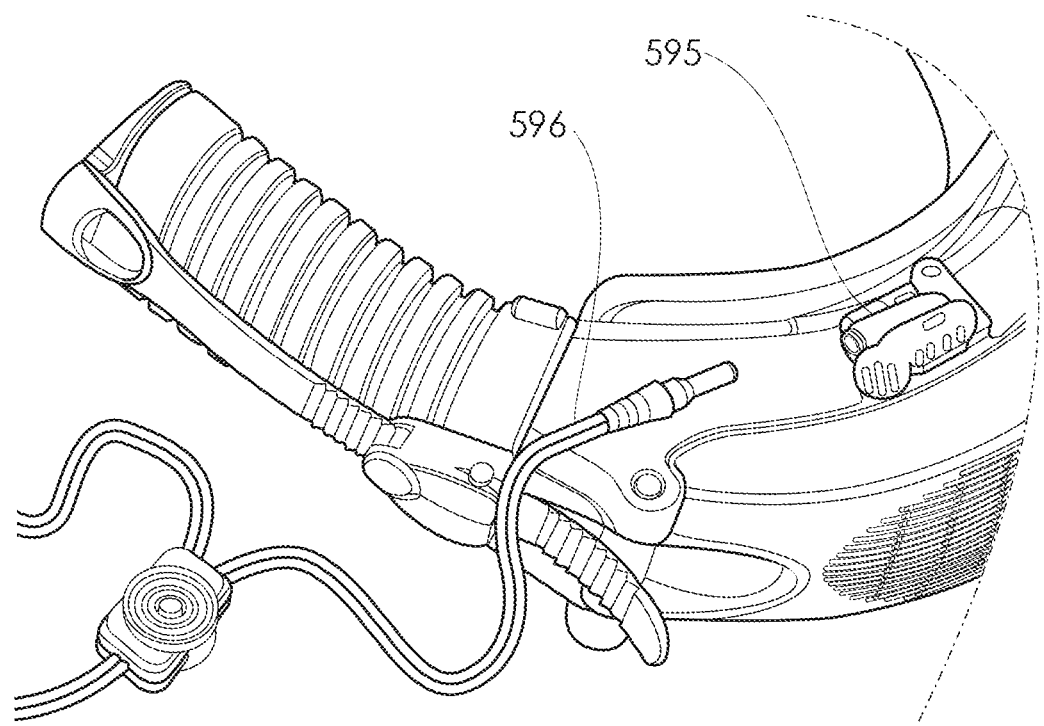
FIG. 52 is a detail of the embodiment of FIG. 39, showing a connection point for charging of a power source.

FIG. 52 shows an underside view of the apparatus of FIG. 51. A charging point 595 is arranged to receive the plug of a charger 596 in order to recharge the battery of the arrangement.

Figure 56:
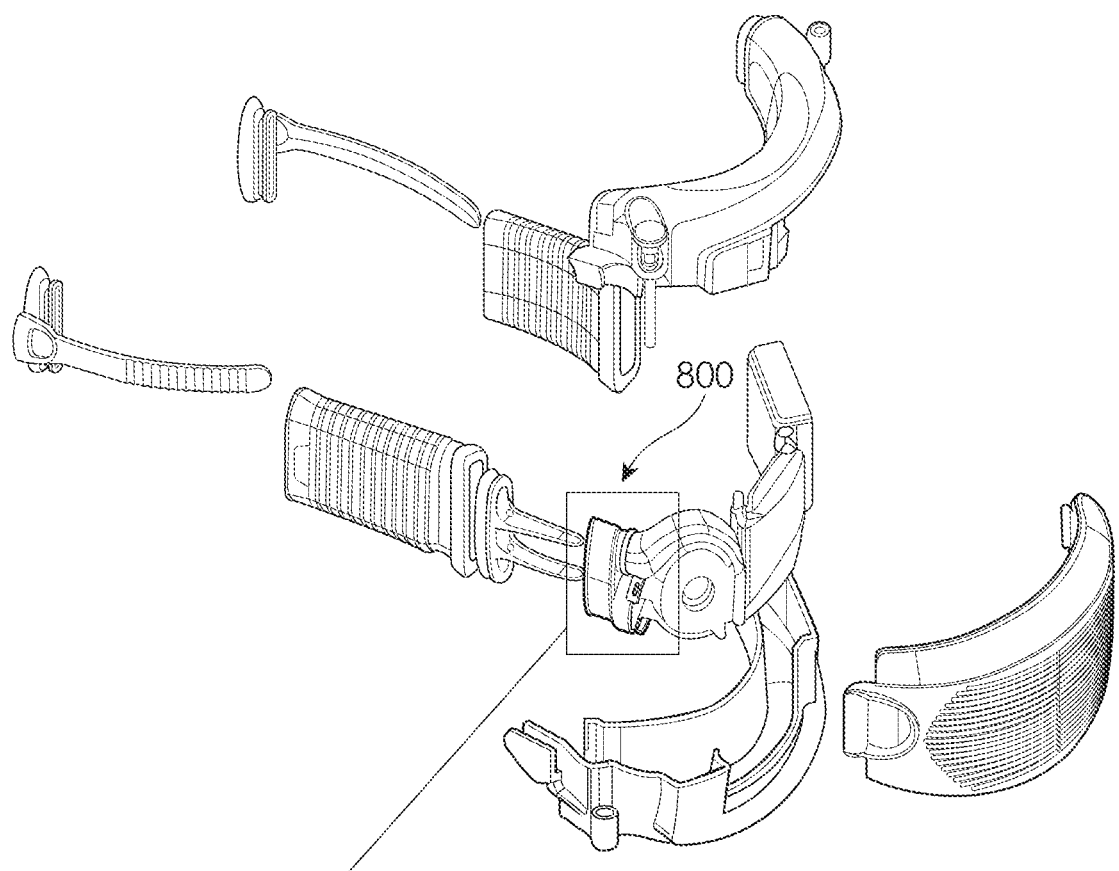
FIG. 56 is an exploded view of a rear end of an apparatus in accordance with an embodiment of the present invention illustrating a bypass arrangement.
Figure 57:
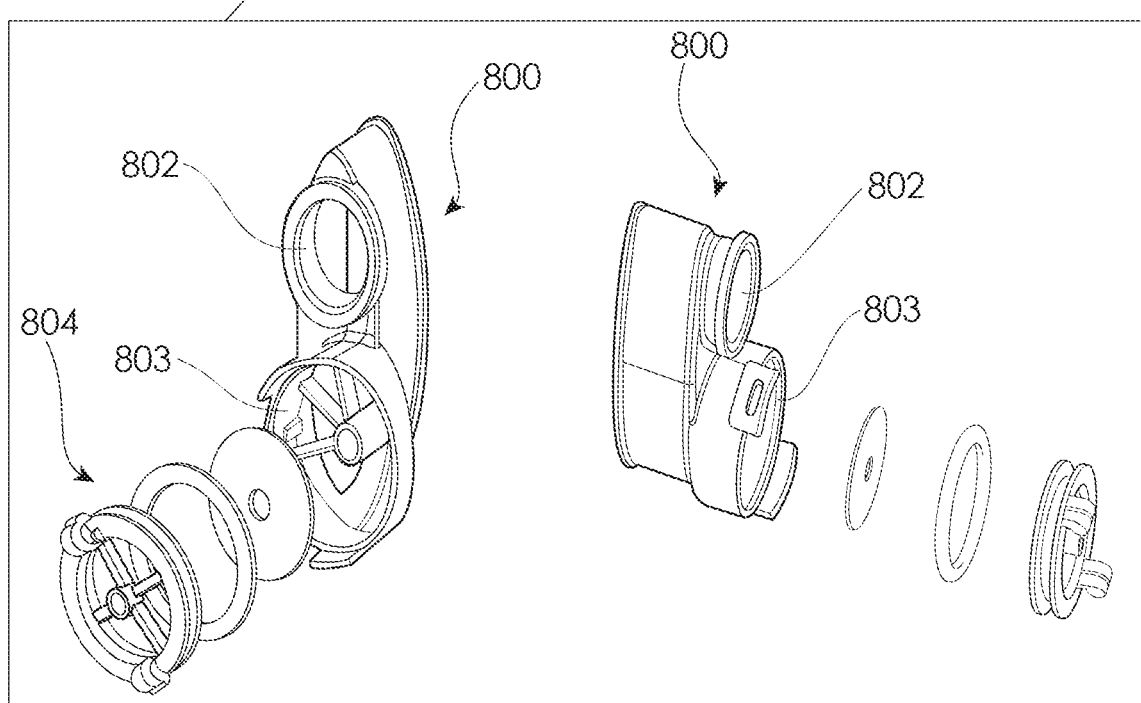
FIG. 57 is a detail view of components of a bypass valve for use with the embodiment of FIG. 56.

Referring to FIGS. 56 and 57, a bypass arrangement which can be used in embodiments of the present invention, generally designated by reference numeral 800, is illustrated.

In some cases, the airflow generator may be inoperable. This may be either because it is faulty, or the user chooses to operate the breathing apparatus in a non-powered mode, or for any other reason.

When the airflow generator is not operating, the air pathway passing through the air generator can result in resistance to airflow, which could make it difficult for the user to breathe.

The bypass arrangement provides a bypass pathway by which air can flow when the airflow generator is not working, which avoids air flowing via the airflow generator.

The bypass arrangement comprises a manifold 801 which has a first pathway 802 which allows airflow via the airflow generator. It also has a second pathway 803 which includes a bypass valve 804. When the airflow generator is operating, the valve 804 is closed.

When the airflow generator is not operating, the pressure differential is such that the user can breathe via the valve 804 and the bypass passageway 803.

In all of the above embodiments that include a circular airway (such as the embodiment of FIGS. 3 to 5, the exhalation path may be sealed and air may exit the apparatus via a further exhalation valve.

The ability to add a further filter (in addition or instead of filters already contained within the generator unit 501) provides further functionality for apparatus in accordance with embodiments of the present invention.

FIGS. 27 and 28 show an alternative embodiment of filter adapter 500. This embodiment may be integral with the housing 510 of the generator unit 510 or may merely slot in a receiving opening in the housing 501 without requiring locking pin and hinge arrangement.

The further filter unit 502 is arranged to slot into a rear opening 523 of the filter adapter 500. The filter unit housing 555 is of slightly different configuration to the filter unit housing 555a of FIGS. 49 and 50 embodiment. The housing 555 includes a pair of lugs 560 and 561 which are arranged to sit in corresponding receiving slots 562 and 563 in the filter adapter 500, as shown in FIG. 27.

A further embodiment will now be described with reference to FIGS. 38 to 46. This embodiment is a modification of the embodiment of FIGS. 3 to 5. Modifications include the addition of a head support arrangement 630, a modified exhalation valve 601 and a modified airflow pathway compared to the embodiment of FIGS. 3 to 5. The airflow pathway is not "circular" via inhalation limb 160 and exhalation limb 161. Instead, exhalation air pathway 161a is closed and exit of air occurs via exhalation valve 601. A further modification comprises a supplementary power supply mounted by supplementary power supply pack 600.

Referring to FIGS. 38 through 46, the same reference numerals have been used for components equivalent to those already described with reference to FIGS. 3 to 5, and no further description will be given of these components.

Figure 40:
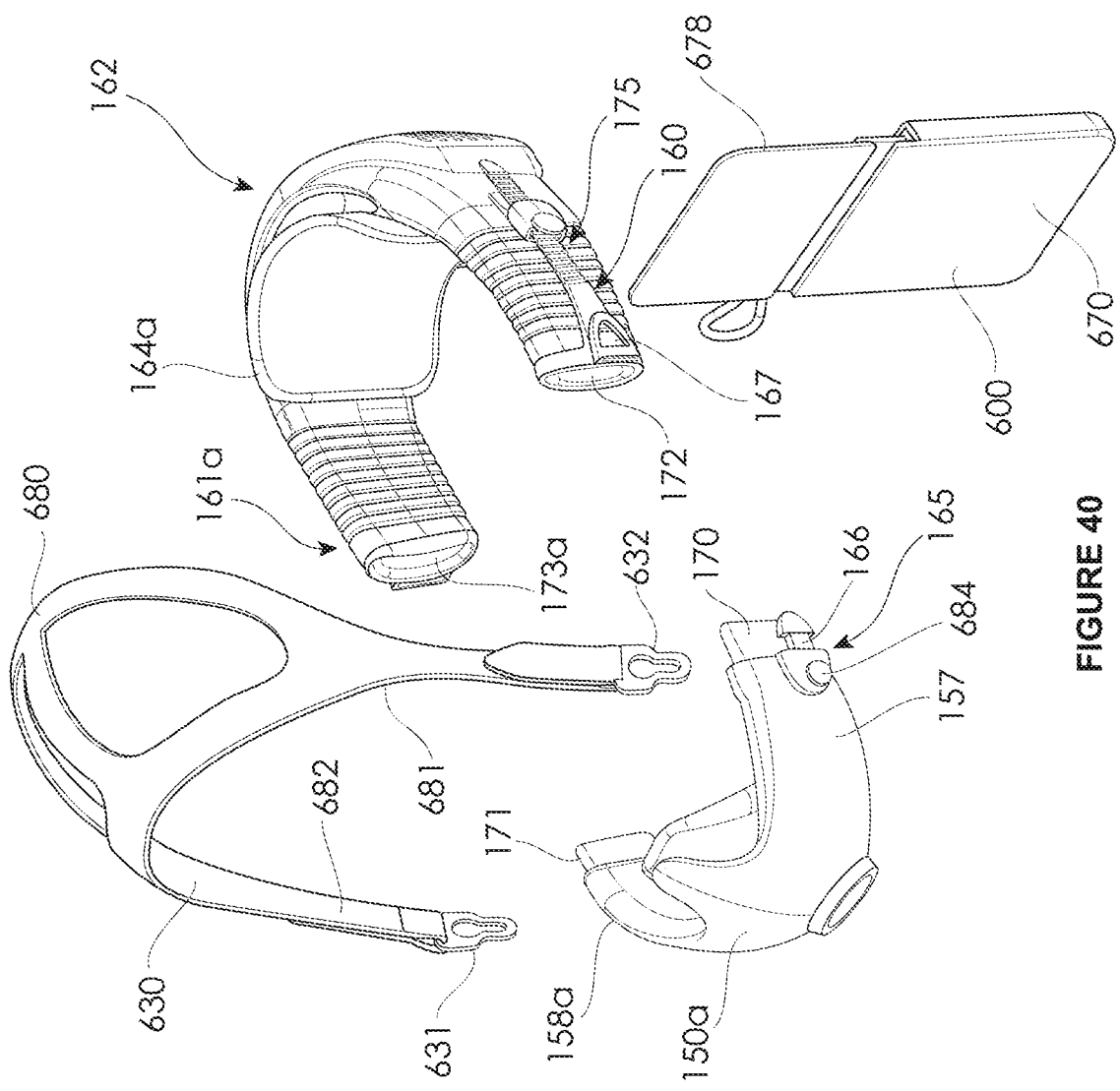
FIG. 40 is a further perspective view of the breathing apparatus of FIG. 39, shown with a head support in position.
Figure 41:
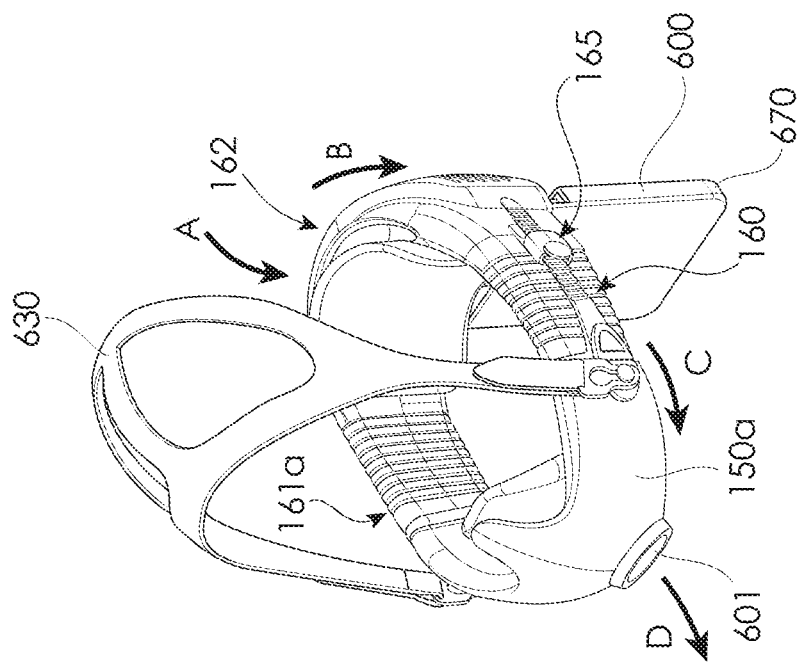
FIG. 41 is a disassembled view of the embodiment of FIG. 40.
Figure 42:
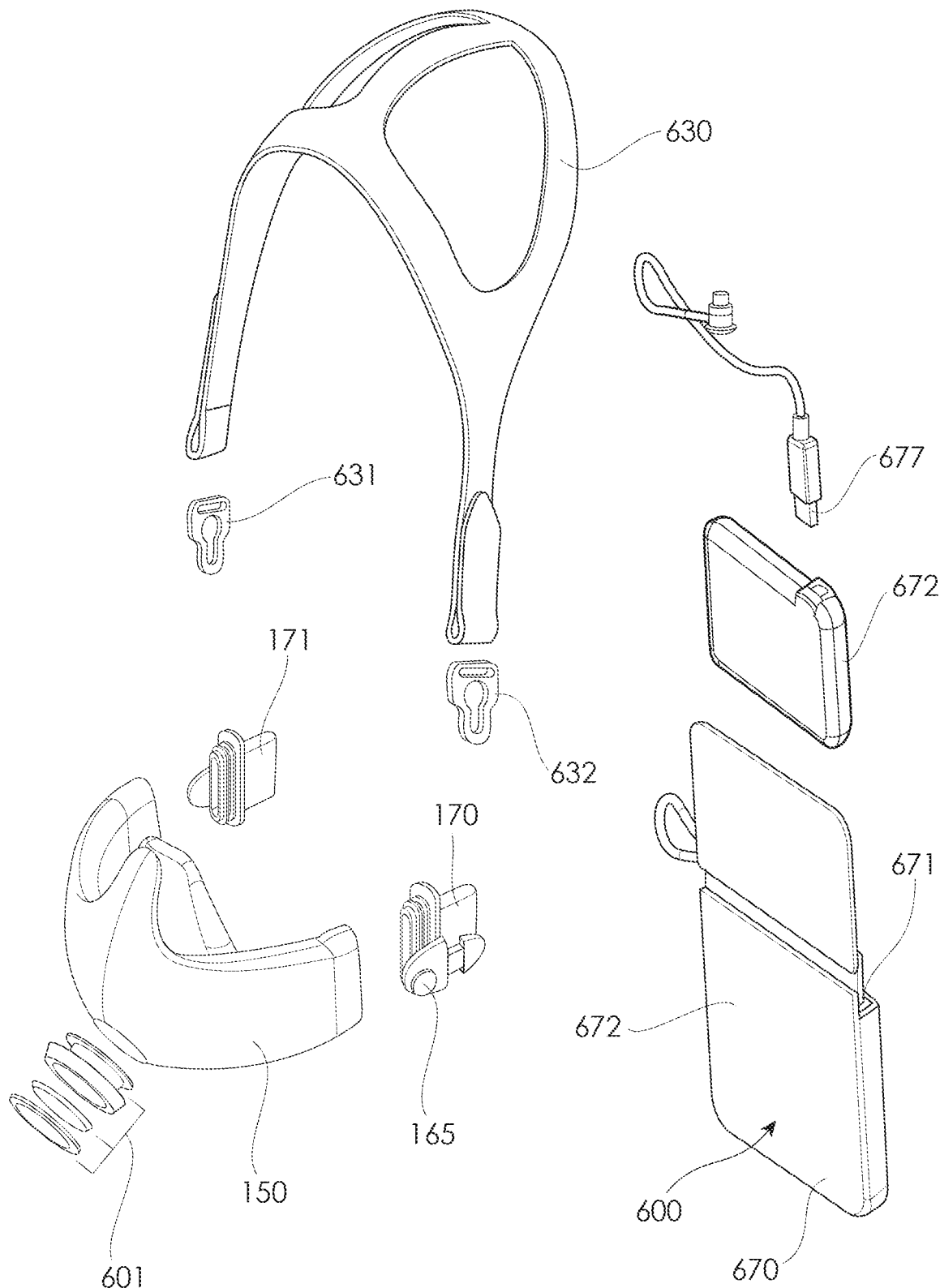
FIG. 42 is a further disassembled view of components of the apparatus of FIG. 40.

Referring to FIG. 40, the airflow pathway in this embodiment is generally as indicated by arrows A, B, C and D. Airflow is "in" via the generator unit (mounting impeller and filters) 162, around to the mask via limb 160 (arrows B and C) and "out" via the exhalation valve 601 (arrow D). Limb 161a is blocked by a partition (not shown) sitting within airway 161a.

The exhalation filter 601 currently mounted at mask 150a is shown in detail in FIGS. 47 and 48. The exhalation valve 601 comprises a valve base 620, which provides a valve seat 640. A valve actuator 621 comprising a disc 641 and projecting arm 651. The projecting arms 651 sits within a sleeve 652 within the valve base 620 and is retained by a spring 653 so that the disc 641 is biased to sit against the valve seat 640 and close the valve passageways 653 which communicate with the air chamber within the mask 150a.

A filter mount 622 comprising annular discs 655, 656 bracketing a perforated surface 657 to form an annular slot 658 for receiving the filter 623. Disc 656 has an opening 659 facing air passageways 653 and receiving the valve actuator 621 disc 641.

The exhalation filter 623 may be a HEPA filter or any other type of filter arranged to prevent particles being exhaled into the atmosphere (e.g. virus particles attached to droplets, bacteria etc.).

A filter cover 624 having a perforated outer rim 660 to allow the air to escape, covers the valve arrangement.

In operation, when a user exhales in the mask, the air pressure increases sufficiently to move the valve disc 621 against the force of the spring 653 to open the communication between the air passageway 653 so that air is exhaled via the filter 623 perforation 660 in the cover. When the pressure drops the spring 653 closes the valve.

This type of valve can be used for any of the embodiments described in the present invention. If allows exhaled air to be filtered so that contaminants, will not be exhaled.

Figure 38:
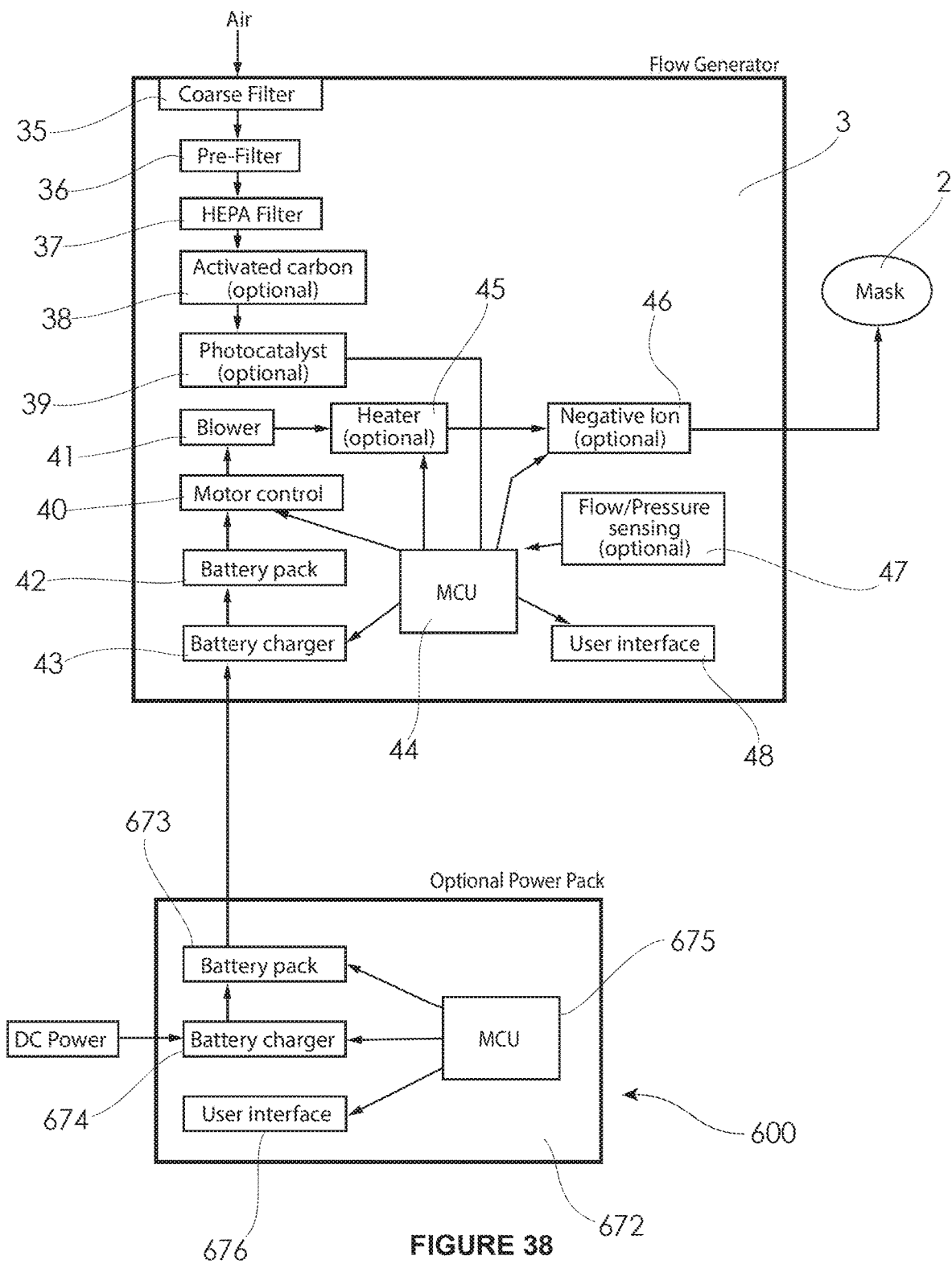
FIG. 38 is a block diagram of an air flow generator and filter unit of a breathing apparatus in accordance with further embodiment of the present invention.
Figure 39:
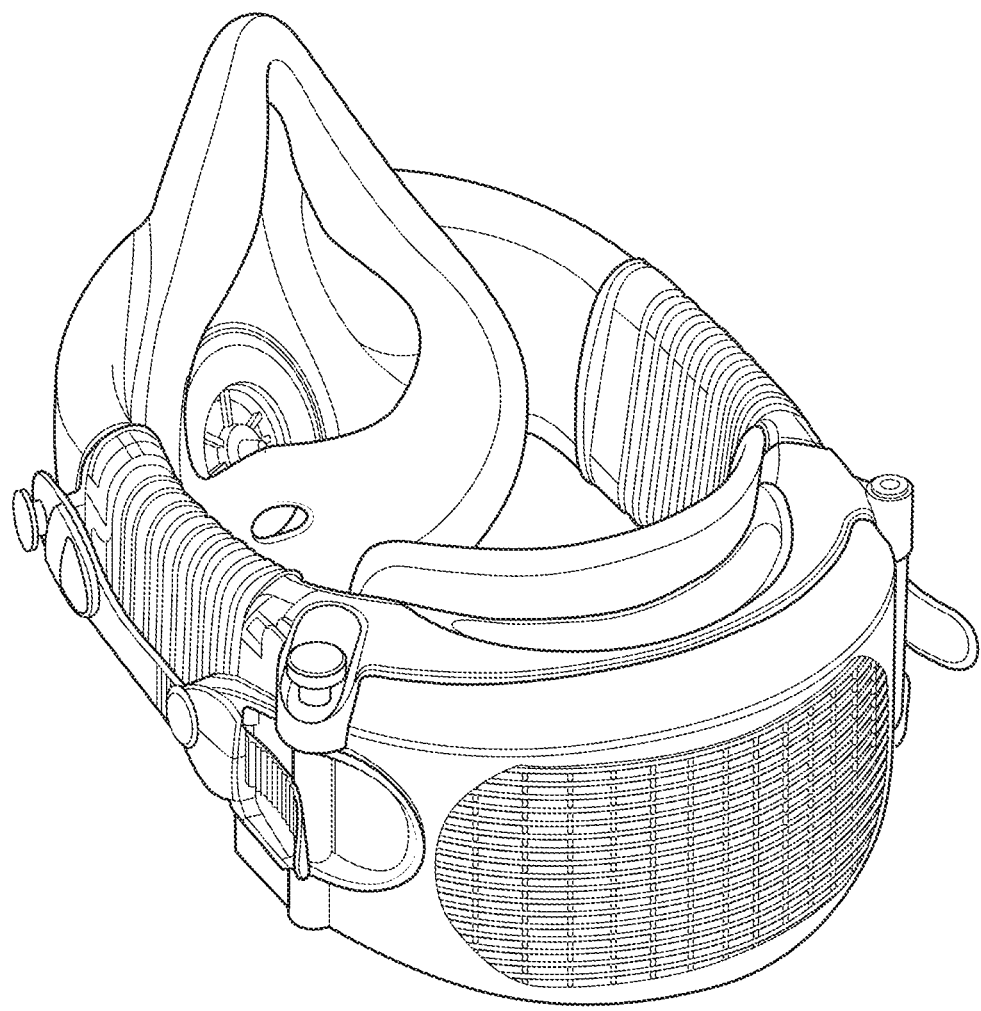
FIG. 39 is a perspective view of a breathing apparatus in accordance with a further embodiment of the present invention.

Referring to FIG. 38, in order to enable use of the PAPR for extended periods of time, a supplementary power supply is provided. A supplementary power supply arrangement 600 comprises a pouch 670 (FIGS. 40, 41 and 42) having an opening 671 and walls 672 forming a pouch arranged to receive a power pack unit 672. The power pack unit comprises (FIG. 38) a rechargeable battery pack 673, a battery charger 674, a micro-control unit 675 for controlling battery charging and a user interface 676. The connector 677 is arranged to connect the power pack unit 672 to the generator unit 162.

A flap of material 678 extends from the pouch 670 and, in use, is arranged to fit between the neck pad 164 and generator unit 162 in order to retain the pouch 670 in position. The flap 678 may include fastening means such as velcro and complementary fastening means may be provided on the neck pad 164a or a surface of the generator unit 162. Alternative connection means to Velcro could be buttons, buckles or any other connection means. The fabric of the pocket may be any flexible material, neoprene or leather for example. The pocket may have an opening or transparency to allow visibility of a battery indicator. An alternative to having an opening at the top for the battery pouch could be an opening at the side so the battery could just be slid in.

The embodiment of FIGS. 38 to 46 also includes a support in the form of a headband 630, to provide further support of the apparatus in use.

The headband 630 is in the form of a fabric webbing having a portion 680, which is webbed, and which is arranged to sit on top of the user's head in use. A pair of straps 681 and 682 extend from the webbed portion 680 and support connectors 631 and 632. Connectors 631 and 632 are arranged to receive lugs 684 provided on the sides of connector arrangement 165, so that the support 630 supports the apparatus in use (see FIG. 40).

Figure 43:
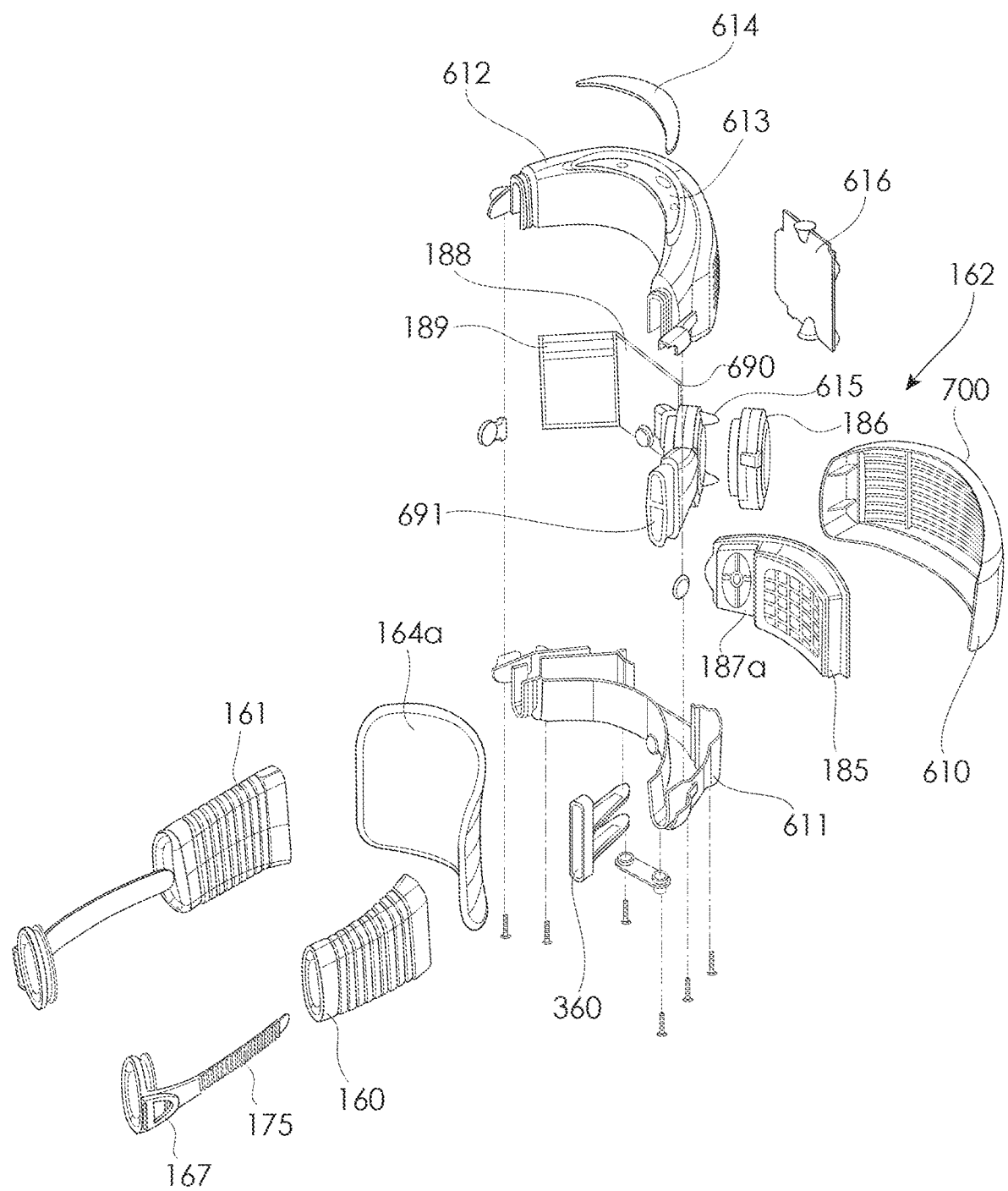
FIG. 43 is a disassembled view of further components of the apparatus of FIG. 40.
Figure 44:
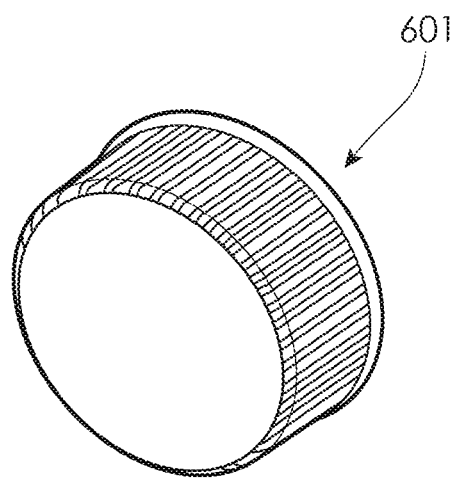
FIG. 44 is a perspective view from above and one side of an exhalation filter which may be used with embodiments of the present invention.
Figure 45:
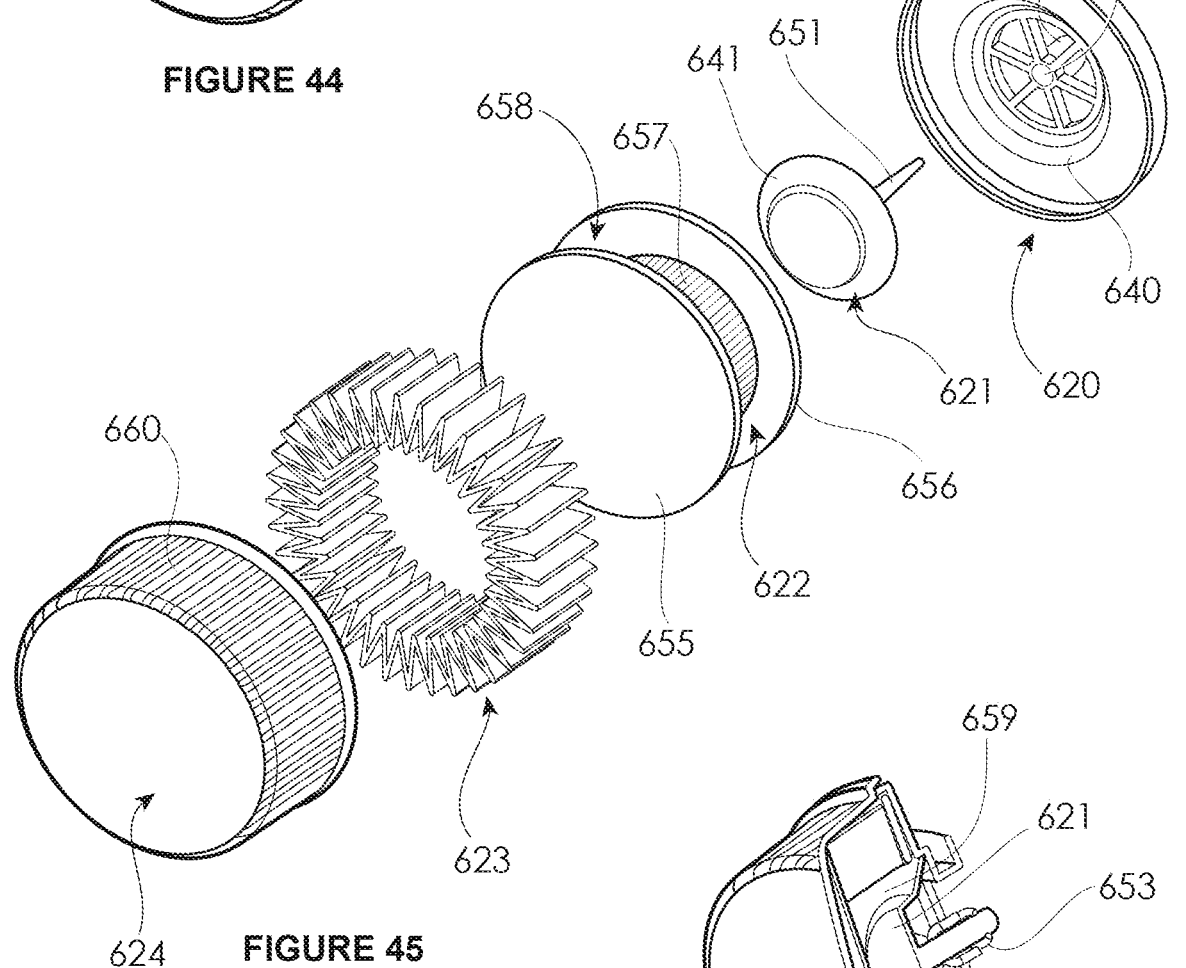
FIG. 45 is a disassembled view of the filter of FIG. 44.

FIG. 43 is an exploded view of the generator unit 162 of this embodiment, showing components in slightly more detail than FIGS. 3 to 5. Generator unit housing comprises a bottom base portion 611 and a top portion 613 that mount componentry when the base and top are closed. They also comprise a cover 610 which fits over the filter unit 185 and has perforations 700 to allow entry of air. Portion 187*a* of filter unit 185 does not have any exhalation filter as in this embodiment exhalation is via exhalation valve 601. In other embodiments, an exhalation filter may be provided and the airway 161 opened.

The housing 611, 613 mounts within it the onboard power supply 189, the control unit 188 and the impeller unit 186.

The control unit 188 comprises a printed circuit board 690 which mounts the components. A cover to the printed 6 circuit board 616 may be provided for heat dissipation. The cover 616 may also include a humidifier arrangement such as described in the Applicant's earlier application.

Impeller 186 is mounted on mounting 165 and air is drawn into the airway 160 via the impeller mounting 615 passageway 691.

The top part 612 of the generator unit housing comprises a control pad 613 and control pad cover 614.

Figure 34:
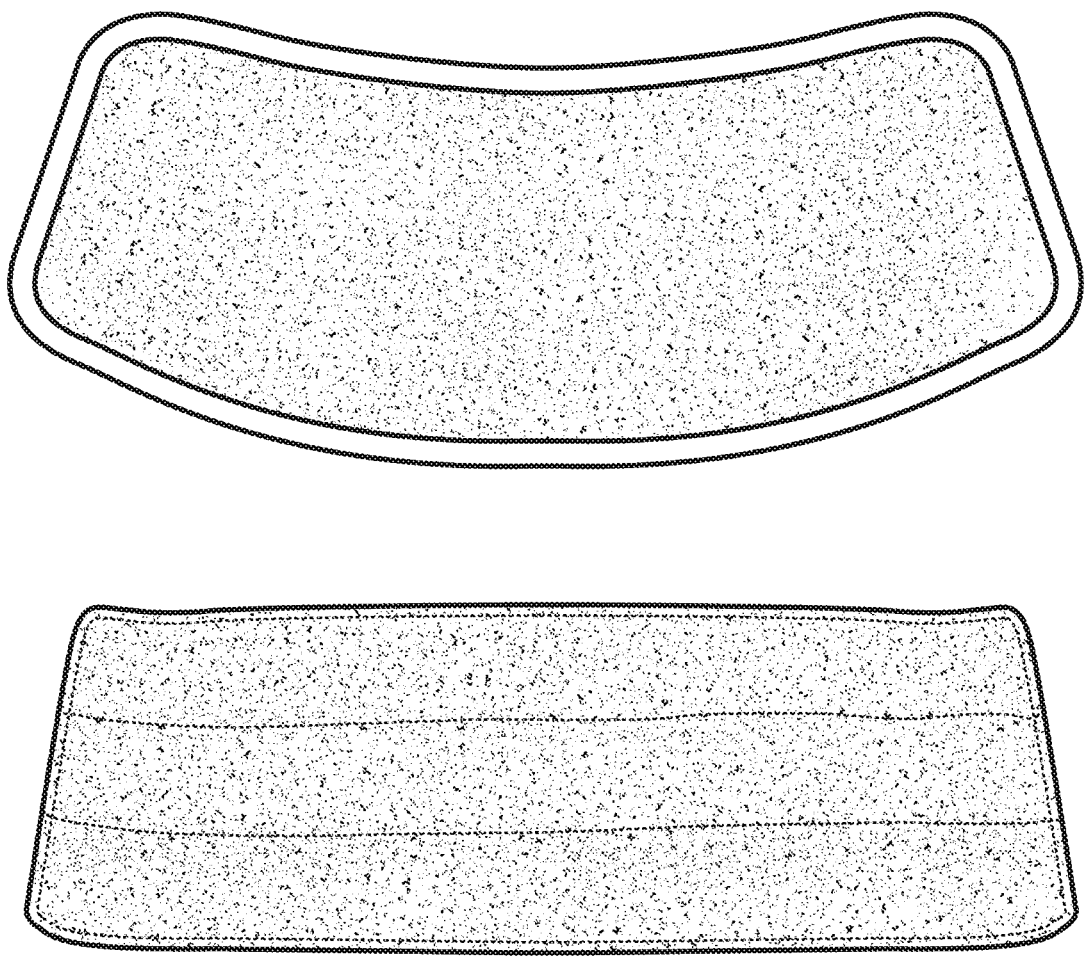
FIG. 34 illustrates a cooling device for use with a breathing apparatus in accordance with an embodiment of the present invention.
Figure 35:
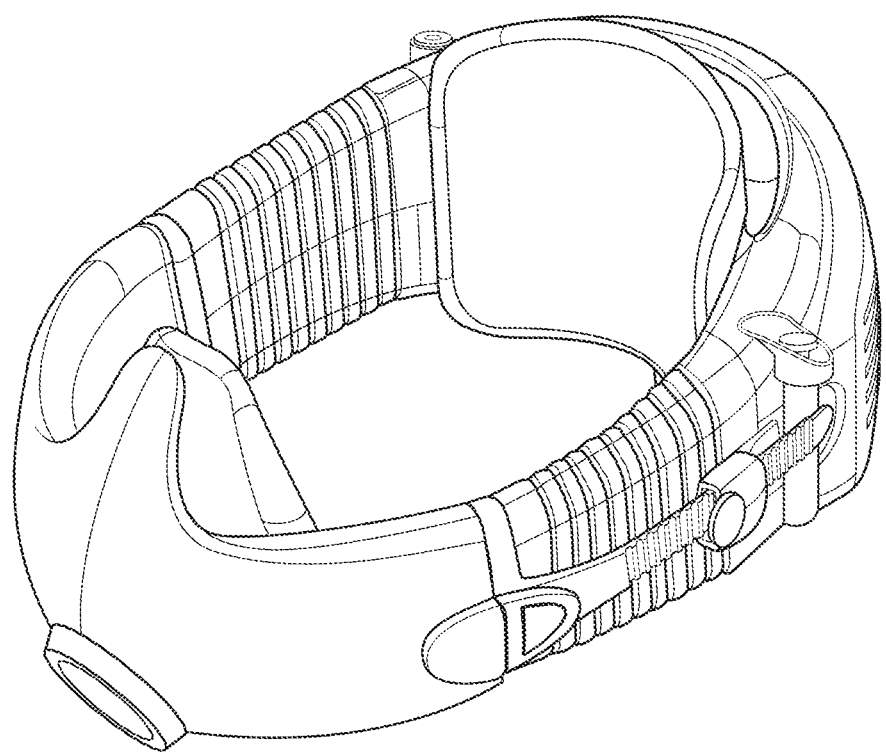
FIG. 35 illustrates the cooling device of FIG. 34 in position on a breathing apparatus.

The neck pad 164*a* is modified from the version of FIGS. 3 to 5 and may comprise a cooling arrangement such as described with reference to FIGS. 34 and 35.

A plastic insert 360 is provided (as described with reference to FIGS. 36 and 37) for maintaining airway 160 open.

Cover 700 may be removed in operation and a further filter adapter such as described with reference to FIGS. 27 and 28 and FIGS. 47 to 52 may be utilised.

A further embodiment of a breathing apparatus in accordance with the present invention will now be described with reference to FIGS. 29 through 33.

With the "neck mounted" generator unit embodiments, such as those described within reference to FIGS. 2 to 5 and 40 to 48, for example, the generator unit 162 is mounted tightly against the back of the neck. In some circumstances, this can make it difficult for the user to move their head freely and could cause some discomfort if worn for a very long duration.

The embodiment shown in FIG. 29 has the same componentry as embodiments of FIGS. 3 to 5 or 39 to 46, and no further description will be given of these components. The breathing apparatus 900 of FIG. 29 is, however, elongated as compared with other embodiments so that the generator unit 162*a* is spaced away from the back of the neck. See particularly FIG. 31. A neck pad 901 is arranged to fit against the back of the neck in use, an adjustment bracket is mounted on the air way 902 and 903 (adjustment bracket reference numeral 905). The adjustment bracket 905 supports the neck pad 901 using buttons 906 which fit into the holes 907 on the bracket 905. Note that bracket 905 will be on both air ways 902 and 903. This means the affixing the neck pad 901 is illustrated in FIG. 32.

An alternative method of affixing user's an integrated air clip 910 which is fixed to the air ways 902, 903 and the neck pad 901 has a strap 911 which fits through a buckle 912 on the air clip.

In this embodiment, the generator unit 162*a* is spaced from the back of the neck. A pivot point 915 is created which allows the user to tilt their head. The generator unit 162*a* is free to move without inhibiting neck movement.

Figure 53:
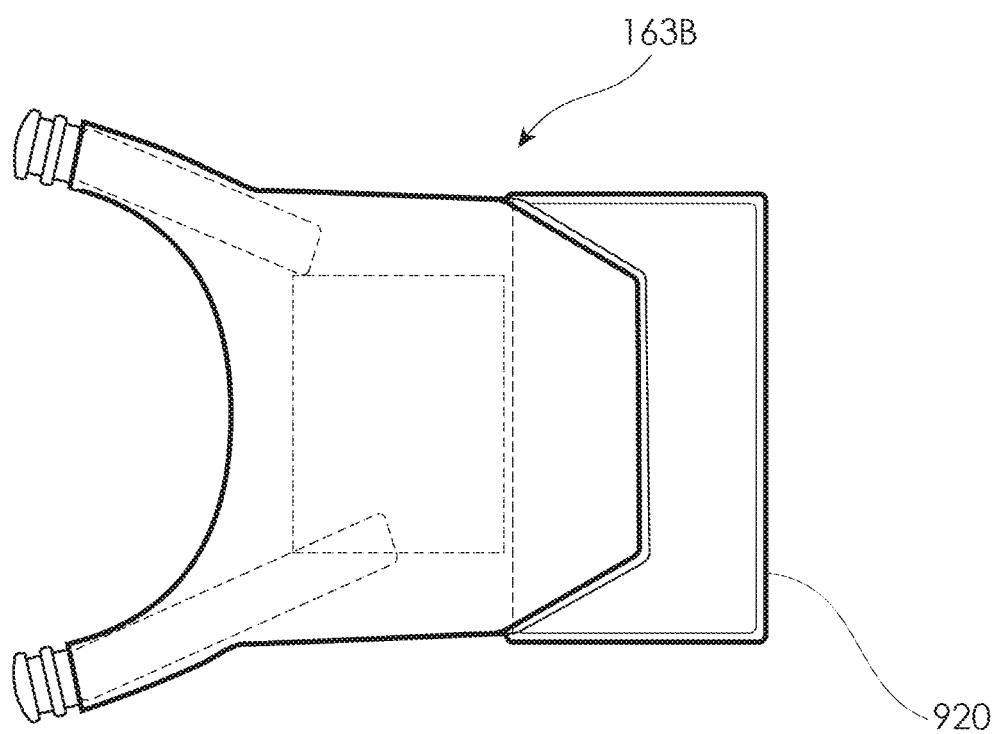
FIG. 53 is a schematic view from the top of a generator unit for use with a filter apparatus in accordance with embodiments of the present invention.
Figure 54:
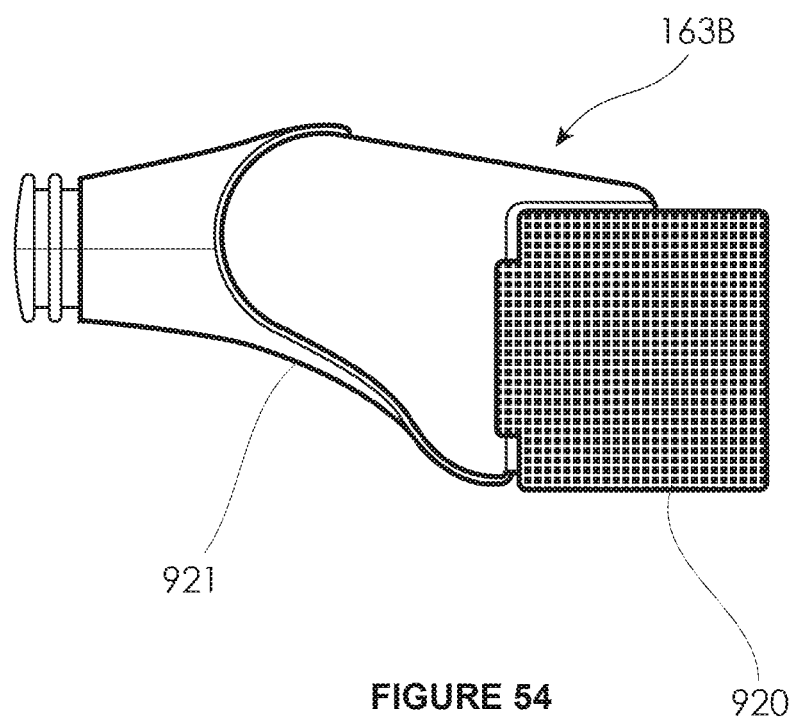
FIG. 54 is a view from the side of the generator unit FIG. 53.
Figure 55B:
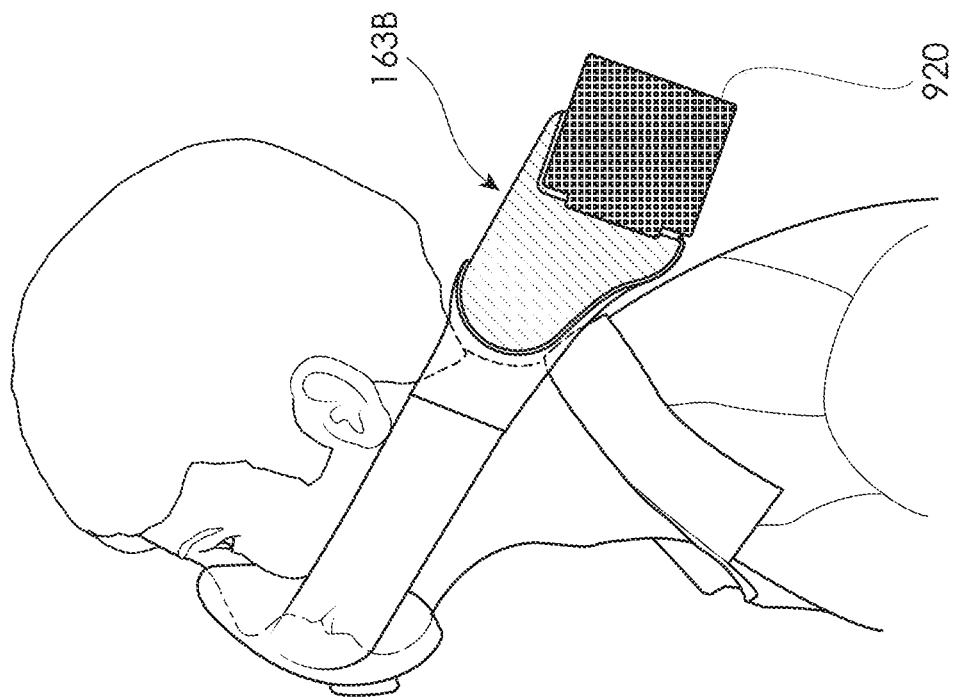
FIGS. 55(a) and 55(b) show schematic diagrams of embodiments utilising the generator unit of FIG. 53 and FIG. 54, illustrating different attitudes in use.
Figure 55A:
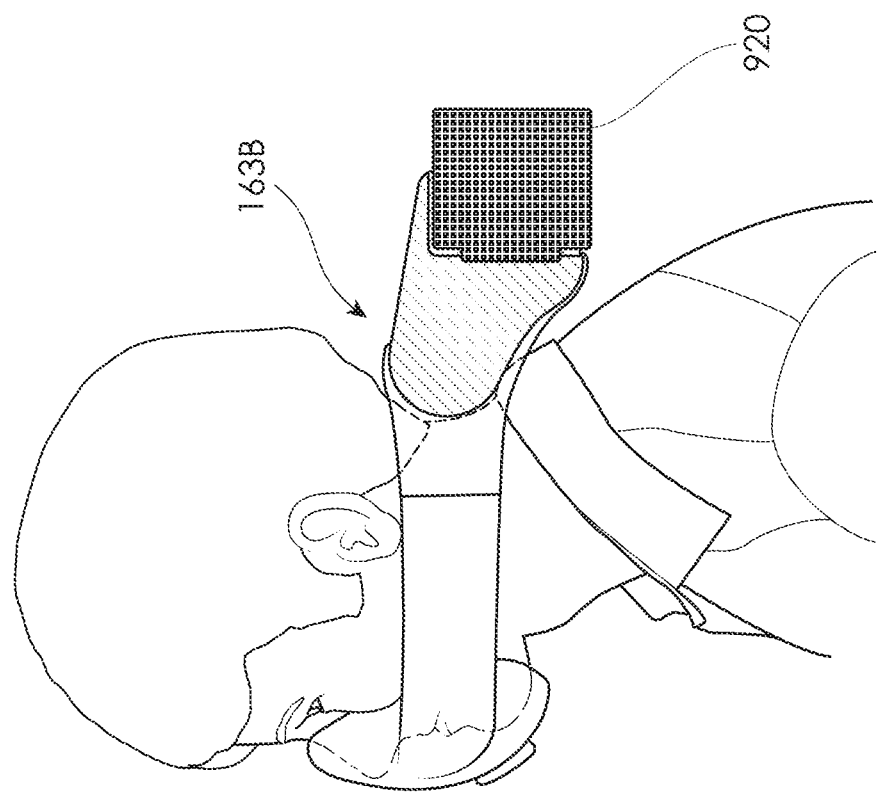

A further embodiment of an adjusted position generator unit is illustrated in FIGS. 53 to 55. The generator unit shown, reference numeral 162*b* is arranged, in use to be supported by the shoulders of the user (see FIGS. 55*a* and 55*b*). The generator unit 162*b* may support a gas filter cartridge 920.

A central portion of the generator unit 162*b*, is contoured (921) to follow the contour of the neck and shoulder. A larger weight can be comfortably supported by the shoulders than the neck. It enables comfortable, long term wearing of the breathing apparatus and the ability to be able to tilt the head comfortably.

As discussed above, embodiments of the breathing apparatus of the present invention may implement a breath responsive control, so that the air pressure may vary with the breathing rate. The motor power (fan motor) may also vary during the breathing cycle. In any breathing cycle, there is a breathing interval, a pause where there is no breathing, and exhalation interval.

Breath responsive embodiments of the present invention may take into account rate of breathing as well as varying motor control during a breathing cycle.

Referring to FIGS. 58 through 61, embodiments of the present invention implement a responsive flow control algorithm consisting of control functions for the exhalation positive air pressure (EPAP) and the inhalation positive air pressure (IPAP). In the EPAP control function (see FIG. 59) a breath responsiveness program is implemented, the program detecting the start of inhalation at the end of the EPAP state and calculating boost pressure based on the product of the breathing effort and the user gain setting to be used for the IPAP state following the EPAP state. The cycles of the EPAP and IPAP repeat breath by breath.

Figure 58:
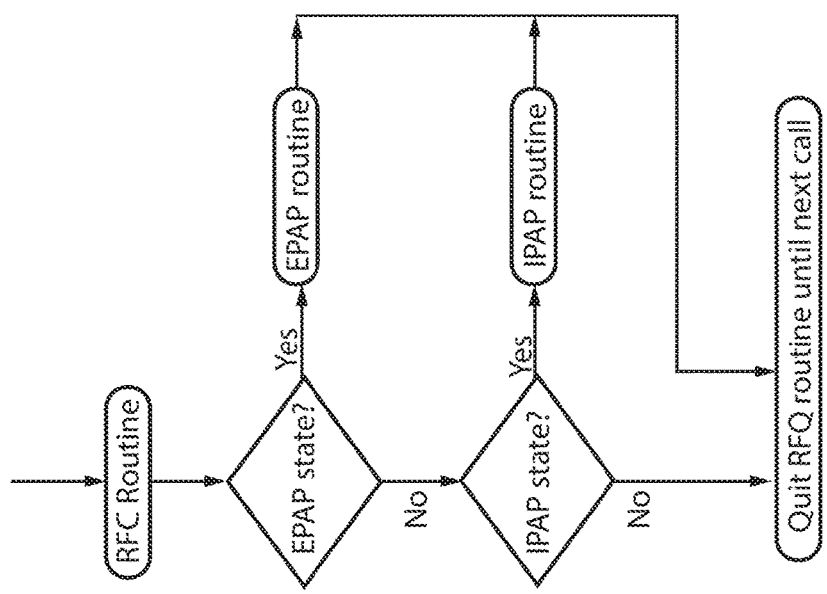
Figure 60:
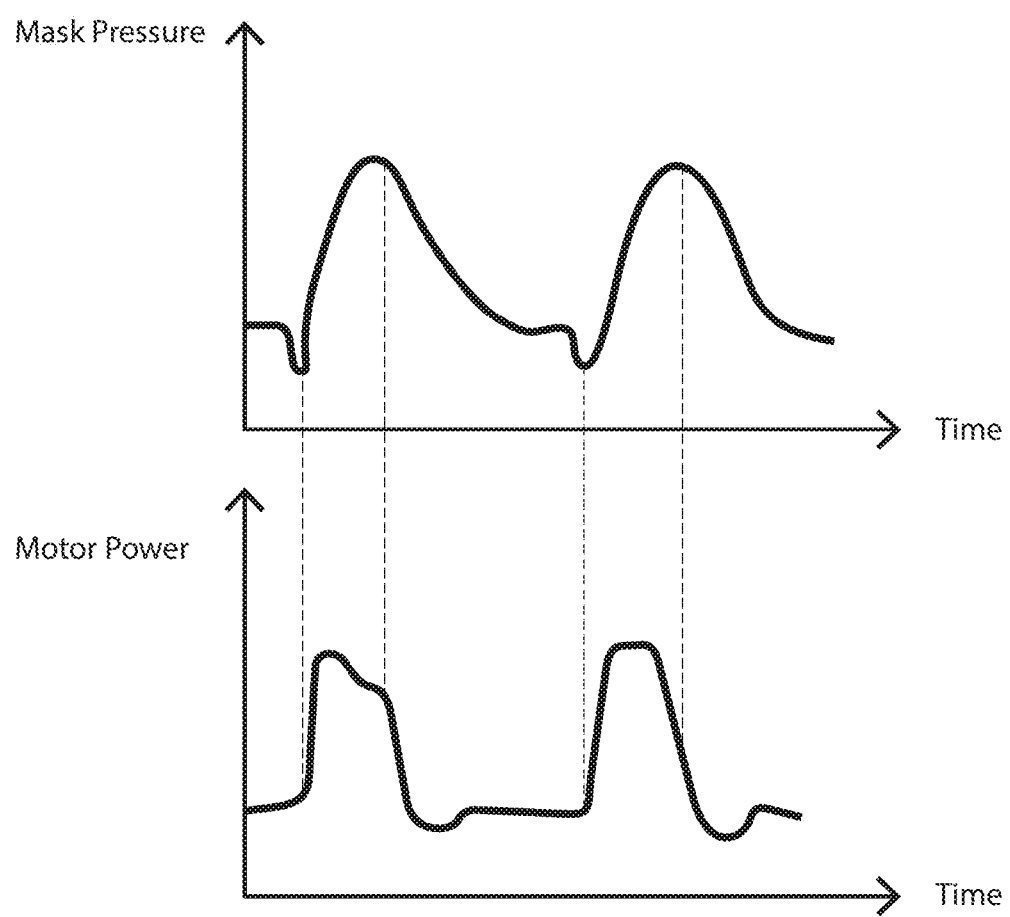
FIG. 60 shows two graphs of mask pressure and motor power during a breathing cycle.
Figures 61A, 61B:
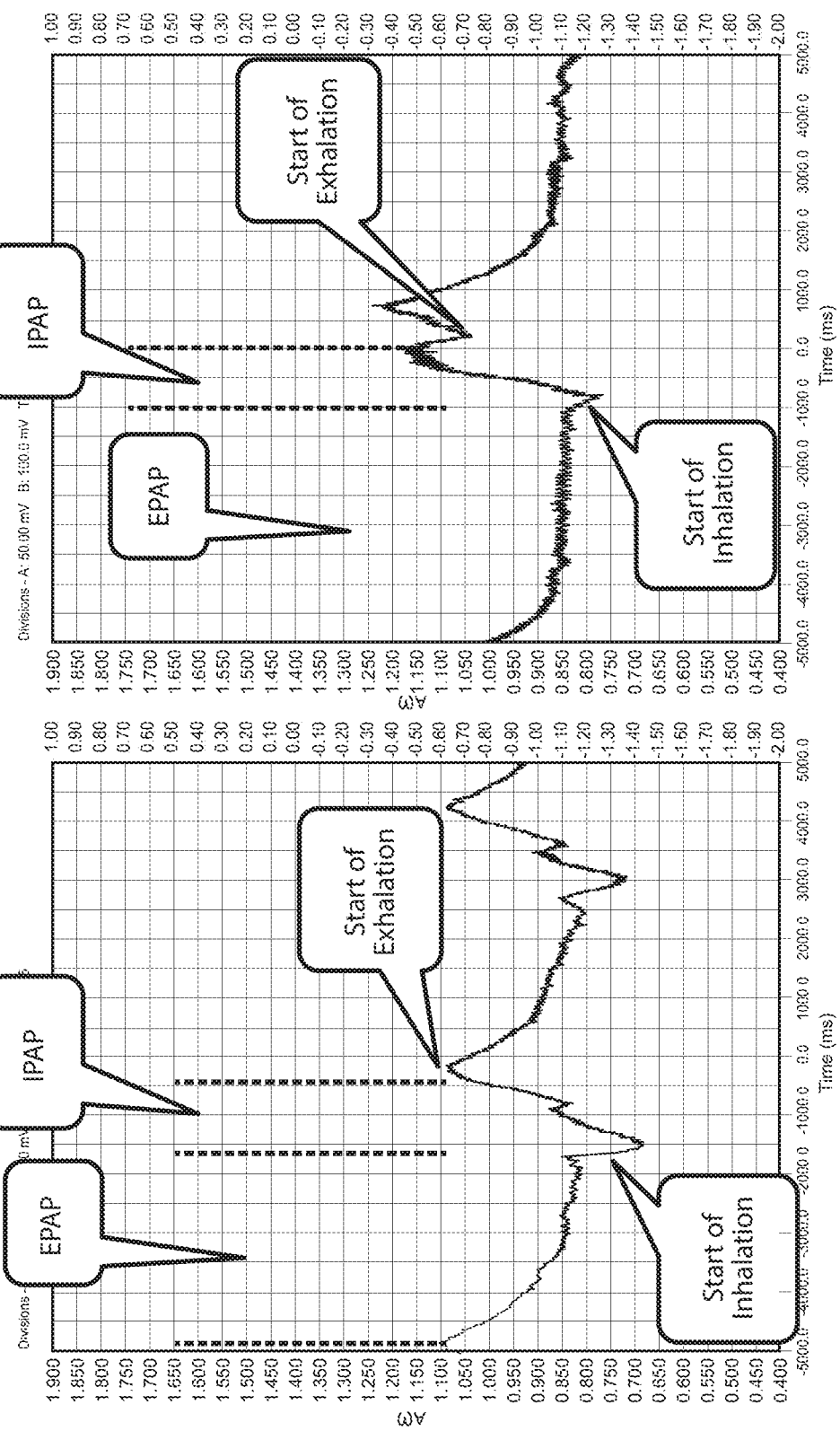
FIGS. 61a and 61b are mask pressure wave forms for operation of an embodiment of the invention.

FIG. 58 and FIG. 59 are flow diagrams showing the control algorithms. FIG. 60 shows graphs comparing mass pressure with motor power. FIGS. 61A and 61B show the mask pressure waveforms during the breathing cycle.

The breath responsiveness control program is based on the product of the breathing effort and the user gain setting (the user may manually set what air pressure they wish to have). The higher the product, the higher the responsiveness. Breathing effort is calculated by measuring the pressure drop in a defined period after the mask pressure goes below the set pressure point for the EPAP. The gain setting is user selectable, the higher setting leading to higher sensitivity of the blower output to the breathing effort. FIGS. 58 and 59 illustrates steps for the breath responsiveness control.

- For a given Gain setting, the higher the pressure dips at the start of the inhalation, the higher the breathing effort.
- For a given Gain setting, if the breathing effort is sufficiently large, the blower tends to reach its maximum capacity.
- With a higher Gain setting, the same breathing effort can lead to higher flow responsiveness, for saving breathing effort.
- With a higher Gain setting, the pressure dips at the start of the inhalation is relatively less, thus the minimum mass pressure is higher and more suitable for higher exertion work or for persons with higher lung capacities while it may be felt irritating for lower lung capacities.

With higher Gain setting, average IPAP pressure is higher at a cost of more battery consumption.

For light work, or for persons with lower lung capacities, a lower Gain setting may be more comfortable and the blower may be quieter and the battery will last longer.

For embodiments of the present invention, the mass pressure range is from 0.1 cm $H_2o$ to 3.5 cm $H_2O$. Target EPAP pressure may be from 0.5 cm 1 cm $H_2o$. The target inhalation pressure is variable depending on breathing effort and user comfort setting, and is higher than 1 cm $H_2o$ and up to 3.5 cm $H_2o$.

As discussed above, control of the breathing apparatus may include software control. Software control may include:
- Predictive software to predict when the filter is blocked. As the resistance of the filter becomes higher, the blower may have to work harder.
- Blower flow capability checking. Utilising a built-in flow meter provides a way for the user to check the flow capability of the respirator before each use.
- Altitude compensation for filter blockage detection capable up to plus or minus 3000 meters.
- Auto pressure sensor zero offset calibration.
- Manual pressure sensor zero offset calibration.
- Low battery audible alarm.
- Breath responsiveness settings.
- Internal battery charger and indication.
- Filter blockage detection both during breathing and mask off.
- Air temperature control (heating and cooling).
- Air humidity control.
- User access to usage info via Bluetooth, such as use hours, breathing rate, filter usage, title volume, etc.

It will be understood to persons skilled in the art of the invention that many modifications may be made without departing from the spirit and scope of the invention.

The invention claimed is:

1. A breathing apparatus, comprising:
a filter arranged to provide filtered air entering the breathing apparatus to a user;
an air flow generator comprising an impeller, the air flow generator being arranged to receive and pressurize the filtered air;
a mask configured to provide the filtered air to the user;
the filter and the air flow generator being housed in a generator unit configured to be arranged substantially at a back of a neck of the user and remote from the mask;
a manifold provided in fluid communication with an airway for conveying the filtered air from the manifold to the mask;
wherein the manifold comprises a first air inlet, a second air inlet positioned parallel to the first air inlet, and an air outlet in fluid communication with each of the first and second air inlets and with the airway, the air flow generator being upstream of the first air inlet;
a first air pathway being defined by the first air inlet and the air outlet, the first air pathway being configured to receive the filtered air from the air flow generator and convey the filtered air to the airway;
a second air pathway being defined by the second air inlet and the air outlet, the second air pathway being configured to receive the filtered air directly from the filter and convey the filtered air to the airway;
further wherein the second air inlet comprises a bypass valve configured to shut when the airflow generator is operating and to open when the air flow generator is not operating; and
whereby the filtered air is provided to the mask either through the air flow generator and through the first air pathway when the air flow generator is operating, or via the bypass valve and through the second air pathway when the air flow generator is not operating;
wherein negative pressure within the mask draws the filtered air through the second air pathway and the bypass valve when the airflow generator is not operating.

2. The breathing apparatus of claim 1, wherein operation of the air flow generator conveys positive pressure filtered air through the first air pathway thereby sealing the bypass valve.

3. The breathing apparatus of claim 2, wherein the manifold is housed in a housing that houses the generator unit.

4. The breathing apparatus of claim 1, wherein the bypass valve is housed in the manifold.

5. The breathing apparatus of claim 3, wherein the airway defines a conduit connected between the air outlet and the mask for conveying the filtered air therebetween.

6. The breathing apparatus of claim 1 further comprising a mask strap connected to the mask and arranged to be passed over a head of the user.

7. The breathing apparatus of claim 6 comprising a head strap integral with the mask strap and which connects the generator unit configured to be arranged around the back of the head of the user and assists in support of the breathing apparatus.

8. The breathing apparatus of claim 1, further comprising a neck support for supporting the generator unit.

9. The breathing apparatus of claim 1, further comprising an exhalation valve adapted to allow air to exhaust from the mask.

10. The breathing apparatus of claim 9, wherein the exhalation valve further comprises a filter arranged to filter the air passing therethrough.

11. The breathing apparatus of claim 9 further comprising an exhaust airway arranged to convey the air from the mask and through the exhalation valve.

12. The breathing apparatus of claim 1, further comprising a pressure sensor in a filtered airflow of the filtered air and a control unit connected thereto to control the airflow generator to vary pressurization of the filtered air in accordance with a reading on the pressure sensor.

* * * * *